United States Patent

Schnabel et al.

[11] Patent Number: 5,723,409
[45] Date of Patent: Mar. 3, 1998

[54] INTERMEDIATES FOR THE PREPARATION OF PHENYLSULFONYLUREA HERBICIDES AND PLANT GROWTH REGULATORS

[75] Inventors: Gerhard Schnabel, Grosswallstadt; Lothar Willms, Hillscheid; Klaus Bauer, Hanau; Hermann Bieringer, Eppstein/Taunus, all of Germany

[73] Assignee: Hoechst Schering AgrEvo GmbH, Berlin, Germany

[21] Appl. No.: 430,343

[22] Filed: Apr. 28, 1995

Related U.S. Application Data

[63] Continuation-in-part of Ser. No. 144,895, Oct. 28, 1993, Pat. No. 5,449,812.

[30] Foreign Application Priority Data

Oct. 31, 1992 [DE] Germany ............... 42 36 902.9

[51] Int. Cl.$^6$ ............... C07D 239/64; C07D 401/12; A01N 43/54
[52] U.S. Cl. ............... 504/214; 504/215; 544/321; 544/333; 544/238; 544/295; 544/296; 544/323; 544/324; 544/331; 544/332; 544/122; 544/123
[58] Field of Search ............... 504/214, 215; 544/321, 333, 238, 295, 296, 323, 324, 331, 332, 122, 123

[56] References Cited

U.S. PATENT DOCUMENTS

| | | | |
|---|---|---|---|
| 4,632,695 | 12/1986 | Schurter et al. | 71/93 |
| 4,664,695 | 5/1987 | Schurter et al. | 71/92 |
| 4,892,946 | 1/1990 | Levitt | 544/321 |
| 4,981,509 | 1/1991 | Hillemann | 71/93 |

FOREIGN PATENT DOCUMENTS

| | | |
|---|---|---|
| 0 001 515 | 5/1983 | European Pat. Off. . |
| 0 116 518 | 10/1987 | European Pat. Off. . |

OTHER PUBLICATIONS

Langmuir, "Formation of Langmuir–Blodgett Films of a Fullerene", 1992, vol. 8, pp. 4–6.

Loev et al., *J. Org. Chem.*, vol. 27 (1962) pp. 2177–2180.

*Primary Examiner*—John M. Ford
*Attorney, Agent, or Firm*—Frommer, Lawrence & Haug LLP

[57] ABSTRACT

The compounds of the formula (I)

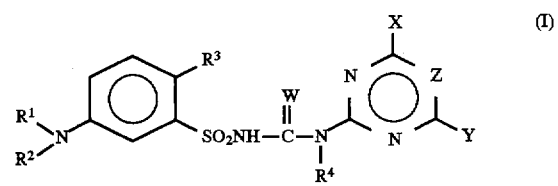

in which $R^1$–$R^4$, W, X, Y and Z are as defined in claim 1 are suitable for controlling harmful plants in crops. Their preparation may employ the intermediates of the formulae II and III:

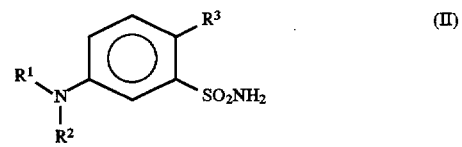

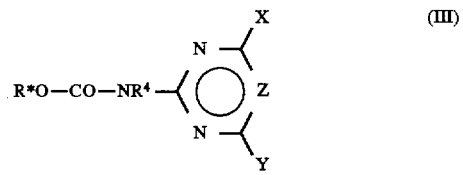

7 Claims, No Drawings

INTERMEDIATES FOR THE PREPARATION OF PHENYLSULFONYLUREA HERBICIDES AND PLANT GROWTH REGULATORS

This application is a continuation-in-part of application Ser. No. 08/144,895, filed Oct. 28, 1993, now U.S. Pat. No. 5,449,812, the disclosure of which application is expressly incorporated herein by reference.

The invention relates to the technical field of herbicides and plant growth regulators, especially herbicides for the selective control of gramineous and other weeds in crops.

It is known that phenylsulfonylureas which are substituted by heterocycles and carry on the phenyl ring an amino group which may be functionalized possess herbicidal and plant growth-regulating properties (EP-A-1 515, U.S. Pat. No. 4,892,946; U.S. Pat. No. 4,981,509; EP-A-116 518, U.S. Pat. No. 4,664,695 and U.S. Pat. No. 4,632,695).

It has now been found that, surprisingly, certain phenylsulfonylureas substituted by heterocycles are particularly highly suitable as herbicides or plant growth regulators.

The present invention relates to compounds of the formula (I) or salts thereof

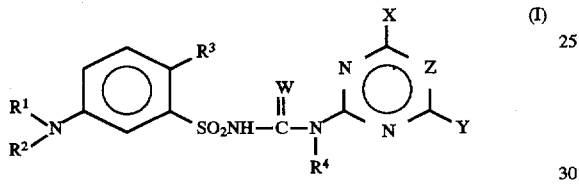

in which $R^1$ is $C_1$–$C_6$-alkyl, $C_2$–$C_6$-alkenyl, $C_2$–$C_6$-alkynyl, the 3 latter radicals independently of one another being unsubstituted or substituted by one or more radicals from the group comprising halogen, $C_1$–$C_4$-alkoxy, $CONH_2$, $C_1$–$C_4$-alkylthio, CN, CHO, ($C_1$–$C_6$-alkyl)carbonyl, ($C_3$–$C_6$-cycloalkyl)carbonyl, $C_1$–$C_4$-alkylsulfonyl, carboxyl, ($C_1$–$C_4$-alkoxy)carbonyl, ($C_2$–$C_4$-alkenyloxy)carbonyl, ($C_2$–$C_4$-alkynyloxy)carbonyl, $NO_2$, $NH_2$, mono- and di-($C_1$–$C_6$)-alkylamino, $R^2$ is CO—$R^5$, COO—$R^6$, CO—$SR^7$, CO—$NR^8R^9$, CS—$NR^{10}R^{11}$, CS—$OR^{12}$, CS—$SR^{13}$, $SO_2R^{14}$, $SO_2NR^{15}R^{16}$, $R^3$ is $COR^{17}$, CO—$OR^{18}$, CO—$NR^{19}R^{20}$, CO—$SR^{21}$, CO—O—N=$CR^{22}R^{23}$, $CSR^{24}$, $CSSR^{25}$, CS—$OR^{26}$, CS—$NR^{27}R^{28}$, C(=$NR^{29}$)$R^{30}$, $R^4$ is H, $C_1$–$C_6$-alkyl, $C_2$–$C_6$-alkenyl, $C_2$–$C_6$-alkynyl, the 3 latter radicals independently of one another being unsubstituted or substituted by one or more halogen radicals, $R^5$ is H, $C_1$–$C_6$-alkyl, $C_2$–$C_6$-alkenyl, $C_2$–$C_6$-alkynyl, the three latter radicals independently of one another being unsubstituted or substituted by one or more radicals from the group comprising halogen, $C_1$–$C_4$-alkoxy, $C_1$–$C_4$-alkylthio and $NR^{31}R^{32}$, or unsubstituted or substituted $C_3$–$C_8$-cycloalkyl, unsubstituted or substituted phenyl, unsubstituted or substituted heteroaryl or phenyl-$C_1$–$C_4$-alkyl which is unsubstituted or substituted on the phenyl ring, $R^6$ is $C_1$–$C_6$-alkyl, $C_2$–$C_6$-alkenyl, $C_2$–$C_6$-alkynyl, the three latter radicals independently of one another being unsubstituted or substituted by one or more radicals from the group comprising halogen, $C_1$–$C_4$-alkoxy, $C_1$–$C_4$-alkylthio and $NR^{31}R^{32}$, or $C_3$–$C_6$-cycloalkyl which is unsubstituted or substituted by one or more radicals from the group comprising halogen, $C_1$–$C_4$-alkyl and $C_1$–$C_4$-alkoxy, or $C_3$–$C_6$-cycloalky-$C_1$–$C_3$-alkyl, $R^7$ is analogous to $R^6$ $R^8$ is H, $C_1$–$C_6$-alkyl, $C_2$–$C_6$-alkenyl, $C_2$–$C_6$-alkynyl, the 3 latter radicals independently of one another being unsubstituted or substituted by one or more radicals from the group comprising halogen, or ($C_1$–$C_6$-alkoxy)carbonyl or $C_1$–$C_4$-alkoxy, $R^9$ is H, $C_1$–$C_6$-alkyl, $C_2$–$C_6$-alkenyl, $C_2$–$C_6$-alkynyl, the 3 latter radicals independently of one another being unsubstituted or substituted by one or more radicals from the group comprising halogen, $C_1$–$C_4$-alkoxy, $C_1$–$C_4$-alkylthio and $NR^{31}R^{32}$, or CO—$R^{33}$, CO—$OR^{34}$, CO—$NR^{35}R^{36}$, CS—$NR^{35}R^{36}$, CS—$R^{33}$ or CS—$OR^{34}$, or $R^8$, $R^9$ taken together are a divalent radical of the formula —(CH$_2$)$_4$—, —(CH$_2$)$_5$—, —CH$_2$CH$_2$—O—CH$_2$CH$_2$—, —CH$_2$CH$_2$NHCH$_2$CH$_2$—, the 4 latter radicals being unsubstituted or substituted by $C_1$–$C_4$-alkyl, $R^{10}$ is analogous to $R^8$, $R^{11}$ is analogous to $R^9$, $R^{12}$ is analogous to $R^6$, $R^{13}$ is analogous to $R^6$, $R^{14}$ is $C_1$–$C_6$-alkyl, $C_2$–$C_6$-alkenyl, $C_2$–$C_6$-alkynyl, the three latter radicals independently of one another being unsubstituted or substituted by one or more radicals from the group comprising halogen, $C_1$–$C_4$-alkoxy, $C_1$–$C_4$-alkylthio and $NR^{31}R^{32}$, $R^{15}$ is analogous to $R^8$, $R^{16}$ is H, $C_1$–$C_6$-alkyl, $C_2$–$C_6$-alkenyl, $C_2$–$C_6$-alkynyl, the 3 latter radicals independently of one another being unsubstituted or substituted by one or more halogen radicals, $R^{17}$ is analogous to $R^5$, $R^{18}$ is $C_1$–$C_6$-alkyl, $C_2$–$C_6$-alkenyl, $C_2$–$C_6$-alkynyl, the three latter radicals independently of one another being unsubstituted or substituted by one or more radicals from the group comprising halogen, $C_1$–$C_4$-alkoxy, $C_1$–$C_4$-alkylthio and $NR^{31}R^{32}$, or $C_3$–$C_6$-cycloalkyl which is unsubstituted or substituted by one or more radicals from the group comprising halogen, $C_1$–$C_4$-alkyl and $C_1$–$C_4$-alkoxy, or $C_3$–$C_6$-cycloalkyl-$C_1$–$C_3$-alkyl or H, $R^{19}$ is analogous to $R^8$, $R^{20}$ is analogous to $R^9$, $R^{21}$ is analogous to $R^{18}$, $R^{22}$ is H, $C_1$–$C_4$-alkyl, $C_3$–$C_5$-alkenyl or $C_3$–$C_5$-alkynyl, $R^{23}$ is H, $C_1$–$C_4$-alkyl, $C_3$–$C_5$-alkenyl or $C_3$–$C_5$-alkynyl, $R_{24}$ is analogous to $R^{17}$, $R^{25}$ is analogous to $R^{18}$, $R^{26}$ is analogous to $R^{18}$, $R^{27}$ is analogous to $R^8$, $R^{28}$ is analogous to $R^9$, $R^{29}$ is H, OH, $NH_2$, $NHR^{37}$, $N(R^{37})_2$, $C_1$–$C_4$-alkyl, $C_1$–$C_4$-alkoxy, $C_2$–$C_4$-alkenyl or $C_2$–$C_4$-alkynyl, the 4 latter radicals independently of one another being unsubstituted or substituted by one or more radicals from the group comprising halogen, $C_1$–$C_3$-alkoxy and $C_1$–$C_3$-alkylthio, $R^{30}$ is H, $C_1$–$C_6$-alkyl, $C_1$–$C_6$-alkoxy, $C_2$–$C_6$alkenyl, $C_2$–$C_6$-alkynyl, the four latter radicals independently of one another being unsubstituted or substituted by one or more radicals from the group comprising halogen, $C_1$–$C_3$-alkoxy and $C_1$–$C_3$-alkylthio, each $R^{31}$ independently of the others is H, $C_1$–$C_4$-alkyl, ($C_1$–$C_4$-alkyl)carbonyl, ($C_1$–$C_4$-alkoxy)carbonyl or CHO, each $R^{32}$ independently of the others is H or $C_1$–$C_4$-alkyl, $R^{33}$ is analogous to $R^5$, $R^{34}$ is analogous to $R^6$, $R^{35}$, $R^{36}$ independently of one another are H, $C_1$–$C_6$-alkyl, $C_2$–$C_6$-alkenyl, $C_2$–$C_6$-alkynyl, the 3 latter radicals independently of one another being unsubstituted or substituted by one or more halogen radicals, $R^{37}$ is $C_1$–$C_4$-alkyl, $C_2$–$C_4$-alkenyl or $C_2$–$C_4$-alkynyl, the three radicals mentioned, independently of one another, being unsubstituted or substituted by one or more radicals from the group comprising halogen, $C_1$–$C_4$-alkoxy and $C_1$–$C_4$-alkylthio, W is O or S, X and Y independently of one another are hydrogen, halogen, $C_1$–$C_6$-alkyl, $C_1$–$C_6$-alkoxy or $C_1$–$C_6$-alkylthio, the three latter radicals being unsubstituted or substituted by one or more radicals from the group comprising halogen, $C_1$–$C_4$-alkoxy and $C_1$–$C_4$-alkylthio, or mono- or di-($C_1$–$C_4$-alkyl)amino, $C_3$–$C_6$-cycloalkyl, $C_3$–$C_5$-alkenyl, $C_3$–$C_5$-alkenyloxy or $C_3$–$C_5$-alkynyloxy, and Z is CH or N.

In the formula (I) and below, each of the radicals alkyl, alkoxy, haloalkyl, haloalkoxy, alkylamino and alkylthio, and the corresponding unsaturated and/or substituted radicals may be straight-chain or branched in the carbon structure. If not indicated specifically, the carbon structures having from 1 to 4 carbon atoms or, in the case of unsaturated groups, having from 2 to 4 carbon atoms are preferred for these radicals. Examples of alkyl radicals, including those in the composite definitions such as alkoxy, haloalkyl etc., are methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals have the meaning of the unsaturated radicals corresponding, where possible, to the alkyl radicals, examples of alkenyl are allyl, 1-methylprop-2-en-1-yl, 2-methylprop-2-en-1-yl, but-2-en-1-yl, but-3-en-1-yl, 1-methylbut-3-en-1-yl, 1-methylbut-2-en-1-yl and 1-methylbut-2-en-1-yl; examples of alkynyl are propargyl, but-2-yn-1-yl, but-3yn-1-yl and 1-methylbut-3-yn-1-yl.

Halogen is fluorine, chlorine, bromine or iodine. Haloalkyl, haloalkenyl and haloalkynyl are respectively alkyl, alkenyl and alkynyl which are partially or completely substituted by halogen, preferably by fluorine, chlorine and/or bromine and in particular by fluorine or chlorine; examples are $CF_3$, $CHF_2$, $CH_2F$, $CF_3CF_2$, $CH_2FCHCl$, $CCl_3$, $CHCl_2$, $CH_2CH_2Cl$; examples of haloalkoxy are $OCF_3$, $OCHF_2$, $OCH_2F$, $CF_3CF_2O$, $OCH_2CF_3$ and $OCH_2CH_2Cl$. This applies correspondingly to haloalkenyl and other halo-substituted radicals.

Aryl is a mono-, bi- or polycyclic aromatic system, for example phenyl, naphthyl, tetrahydronaphthyl, indenyl, indanyl, pentalenyl, fluoranyl and the like, preferably phenyl; aryloxy preferably comprises the oxy radicals corresponding to the aryl radicals mentioned, in particular phenoxy.

Heteroaryl is a mono-, bi- or polycyclic aromatic system in which at least 1 ring contains one or more heteroatoms, for example pyridyl, pyrimidinyl, pyridazinyl, pyrazinyl, thienyl, thiazolyl, oxazolyl, furyl, pyrrolyl, pyrazolyl and imidazolyl, but also bicyclic or polycyclic aromatic or araliphatic compounds, e.g. quinolinyl, benzoxazolyl etc.

A substituted aryl, heteroaryl, phenyl, benzyl or substituted bicyclic radical containing aromatic structures is, for example, a substituted radical derived from the unsubstituted parent structure, examples of substituents being one or more radicals, preferably 1, 2 or 3 radicals from the group comprising halogen, alkyl, haloalkyl, alkoxy, haloalkoxy, alkylthio, hydroxyl, amino, nitro, cyano, alkoxycarbonyl, alkylcarbonyl, formyl, carbamoyl, mono- and dialkylaminocarbonyl, mono- and dialkylamino, alkylsulfinyl and alkylsulfonyl and, in the case of radicals containing carbon atoms, those having from 1 to 4 carbon atoms, in particular 1 or 2 carbon atoms, being preferred. Preferred substituents in general are those from the group comprising halogen, e.g. fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano. Particularly preferred substituents are methyl, methoxy and chlorine.

Substituted or unsubstituted phenyl is, for example, phenyl which is unsubstituted or substituted once or more than once, preferably up to three times, by identical or different radicals from the group comprising halogen, $C_1$–$C_4$-alkyl, $C_1$–$C_4$-alkoxy, $C_1$–$C_4$-haloalkyl, $C_1$–$C_4$-haloalkoxy and nitro, e.g. o-, m- and p-tolyl, dimethylphenyls, 2-, 3- and 4-chlorophenyl, 2,3,4-trifluoro- and -trichlorophenyl, 2,4-, 3,5-, 2,5- and 2,3-dichlorophenyl, o-, m- and p-methoxyphenyl.

A heteroaromatic radical or heterocyclic radical preferably has 5 or 6 members and contains 1, 2 or 3 heteroatoms, preferably from the group comprising N, O and S. The radical may be benzo-fused. Suitable radicals are those such as oxiranyl, pyrrolidinyl, piperidyl, dioxolanyl, pyrazolyl, morpholyl, furyl, tetrahydrofuryl, indolyl, quinolinyl, pyrimidyl, azepinyl, imidazolyl, triazolyl, thienyl and oxazolyl.

The invention also relates to all the stereoisomers encompassed by formula (I), and mixtures thereof. These compounds of the formula (I) contain one or more asymmetric carbon atoms or double bonds which are not indicated specifically in the formula (I). Formula (I) encompasses all the stereoisomers defined by their specific spatial orientation, such as enantiomers, diastereomers, Z- and E-isomers, all of which can be prepared by conventional methods from mixtures of the stereoisomers or else by stereoselective reactions in combination with the use of stereochemically pure starting substances.

The compounds of the formula (I) may form salts in which the hydrogen of the —$SO_2$—NH— group or else another acidic hydrogen atom (e.g. from COOH etc.) is replaced by a cation which is suitable for agriculture. Examples of these salts are metal salts, in particular alkali metal or alkaline earth metal salts, or else ammonium salts or salts with organic amines. The formation of a salt can also take place by the addition of an acid to basic groups such as amino and alkylamino. Suitable acids in this respect are strong inorganic and organic acids, for example HCl, HBr, $H_2SO_4$ or $HNO_3$.

Primarily for reasons of greater herbicidal activity, improved selectivity and/or increased ease of preparation, compounds of the formula (I) or salts thereof of particular interest are those in which $R^1$ is $C_1$–$C_4$-alkyl, $C_2$–$C_4$-alkenyl or $C_2$–$C_4$-alkynyl, preferably $C_1$–$C_4$-alkyl, allyl or propargyl, or $R^2$ is CO—$R^5$, COOR$^6$, CO—NR$^8$R$^9$, CS—NR$^{10}$R$^{11}$, SO$_2$R$^{14}$ or SO$_2$NR$^{15}$R$^{16}$, or $R^3$ is COR$^{17}$, COOR$^{18}$, CONR$^{19}$R$^{20}$ or CO—ON=CR$^{22}$R$^{23}$, preferably COOR$^{18}$, or $R^4$ is H or $C_1$–$C_4$-alkyl, preferably H or methyl, or $R^5$ is H, $C_1$–$C_6$-alkyl which is unsubstituted or substituted by one or more radicals from the group comprising halogen, or by $C_1$–$C_4$-alkoxy, $C_1$–$C_4$-alkylthio or NR$^{31}$R$^{32}$, or $C_3$–$C_6$-cycloalkyl, unsubstituted or substituted phenyl, unsubstituted or substituted benzyl or unsubstituted or substituted heteroaryl, preferably H, $C_1$–$C_6$-alkyl, $C_1$–$C_4$-haloalkyl, cyclopropyl, cyclopentyl, cyclohexyl, phenyl or heteroaryl, the two latter radicals being unsubstituted or substituted by one or more radicals from the group comprising $C_1$–$C_4$-alkyl, $C_1$–$C_4$-alkoxy and halogen, or $R^6$ is $C_1$–$C_6$-alkyl, $C_2$–$C_6$-alkenyl, $C_2$–$C_6$-alklynyl, $C_1$–$C_6$-haloalkyl or $C_3$–$C_6$-cycloalkyl, preferably $C_1$–$C_4$-alkyl, $C_1$–$C_4$-haloalkyl, allyl, propargyl or $C_3$–$C_6$-cycloalkyl, or $R^7$ is $C_1$–$C_4$-alkyl, $R^8$ is hydrogen, $C_1$–$C_6$-alkyl, $C_1$–$C_4$-haloalklyl, $C_1$–$C_4$-alkoxy or ($C_1$–$C_4$-alkoxy)carbonyl, $R^9$ is hydrogen, $C_1$–$C_6$-alkyl which is unsubstituted or substituted by one or more radicals from the group comprising halogen, $C_1$–$C_4$-alkoxy and NR$^{31}$R$^{32}$, or CO—R$^{33}$, CO—OR$^{34}$ or CO—NR$^{35}$R$^{36}$, or $R^8$ and $R^9$ taken together are a divalent radical of the formula —(CH$_2$)$_4$—, —(CH$_2$)$_5$— or —CH$_2$CH$_2$—O—CH$_2$CH$_2$—, or $R^{14}$ is $C_1$–$C_6$-alkyl or $C_1$–$C_6$-haloalkyl, preferably $C_1$–$C_4$-alkyl or $C_1$–$C_4$-haloalkyl, or $R^{15}$, $R^{16}$ independently of one another are hydrogen or $C_1$–$C_4$-alkyl, or $R^{17}$ is hydrogen or $C_1$–$C_4$-alkyl, $C_1$–$C_4$-haloalkyl, $C_3$–$C_6$-cycloalkyl, phenyl or heteroaryl, the two latter radicals being unsubstituted or substituted, or $R^{18}$ is hydrogen, $C_1$–$C_4$-alkyl, $C_2$–$C_6$-alkenyl or $C_2$–$C_6$-alkynyl, the 3 latter radicals being unsubstituted or substituted by one or more radicals from the group comprising halogen, $C_1$–$C_4$-alkoxy, $C_1$–$C_4$-alkylthio and NR$^{31}$R$^{32}$, or $C_3$–$C_6$-cycloalkyl or $C_3$–$C_6$-cycloalkyl-$C_1$–$C_3$-alkyl, or $R^{22}$ is hydrogen or $C_1$–$C_2$-alkyl, or $R^{23}$ is hydrogen or $C_1$–$C_2$-alkyl, or $R^{29}$ is hydrogen, hydroxyl, amino, NHCH$_3$, N(CH$_3$)$_2$, $C_1$–$C_4$-alkyl or $C_1$–$C_4$-alkoxy, $R^{30}$ is hydrogen or $C_1$–$C_4$-alkyl, or
each $R^{31}$ independently of the others is H or $C_1$–$C_4$-alkyl, or each $R^{32}$ independently of the others is H or $C_1$–$C_4$-alkyl, or $R^{33}$ is hydrogen, $C_1$–$C_4$-alkyl, $C_1$–$C_4$-haloalkyl, $C_3$–$C_6$-cycloalkyl or phenyl which is unsubstituted or substituted by one or more radicals from the group comprising halogen, $C_1$–$C_4$-alkyl and $C_1$–$C_4$-alkoxy, or $R^{34}$ is $C_1$–$C_4$-alkyl, allyl, propargyl or cycloalkyl, or $R^{35}$ is hydrogen or $C_1$C$_4$-alkyl, or $R^{36}$ is hydrogen or $C_1$–$C_4$-alkyl, or X is $C_1$–$C_4$-alkyl, $C_1$–$C_4$-alkoxy, $C_1$–$C_4$-haloalkyl, $C_1$–$C_4$-alkylthio, halogen or mono- or di-($C_1$–$C_2$-alkyl) amino, preferably methyl, ethyl, methoxy, ethoxy, methylthio, ethylthio, chlorine, NHCH$_3$ or N(CH$_3$)$_2$, or Y is $C_1$–$C_4$-alkyl, $C_1$–$C_4$-alkoxy, $C_1$–$C_4$-haloalkyl or $C_1$–$C_4$-alkylthio, preferably methyl, ethyl, methoxy or ethoxy, or preferably, those compounds of the formula (I) or salts thereof in which two or more of the particular or preferred definitions mentioned above for the radicals $R^1$ to $R^{36}$ in formula (I) are present in combination.

Preferred compounds of the formula (I) or salts thereof are those in which $R^1$ is methyl, ethyl, n-propyl, i-propyl or allyl, $R^2$ is CO—R$^5$, COOR$^6$, CO—NR$^8$R$^9$, CS—NR$^{10}$R$^{11}$, SO$_2$R$^{14}$ or SO$_2$NR$^{15}$R$^{16}$, $R^5$ is H, $C_1$–$C_4$-alkyl, $C_1$–$C_2$-haloalkyl, cyclopropyl, phenyl, benzyl or hereroaryl having 5 or 6 ring atoms, the 3 latter radicals being unsubstituted or substituted by one or more halogen atoms, $R^6$ is $C_1$–$C_4$-alkyl, allyl, propargyl or cyclopropyl, $R^8$ is H, $C_1$–$C_4$-alkyl, $C_1$–$C_4$-haloalkyl or ($C_1$–$C_4$-alkoxy)carbonyl, $R^9$ is H or $C_1$–$C_4$-alkyl, $R^{10}$ is H or $C_1$–$C_4$-alkyl, $R^{11}$ is H or $C_1$–$C_4$-alkyl, $R^{14}$ is $C_1$–$C_4$-alkyl, $R^{15}$ is H or $C_1$–$C_4$-alkyl and $R^{16}$ is H or $C_1$–$C_4$-alkyl.

$R^5$ is particularly preferably H, CH$_3$, C$_2$H$_5$, n- or i-C$_3$H$_7$, n-, i-, t- or 2-butyl, n-pentyl, CF$_3$, CH$_2$Cl, CHCl$_2$, CCl$_3$, CH$_2$Br, CH$_2$CCl$_3$, cyclopropyl, phenyl, thienyl, furyl or pyridyl, in which case the 4 latter radicals may be substituted by from 1 to 3 halogen atoms.

The present invention also relates to processes for the preparation of the compounds of the formula (I) according to the invention or salts thereof, which comprises a) reacting a compound of the formula (II)

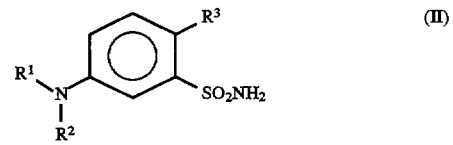

with a heterocyclic carbamate of the formula (III)

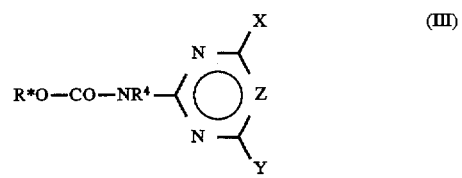

in which R* is unsubstituted or substituted phenyl or $C_1$–$C_4$-alkyl, or b) reacting a sulfonyl isocyanate of the formula (IV)

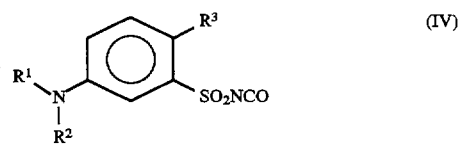

with an amino heterocycle of the formula (V)

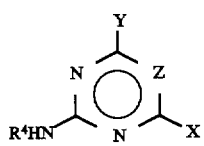

or c) reacting a compound of the formula (II) with a (thio) isocyanate of the formula (X)

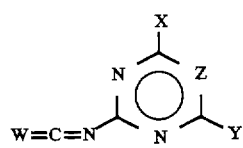

in the presence of a base, the radicals $R^1$ to $R^4$, W, X, Y and Z in the above formulae (II) to (V) and (X) being as defined in formula (I) and, in the case of variants a) and b), the compounds initially obtained being those of the formula (I) in which W=O.

The reaction of the compounds of the formulae (II) and (III) is preferably carried out base-catalyzed in an inert organic solvent, for example dichloromethane, acetonitrile, dioxane or THF, at temperatures between 0° C., preferably 20° C., and the boiling point of the solvent. Examples of the base used are organic amine bases, such as 1,8-diazabicyclo[5.4.0]undec-7-ene (DBU), especially when $R^*$= (substituted) phenyl (cf. EP-A-44 807), or trimethylaluminum or triethylaluminum, the latter especially when $R^*$=alkyl (cf. EP-A-166 516).

The sulfonamides (II) and the sulfonyl isocyanates (IV) are new compounds. They and their preparation are also subjects of the invention.

The compounds of the formula (Ii) are obtained, for example, starting from compounds of the formula (VI)

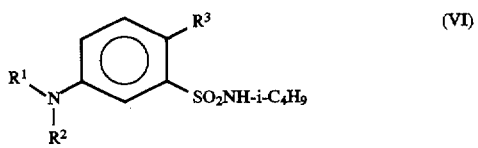

in which $R^1$, $R^2$ and $R^3$ are as defined in formula (I), by reaction with a strong acid (cf. in this respect WO 89/10921).

Examples of suitable strong acids are mineral acids, such as $H_2SO_4$ or HCl, or strong organic acids such as trifluoroacetic acid. The elimination of the tert-butyl protective group is carried out, for example, at temperatures from -20° C. to the respective reflux temperature of the reaction mixture, preferably at 0° C. to 40° C. The reaction can be carried out without solvent or else in an inert solvent, for example dichloromethane or trichloromethane.

The compounds of the formula (VI) are obtained, for example, from the compounds of the formula (VI')—which corresponds to the formula (VI) but in which $R^2$=H— by reaction with suitable electrophiles such as acid chlorides, acid anhydrides, isocyanates, thioisocyanates, sulfonyl chlorides or amidosulfonyl chlorides (cf. in this respect: A. L. J. Beckniter in J. Zabicky. "The Chemistry of Amides", pp. 73–185, Interscience, New York, 1970; E. J. Corey et al., Tetrahedron Lett. 1978, 1051; H. J. Saunders, R. J. Slocombe, Chem. Rev. 43, 203 (1948); S. Ozaki, Chem. Rev. 72, 457, 469 (1972) G. Zölβ, Arzneim.-Forsch. 33, 2 (1983); Houben-Weyl-Hagemann, "Methoden der organischen Chemie [Methods of Organic Chemistry]", 4th edition, vol. E4, p. 485 ff., Thieme Verlag Stuttgart, 1983 J. Golinsky, M. Mahosza, Synthesis 1978, 823; Houben-Weyl-Müller, "Methoden der organischen Chemie", 4th edition, vol. IX, pp. 338–400 and 605–622, Thieme Verlag Stuttgart, 1955; Houben-Weyl-Klarmann, "Methoden der organischen Chemie", 4th edition, vol. E 11/2, pp. 1020–22, Thieme Verlag Stuttgart, 1985; S. Krishnamurthey, Tetrahedron Lett. 23, 3315 (1982)).

The N-monosubstituted aminobenzene derivatives, for example N-alkylaminobenzene derivatives, which are required for this purpose, of the formula (VI') (see formula (VI), $R^2$=H) are obtained by monoalkylation of the anilines of the formula (VI") (=formula (VI), $R^1$=H and $R^2$=H) by standard methods. For example, the N-acylation of the anilines of the formula (VI") with carboxylic acid chlorides or carboxylic acid anhydrides gives the corresponding N-acyl-anilines. The subsequent reduction of the acylamino group to the analogous N-monosubstitutedamino group, e.g. alkylamino group (see above) using suitable reducing agents, for example borane/dimethyl sulfide complex, gives the aniline derivatives of the formula (VI') (=formula (VI), $R^2$=H) in very good yields; see S. Krishnamurthey, Tetrahedron Lett. 23, 3315 (1982).

The aniline derivatives mentioned of the formula (VI') (=formula (VI), $R^1$ and $R^2$=H) are obtained by methods known from the literature, by reduction of the nitro group in compounds (VII), for example by hydrogenation with hydrogen in the presence of a suitable catalyst, as Pd/C or Raney nickel, or by reduction with iron in a medium acidified with acetic acid. (cf. in this respect: H. Berrie, G. T. Neuhold, F. S. Spring, J. Chem. Soc. 1952, 2042; M. Freifelder, "Catalytic Hydrogenation in Organic Synthesis: Procedures and Commentary", J. Wiley and Sons, New York (1978) chapter 5).

The aromatic sulfonamides of the formula (VII) can be obtained from the sulfonic acids of the formula (VIII).

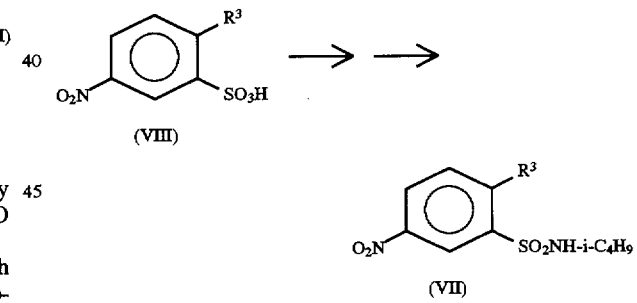

The sulfonic acid group in compounds (VIII) is first converted to the sulfonyl chlorides, for example by standard methods such as the reaction of phosphorus oxychloride or thionyl chloride with potassium salts of the corresponding sulfonic acids in inert solvents such as acetonitrile and/or sulfolane, or without solvent, by heating at reflux (cf. Houben-Weyl-Klamann, "Methoden der organischen Chemie", 4th edition, vol. E XI/2, pp. 1067–1073, Thieme Verlag Stuttgart, 1985).

The formation of sulfonamide from the sulfonyl chlorides using tert-butylamine in ethanol gives the compounds (VII) in good yields (cf. analogous reactions in WO 89/10921).

The sulfonic acids of the formula (VIII) can be prepared from 2-methyl-5-nitrobenzenesulfonic acid, which is available commercially.

The substituent $R^3$ is introduced by oxidation of the methyl group of 2-methyl-5-nitrobenzenesulfonic acid using standard methods, such as the reaction with potassium permanganate to give the carboxy group, followed if desired by derivatization, for example esterification or amidation (cf. in this respect: Houben-Weyl-Falbe: "Methoden der organischen Chemie", 4th edition, vol. E V/1, Thieme Verlag Stuttgart, 1985, pp. 199–202).

A wide variation in the radical $R^3$ can be obtained using a range of standard reactions:

Carboxylic acid amides are obtainable by reacting acid anhydrides or acid chlorides with amines (cf. in this respect: A. L. J. Beckwith in J. Zabicky, "The Chamistry of Amides", pp. 73–185, Interscience, New York 1970).

Thiocarboxylic acid S-esters can be prepared from carboxylic acids and thiols with carbonyl activation, for example using diphenylphosphinyl chloride (cf. in this respect: D. Scholz, D. Eigner, Monatsh. Chemie 110, 759 (1979), S. Yamada et al., J. Org. Chem. 39, 3302 (1974)).

Thiocarboxylic acid O-esters can be prepared by reacting carboxylic acid esters with suitable reagents, for example $P_4S_{10}$ (cf. in this respect: S. O. Lauresson et al., Bull. Soc. Chim. Belg. 87, 293 (1978); T. Nishiwak et al., Chem. Lett. 1980, 401).

Thiocarboxylic acid amides are obtained from carboxylic acid amides by "sulfurization", for example with phosphorus pentasulfide (Houben-Weyl-Falbe, "Methoden der organischen Chemie", 4th edition, vol. E 5/2, pp. 1242–1247 (and literature cited therein), Thieme Verlag Stuttgart, 1985).

Aldehydes can be synthesized from carboxylic acids or esters using a range of reducing agents (Houben-Weyl-Falbe, "Methoden der organischen Chemie", 4th edition, vol. E 3, p. 418 ff., Thieme Verlag Stuttgart, 1983).

Functionalized aldehyde derivatives, for example oximes, oxime ethers, hydrazones etc., can be obtained from the aldehydes by condensation with the corresponding amines (cf. in this respect: Houben-Weyl-Müller, "Methoden der organischen Chemie", 4th edition, vol. 7/1, pp. 453–474, Thiame Verlag Stuttgart, 1954).

N-Alkoxy-carboxylic acid imide esters can be prepared from hydroxamic acid bromide derivatives and alcoholates (E. C. Tayler, F. Kienzle, J. Org. Chem. 36, 233 (1971).

Carboxylic acid imide esters can be obtained from carboxylic acid chloride imides and corresponding alcoholates (cf. in this respect: H. Böhme, O. Müller, Chem. Ber. 98, 1450 (1965); G. Bock, Chem. Ber. 100, 2870 (1967).

O-Acyl oximes can be prepared, for example, by reacting carboxylic acid anhydrides with ketoximes (cf. in this respect: S. Bittner, Y. Knobler, M. Frankel, Tetrahedron Lett. 1965, 95).

Hydroxamic acid amides can be obtained by reacting hydroxamic acid chloride derivatives with amines (cf. in this respect: Houben-Weyl-Müller, "Methoden der organisthen Chemie", 4th edition, vol. 10/4, p. 209 ff., Thieme Verlag Stuttgart, 1968).

Alternatively, the sulfonamides of the formula (II) in which $R^1$ and $R^2$ are not H can be obtained by aminolysis of the corresponding sulfonyl chlorides of the formula (IXb)

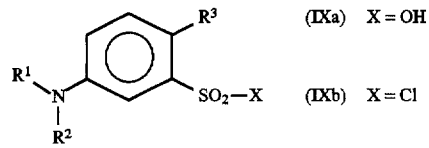

(IXa) X = OH
(IXb) X = Cl which in turn are readily obtainable from the sulfonic acids (IXa) by the standard methods mentioned (see abovementioned reactions of (VIII) to (VII)).

The compounds (IXa) can in turn be obtained from the nitrobenzenesulfonic acid (VIII) by the sequence of reactions (1) reduction by analogy with reduction of (VII),
(2) N-alkylation and
(3) N-acylation, the latter being as described in the preparation of (VI).

The carbamates of the formula (III) which are required for the reaction of compounds (II) by variant a) are known from the literature or can be prepared by analogy with known processes (cf. EP-A-70 804 or U.S. Pat. No. 4,480,101).

The compounds of the formulae (IV) and (V) which can be employed for the process variants b) can also be prepared from the abovementioned compounds of the formulae (III) and (VIII) and their precursors by, or by analogy with, methods which are known in general terms.

The phenylsulfonyl isocyanates of the formula (IV) can be prepared, for example, by analog with the processes from EP-A-184 385 starting from compounds of the formula (II) and using, for example, phosgene.

The reaction of the compounds (IV) with the amino heterocycles of the formula (V) is preferably carried out in inert aprotic solvents, for example dioxane, acetonitrile or tetrahydrofuran, at temperatures between 0° C. and the boiling temperature of the solvent.

The (thio)isocyanates of the formula (X) can be prepared by methods known from the literature (cf. EP-A-232 067, EP-A-166 516).

The reaction of compounds of the formula (X) with sulfonamides of the formula (II) is carried out at temperatures of between −10° C. and +10° C., preferably between +20° and +80° C., in an inert aprotic solvent, for example acetone or acetonitrile, in the presence of a suitable base such as triethylemine or potassium carbonate.

The salts of the compounds of the formula (I) are preferably prepared in inert solvents such as water, methanol, acetone, dichloromethane, tetrahydrofuran, toluene or heptane, at temperatures from 0° to 100° C. Examples of bases suitable for the preparation of the salts according to the invention are alkali metal carbonates, such as potassium carbonate, alkali metal end alkaline earth metal hydroxides, ammonia or a suitable amine base, such as triethylemine or ethanolamine. Examples of acids suitable for salt formation are HCl, HBr, $H_2SO_4$ or $HNO_3$.

The inert solvents referred to in the abovementioned process variants are in each case solvents which are inert under the respective reaction conditions, but which are not necessarily inert under any reaction conditions.

The compounds of the formula (I) according to the invention or their salts have an excellent herbicidal activity against a broad range of economically important monocotyledon and dicotyledon harmful plants. The active substances also act efficiently on perennial weeds which produce shoots from rhizomes, root stocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be controlled by the compounds according to the invention, without the mention intending restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cymodon, Imperata and Sorghum, and also perennial Cyperus species.

In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention likewise effect outstanding control of weeds which occur under the specific conditions of rice-growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops and, eventually, after three to four weeks have elapsed, they die completely.

If the active substances are applied post-emergence on the green parts of the plants, growth likewise stops drastically a very short time after the treatment and the weed plants remain at the growth stage of the point in time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledon and dicotyledon weeds, crop plante of economically important crops, such as, for example, wheat, barley, rye, rice, maize, sugar beet, cotton and soya, are damaged not at all, or only to a negligible extent. For these reasons, the present compounds are highly suitable for selectively controlling unwanted plant growth in agricultural crop plants.

In addition, the substances according to the invention exhibit outstanding growth-regulatory properties in crop plants. They intervene to regulate the plant metabolism and can therefore be employed so as to have a specific influence on substances contained in plants, and for facilitating harvesting, for example by initiating desiccation and growth compression. Furthermore, they are also suitable for the general control and inhibition of unwanted vegetative growth, without killing off the plants in the process. Inhibition of vegetative growth plays an important role in many monocotyledon and dicotyledon crops, since it can reduce or completely prevent lodging.

The compounds according to the invention can be used in the form of wettable powders, emulsifiable concentrates, sprayable solutions, dusting agents or granules in the conventional formulations. The invention therefore also relates to herbicidal and plant growth-regulating agents comprising compounds of the formula (I) or salts thereof.

The compounds of the formula (I) or salts thereof can be formulated in a variety of ways, as predetermined by the biological and/or chemicophysical parameters. The following possibilities are therefore suitable for formulation: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water base, oil-miscible solutions, capsule suspensions (CS), dusting agents (DP) seed-dressing agents, granules for scattering and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example in: Winnacker-Küchler, "Chemische Technologie [Chemical Technology]", Volume 7, C. Hauser Verlag Munich, 4th Ed., 1986; Wade van Valkenburg, "Pesticide Formulations", Marcel Dekker New York, 1973; K. Martens, "Spray Drying" Handbook, 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluent and Carriers", 2nd Ed., Darland Books, Caldwell N.J., H.v. Ophen, "Introduction to Clay Colloid Chemistry", 2nd Ed., J. Wiley & Sons, New York; C. Marsden, "Solvents Guide", 2nd Ed., Interscience, New York 1963; McCutcheon's "Detergents and Emulsifiers Annual", MC Publ. Corp. Ridgewood N.J.; Sisleyand Wood, "Encyclopedia of Surface Active Agents", Chem. Publ. Co. Inc., New York 1964; Schönfeldt, "Grenzfl achenaktive Äthylenoxidaddukte" [Surface-active Ethylene Oxide Adducts] Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, such as insecticides, acaricides, herbicides, fungicides, safeners, fertilizers and/or growth regulators may also be prepared on the basis of these formulations, for example in the form of a ready-to-use formulation or as a tank mix.

Wettable powders are preparations which are uniformly dispersible in water and which, besides the active substance, also contain surfactants of ionic and/or nonionic type (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate, or alternatively sodium oleoylmethyltaurinate, in addition to a diluent or inert substance. The wettable powders are prepared by finely grinding the herbicidal active substances, for example, in conventional apparatus such as hammer mills, blower mills and air-jet mills, and mixing them simultaneously or subsequently with the formulation auxiliaries.

Emulsifiable concentrates are prepared by dissolving the active substance in an organic solvent, for example butanol, cyclohexanone, dimethylformamide, xylene and also higher-boiling aromatic compounds or hydrocarbons or mixtures of the organic solvents, with the addition of one or more surfactants of ionic and/or nonionic type (emulsifiers). Examples of emulsifiers which can be used are: calcium salts of an alkylarylsulfonic acid such as Ca dodecylbenzenesulfonate, or nonionic emulsifiers, such as fatty acid polyglycol asters, alkylaryl polyglycol ethers, fatty alcohol polyglycol ethers, propylene oxide/ethylene oxide condensation products, alkyl polyethers, sorbitan esters, such as sorbitan fatty acid esters or polyoxyethylene sorbitan esters, such as polyoxyethylene sorbitan fatty esters.

Dusting agents are obtained by grinding the active substance with finely divided solid substances, for example talc or natural clays, such as kaolin, bentonite, pyrophyllite or diatomaceous earth.

Suspension concentrates may be based on water or oil. They can be prepared by, for example, wet grinding using conventional bead mills with the possible addition of surfactants as already mentioned, for example, above for the other types of formulation.

Emulsions, for example oil-in-water emulsions (EW), can be prepared, for example, by means of stirrers, colloid mills and/or static mixers, using aqueous organic solvents and, if desired, surfactants, for example as already listed above for the other types of formulation.

Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

Water-dispersible granules are generally prepared by conventional methods such as spray-drying, fluidized-bed granulation, plate granulation, mixing using high-speed mixers and extrusion without solid inert material.

The agrochemical formulations generally contain from 0.1 to 99% by weight and in particular from 0.1 to 95% by weight of active substance of the formula (I) or salts thereof.

The concentration of active substance in wettable powders is, for example, about 10 to 90% by weight; the remainder to 100% by weight is composed of conventional formulation components. In the case of emulsifiable concentrates, the concentration of active substance can be about 1 to 90, preferably 5 to 80% by weight. Formulations in the form of dusts usually contain 1 to 30, preferably 5 to 20% by weight of active substance, sprayable solutions about 0.05 to 80, preferably 2 to 50% by weight. In the case of water-dispersible granules, the active substance content depends partly on whether the active compound is liquid or solid and on which granulation auxiliaries, fillers etc. are used. In the case of the water-dispersible granules, the content of active substance is, for example, between 1 and 95% by weight and preferably between 10 and 80% by weight.

In addition, the active substance formulations mentioned contain, if appropriate, the adhesives, wetting agents, dispersants, emulsifiers, penetrants, preservatives, frost protectors and solvents, fillers, carriers and colorants, antifoams, evaporation inhibitors and agents influencing the pH and the visocity which are conventional in each case.

Combination partners which can be employed for the active substances according to the invention in mixed formulations or as a tank mix are, for example, known active substances as described in, for example, Weed Research 26, 441–445 (1986), or "The Pesticide Manual", 9th edition, The British Crop Protection Council, 1990/91, Bracknell, England, and the literature quoted therein. Examples of herbicides known from the literature which can be combined with the compounds of the formula (I) are the following active substances (note: the compounds are either given by their common name in accordance with the International Organization for Standardization (ISO) or by the chemical name, together if appropriate with a common code number):

acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenylacetemide; CDEC, i.e. 2-chloroallyl diethyldithiocarbamate; CGA 184927, i.e. 2-[4-[(5-chloro-3-fluoro-2-pyridinyl)oxy]phenoxy] propanoic acid and its 2-propynyl ester; chlomethoxyfen; chloramben; chlorazifop-butyl; pirifenop-butyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthaldimethyl; chlorthiamid; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmediphan; desmetryn; di-allate; dicamba; dichlobenil; dichlorprop; diclofop-methyl; diethatyl; difenoxuron; difenzoquat; diflufenican; dimefuron; dimethachlor; dimethametryn; dimethazone; clomazon; dimethipin; dimetrasulfuron, cinosulfuron; dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethafluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl] phenyl]ethanesulfonamide; F6285, i.e. 1-[5-(N-methylsulfonyl)amino-2,4-dichlorophenyl]-3-methyl-4-difluoromethyl-1,2,4-triazol-5-one; fenoprop; fenoxan, s. clomazon; fenoxaprop-ethyl; fenuron; flamprop-methyl; flazasulfuron; fluazifop and its ester derivatives; fluchloralin; flumetsulam; N-[2,6-difluorophenyl]-5-methyl-1,2,4-triazolo[1,5a] pyrimidin-2-sulfonamide; flumeturon; flumipropyn; fluorodifen; fluoroglycofen-ethyl; fluridone; flurochloridone; fluroxypyr; flurtamone; fomesafen; fosamine; furyloxyfen; glufosinate; glyphosate; halosaten; haloxyfop and its ester derivatives; hexazinone; Hw 52, i.e. N-(2,3-dichlorophenyl)-4-(ethoxymethoxy) benzamide; imazamethabenzmethyl; imazapyr; imazaquin; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methenyldymron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenisopham; phenmedipham; picloram; piperophos; piributicarb; pirifenop-butyl; pretilachlor; primisulfuronmethyl; procyazine; prodiamine; profluralin; proglinazine-ethyl; prometon; prometryn; propachlor; propanil; propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and its ester derivatives, quizalofop and its ester derivatives; quizalofop-ethyl; quizalofop-p-tefuryl; renriduron; dymron; S 275, i.e. 2-[4-chloro-2-fluoro-5-(2-propynyloxy)phenyl]-4,5,6, 7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoromethyl)phenoxy]-2-naphthyl]oxy]propanoic acid and its methyl ester; sulfometuron-methyl; sulfazuron; flazasulfuron; TCA; tebutam; tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thiazafluoron; thifensulfuron-methyl; thiobencarb; tiocarbazil; tralkoxydim; tri-allate; triasulfuron; triazofenamide; tribenuron-methyl; triclopyr; tridiphane; trietazine; trifluralin; trimeturon; vernolate; WL 110547, i.e. 5-phenoxy-1-[3-(trifluoromethyl)phenyl]-1H-tetrazole.

For use, the formulations, present in commercially available form, are diluted, if appropriate, in a customary manner, for example using water in the case of wettable powders, emulsifiable concentrates, dispersions and water-dispersible granules and then applied to plants, plant parts or agriculturally or industrially utilized soil, on which the plants are located, or in which they grow or are present as seed. Preparations in the form of dusts or granules for soil application and scattering, and also sprayable solutions, are usually not further diluted with other inert substances before use.

The application rate required for the compounds of the formula I varies with the external conditions, such as, inter alia, temperature, humidity, and the nature of the herbicide used. It can vary within wide limits, for example between 0.001 and 10.0 kg/ha or more of active substance; preferably, however, it is between 0.005 and 5 kg/ha.

A) CHEMICAL EXAMPLES a) 2-Carboxy-nitrobenzenesulfonic acid 400.0 g (2.53 mol) of potassium permanganate are added in portions at 80° C. over a period of 2 h to a solution of 106.0 g (0.40 mol) of 2-methyl-5-nitrobenzenesulfonic acid and 80.0 g (0.58 mol) of potassium carbonate in 1300 ml of water. The reaction temperature is maintained at between 80° and 95° C.

After stirring for a further 4 h, the solid formed is filtered off. The filtrate is acidified with concentrated hydrochloric acid (pH=1). The colorless 2-carboxy-5-nitrobenzenesulfonic acid which has precipitated is filtered off with suction through a Büchner funnel and dried at about 50° C./100 torr (82.0 g; 83.7% of theory). Melting point: >300° C.

b) 2-Methoxycarboxy-5-nitrobenzenesulfonic acid

A suspension of 190.0 g (0.77 mol) of 2-carboxy-5-nitrobenzenesulfonic acid, 10 ml of DMF and 250 ml (3.43 mol) of thionyl chloride is heated at boiling for 3 h. After separating off the insoluble constituents by filtration, the filtrate is concentrated. 200 ml (4.94 mol) of methanol are added to the residue which results. When addition is complete the reaction mixture is cooled to 0° C. The solid which precipitates is filtered off and dried. 70.9 g (35.3% of theory) of colorless, crystalline 2-methoxycarbonyl-5-nitrobenzenesulfonic acid (m.p.: 92°–94° C.) are thus obtained. By distilling off the volatile components from the mother liquor, a second fraction (62.5 g, 31.1% of theory) is obtained.

c) 2-Methoxycarbonyl-5-nitrobenzenesulfonyl chloride

A solution of 17.3 g (0.27 mol) of potassium hydroxide (88% strength) and 100 ml of methanol is added carefully with vigorous stirring to a solution of 70.9 g (0.27 mol) of 2-methoxycarbonyl-5-nitrobenzenesulfonic acid in 300 ml of methanol. The mixture is cooled to 0° C. and the salt which is precipitated is filtered off, dried and then suspended in 150 ml of sulfolane, 150 ml of acetonitrile and 10 ml of dimethylformamide. After the dropwise addition of 100 ml (1.07 mol) of phosphorus oxychloride, the mixture is heated at boiling for 2.5 h. The reaction mixture is then poured into ice-water. The 2-methoxycarbonyl-5-nitrobenzenesulfonyl chloride (60.1 g, 70% of theory) which has precipitated is filtered off with suction through a Büchner funnel and freed from traces of solvent under reduced pressure. Melting point: 86°–88° C.

d) N-tert-Butyl-2-methoxycarbonyl-5-nitrobenzenesulfonamide 50 ml (0.48 mol) of tert-butylamine are slowly added dropwise at 0° C. to a solution of 34.4 g (0.12 mol) of 2-methoxycarbonyl-5-nitrobenzenesulfonyl chloride in 200 ml of ethyl acetate and 250 ml of ethanol. The reaction solution is then stirred for a further 10 min at room temperature. After the addition of 500 ml of water, a colorless solid crystallizes out. It is filtered off and dried to give 28.1 g (89% of theory) of N-tert-butyl-2-methoxycarbonyl-5-nitrobenzenesulfonyl chloride. m.p.: 121°–124° C.

e) N-tert-Butyl-5-amino-2-methoxycarbonylbenzenesulfonamide 25.08 g (0.079 mol) of N-tert-butyl-2-methoxycarbonyl-5-nitrobenzenesulfonamide are dissolved in 1000 ml of MeOH. 0.50 g of Pd—C (10%) is added and the mixture is shaken under a hydrogen atmosphere (1 atm) until the uptake of hydrogen has finished. The catalyst is separated off and the solvent is removed by distillation. The residue is induced to crystallize by stirring with a little ethyl acetate. The resulting N-tert-butyl-5-amino-2-methoxycarbonylbenzenesulfonamide (18.3 g; 80.9% of theory) melts at 193° C.

f) N-tert-Butyl-5-formylamino-2-methoxycarbonylbenzenesulfonamide 6.5 ml of formic acid are carefully added at 0° C. to 13 ml of acetic anhydride. The mixture is subsequently heated at 50°–60° C. for 2 h. A solution of 16.0 g (0.056 mol) of N-tert-butyl-5-amino-2-methoxycarbonylbenzenesulfonamide in 50 ml of DMF is then added dropwise at 0° C. The cooling bath is removed and the mixture is stirred for a further 4 h at room temperature. The reaction mixture is then shaken up in 800 ml of ethyl acetate and washed with three times 150 ml of water. The organic phase is dried over magnesium sulfate, the solvent is distilled off, and the residue is recrystallized from ethyl acetate/n-heptane. The product is N-tert-butyl-5-formylamino-2-methoxycarbonylbenzenesulfonamide (14.23 g, 82% of theory) which melts at 113°–114° C.

g) N-tert-Butyl-2-methoxycarybonyl-5-methylaminobenzenesulfonamide 9.92 g (0.032 mol) of N-tert-butyl-5-formylamino-2-methoxycarbonylbenzenesulfonamide are dissolved in 50 ml of CHCl$_3$, and then 5 ml (0.053 mol) of boranedimethyl sulfide complex are added at 0° C. After 1 h at 0° C. and 3 h at room temperature the reaction mixture is cooled to 0° C. 30 ml of methanol are added and the mixture is washed with water. The organic phase is dried over magnesium sulfate, the solvent is removed by distillation, and 9.23 g (98% of theory) of N-tert-butyl-2-methoxycarbonyl-5-methylaminobenzenesulfonamide are obtained. m.p.: 120°–124° C.

h) N-tert-Butyl-5-[N-(ethoxycarbonylaminothiocarbonyl)methylamino]-2-methoxyrcarbonylbenzenesulfonamide 1.20 g (4.0 mmol) of N-tert-butyl-2-methoxycarbonyl-5-methylaminobenzenesulfonamide is dissolved in 5 ml of anhydrous DMF, and 0.60 g (4.3 mmol) of 95% strength ethoxycarbonyl isothiocyanate is added. After 3 h at room temperature the mixture is taken up in ethyl acetate and washed with 1N hydrochloric acid and water. The organic phase is dried over magnesium sulfate and the solvent is removed by distillation. The residue is taken up in a little ethyl acetate and precipitated with heptane at –25° C. The precipitate is filtered off with suction and dried to give 1.29 g (75% of theory) of colorless N-tert-butyl-5-[N-(ethoxycarbonylaminothiocarbonyl)methylamino]-2-methoxycarbonylbenzenesulfonamide. m.p.: 110° C.

i) 5-[N-(Ethoxycarbonylaminothiocarbonyl)methylamino]-2-methoxycarbonylbenzenesulfonamide 1.05 g (2.4 mmol) of N-tert-butyl-5-[N-(ethoxycarbonylaminothiocarbonyl)methylamino]-2-methoxycarbonylbenzenesulfonamide is stirred for 18 h in 15 ml of trifluoroacetic acid at room temperature. Volatile components are then removed by distillation at 12 torr/50° C. The residue is suspended in toluene. The suspension is again concentrated at 12 torr/50° C. to give a highly viscous residue (0.85 g, 93% of theory) which is reacted directly without further purification to give the corresponding sulfonylurea (cf. Example j).

j) N-[(4,6-Dimethoxypyrimidin-2-yl)aminocarbonyl]-5-[N-(ethoxycarbonylaminothiocarbonyl)methyamino]-2-methoxycarbonylbenzenesulfonamide (see tabular Example 2192)

1.2 ml of DBU is added to a suspension of 0.69 g (1.84 mol) of 5-[N-(ethoxycarbonylaminothiocarbonyl)methylamino]-2-methoxycarbonylbenzenesulfonamide and 0.55 g (1.99 mmol) of 4,6-dimethoxy-2-phenoxycarbonylaminopryimidine in 5 ml of acetonitrile. The mixture is stirred for 17 h at room temperature and the solvent is then removed by distillation. The residue is taken up in water and washed with diethyl ether. The aqueous phase is acidified with concentrated hydrochloric acid (pH= 1) and produces a colorless precipitate, which is filtered off and induced to crystallize by stirring with a little methanol. The resulting product is 0.61 g (60% of theory) of N-[(4,6-dimethoxypyrimidin-2-yl)aminocarbonyl]-5-[N-(ethoxycarbonylaminothiocarbonyl)methylamino]-2-methoxycarbonylbenzenesulfonamide. m.p.: 144°–145° C.

k) 5-[N-(Acetylmethylamino)-N-(4,6-dimethoxypryrimidin-2-yl)aminocarbonyl]-2-methoxycarbonylbenzenesulfonamide (see Table 1, Example 89)

0.45 ml of DBU is added to a mixture of 0.75 g (2.6 mmol) of 5-(N-acetylmethylamino)-2-methoxycarbonylbenzenesulfonamide and 0.73 g (2.6 mmol) of 4,6-dimethoxy-2-(phenoxycarbonylamino) pyrimidine in 10 ml of CH$_3$CN. The mixture is worked up in analogy to Example j) to give 0.59 g of the desired sulfonylurea, m.p.: 197° C.

l) 2-Methoxycarbonyl-5-(N-methoxycarbonyl-N-methylamino)benzenesulfonyl isocyanate 5.0 g of 2-methoxycarbonyl-5-(N-methoxycarbonyl-N-methylamino)benzenesulfonamide are suspended in 17 ml of 1,2-dichloroethane. 4 ml of thionyl chloride are added and the reaction mixture is heated at boiling for 5 h.

The reaction mixture is cooled to room temperature, 0.3 ml of pyridine is added, phosgene is passed into the reaction mixture, and the solution is heated at reflux for 4 h. The reaction mixture is concentrated to give 6.3 g of an oil which is employed directly in the subsequent reaction (Examples m, n, o).

m) 2-Methoxycarbonyl-5-(N-methoxycarbonyl-N-methylamino)-N-[(4,6-dimethylpyrimidin-2-yl)aminocarbonyl]benzenesulfonamide (see Table 1, Example 1,183)

A solution of 2.1 g of 2-methoxycarbonyl-5-(N-methoxycarbonylmethylamino)benzenesulfonyl isocyanate (Example 1)) in 20 ml of dichloroethane is added to a solution of 0.8 g of 2-amino-4,6-dimethylpyrimidine in 20 ml of dichloroethane. The reaction mixture is stirred for 8 h at 40° C. and then concentrated. The residue is induced to form the product by stirring intensively and successively with 1N hydrochloric acid and methanol, to give 0.47 g of the desired sulfonylurea as a solid foam:

hu 1H NMR (DMSO, 80 MHz); δ (ppm)=2.5 (s, 6H, 2 CH$_3$), 3.3 (s, 3H, N—CH$_3$), 3.7 (s, 3H, O—CH$_3$), 3.9 (s, 3H, OCH$_3$), 7.0 (s, 1H, H$_{pyrimidine}$), 7.8 (s, 2H, 3-H and 4-H), 8.1 (s, 1H, 6-H), 10.6 (s, 1H, NH), 13.3 (s, 1H, SO$_2$—NH).

n) N-[(4-Chloro-6-methoxypyrimidin-2-yl)aminocarbonyl]-2-methoxycarbonyl-5-(N-methoxycarbonyl-N-methylamino)benzenesulfonamide (see Table 1, Example 1,185)

By analogy with Example m), 0.9 g of 2-amino-4-chloro-6-methoxypryrimidine is reacted with 2.1 g of 2-methoxycarbonyl-5-(N-methoxycarbonyl-N-methylamino)benzenesulfonyl isocyanate (Example 1)). Yield: 0.45 g of the desired sulfonylurea as a solid foam:

$^1$H NMR (DMSO, 80 MHz): δ (ppm)=3.3 (s, 3H, N—CH$_3$), 3.7 (s, 3H, O—CH$_3$), 3.8 (s, 3H, O—CH$_3$), 4.0 (s, 3H, O—CH$_3$), 6.8 (s, 1H, H$_{pyrimidine}$), 7.7 (s, 2H, 3-H and 4-H), 10.9 (s, 1H, NH), 12.0 (s, 1H, SO$_2$—NH).

o) N-[N-(4-Methoxy-6-methyltriazin-2-yl)aminocarbonyl]-2-methoxycarbonyl-5-(N-methoxycarbonyl-N-methylamino)benzenesulfonamide (see Table 1, Example 1,180)

By analogy with Example m), 0.85 g of 2-amino-4-methoxy-6-methyltriazine is reacted with 2.1 g of 2-methoxycarbonyl-5-(N-methoxycarbonyl-N-methylamino)benzenesulfonyl isocyante (Example 1)). Yield: 0.47 g of the desired sulfonylurea as a solid foam:

$^1$H NMR (DMSO, 80 MHz): δ (ppm)=2.4 (s, 3H, CH$_3$), 3.3 (s, 3H, N—CH$_3$), 3.7 (s, 3H, OCH$_3$), 3.8 (s, 3H, OCH$_3$), 4.0 (s, 3H, O—CH$_3$), 7.8 (s, 2H, 3-H, 4-H), 8.1 (s, 1H, 6-H), 11.0 (s, 1H, NH), 12.3 (s, 14, SO$_2$NH).

The remainder of the compounds described in Table 1 are obtained in a manner analogous to Examples a) to o).

The following abbreviations are used in Table 1:

No.=Example number
m.p.=solidification point (melting point) in °C.
Me=methyl
Et=ethyl
Pr=n-propyl
n-Pr=n-propyl
i-Pr=i-propyl
c-Pr=cyclopropyl
Bu=butyl
Ph=phenyl.

TABLE 1

| No. | R$^1$ | R$^2$ | R$^3$ | R$^4$ | X | Y | Z | m.p. |
|---|---|---|---|---|---|---|---|---|
| 1 | Me | CO—CH$_2$—OMe | CO$_2$Me | H | OMe | OMe | CH | |
| 2 | Et | " | " | " | " | " | " | |
| 3 | Me | COCH$_2$NHCO$_2$Me | " | " | " | " | " | |
| 4 | Me | COCH$_2$SMe | " | " | " | " | " | |
| 5 | " | " | " | Me | " | " | " | |
| 6 | " | " | " | H | OMe | Me | N | |
| 7 | " | " | " | " | Me | Me | CH | |
| 8 | Et | " | " | " | " | " | " | |
| 9 | " | " | " | " | OMe | " | N | |
| 10 | " | " | " | " | OMe | OMe | N | |
| 11 | Me | CHO | " | " | OMe | OMe | CH | 177–182 |
| 12 | " | " | " | " | OMe | OMe | N | 180–181 |
| 13 | " | " | " | " | OMe | Me | N | 160–164 |
| 14 | " | " | " | " | OMe | Me | CH | |
| 15 | " | " | " | " | NMe$_2$ | OCH$_2$CF$_3$ | N | 93–95 |
| 16 | " | " | " | " | Me | Me | CH | 161–164 |
| 17 | " | " | " | " | Me | Me | N | |
| 18 | " | " | " | " | Cl | OMe | CH | 184–186 |
| 19 | " | " | " | Me | OMe | OMe | CH | |
| 20 | " | " | " | Me | OMe | Me | N | |
| 21 | " | " | CO$_2$Et | H | OMe | OMe | CH | |
| 22 | " | " | " | " | OMe | Cl | CH | |
| 23 | " | " | " | " | Me | Me | CH | |
| 24 | " | " | " | " | OMe | Me | N | |
| 25 | " | " | " | " | NMe$_2$ | OCH$_2$CF$_3$ | N | |
| 26 | " | " | " | Me | OMe | OMe | CH | |
| 27 | " | " | " | Me | OMe | Me | N | |
| 28 | " | " | CO$_2$-n-Pr | H | OMe | OMe | CH | |
| 29 | " | " | " | " | OMe | OMe | N | |
| 30 | " | " | " | " | OMe | Me | N | |
| 31 | " | " | " | " | Me | Me | CH | |
| 32 | " | " | " | " | OMe | Cl | CH | |
| 33 | " | " | " | Me | Me | OMe | N | |
| 34 | " | " | " | Me | OMe | OMe | CH | |
| 35 | Me | CHO | CO$_2$-i-Pr | H | OMe | OMe | CH | |
| 36 | " | " | " | " | OMe | OMe | N | |
| 37 | " | " | " | " | OMe | Me | N | |
| 38 | " | " | " | " | OMe | Cl | CH | |
| 39 | " | " | " | " | Me | Me | CH | |
| 40 | " | " | " | " | SMe | NEt$_2$ | N | |
| 41 | " | " | CO$_2$-i-Pr | Me | OMe | Me | N | |
| 42 | " | " | " | Me | OMe | OMe | CH | |
| 43 | Me | CHO | CO$_2$-Allyl | H | OMe | OMe | CH | |
| 44 | Et | CHO | CO$_2$Me | H | OMe | OMe | CH | 161–163 |
| 45 | " | " | " | " | OMe | Me | N | |
| 46 | " | " | " | " | Me | Me | CH | |
| 47 | " | " | " | " | Cl | OMe | CH | |
| 48 | " | " | " | Me | OMe | OMe | CH | |
| 49 | " | " | " | Me | OMe | Me | N | |
| 50 | " | " | CO$_2$Et | H | OMe | OMe | CH | |
| 51 | " | " | " | " | OMe | Me | CH | |
| 52 | " | " | " | " | Cl | OMe | CH | |
| 53 | " | " | " | " | OMe | Me | N | |

TABLE 1-continued

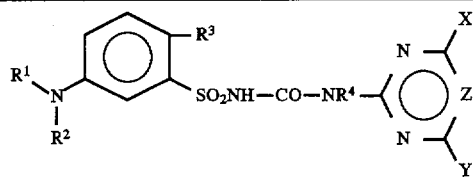

| No. | R¹ | R² | R³ | R⁴ | X | Y | Z | m.p. |
|---|---|---|---|---|---|---|---|---|
| 54 | " | " | " | Me | OMe | OMe | CH | |
| 55 | " | " | " | Me | OMe | Me | N | |
| 56 | " | " | CO₂-n-Pr | H | OMe | OMe | CH | |
| 57 | " | " | " | " | OMe | Me | N | |
| 58 | " | " | " | " | OMe | Cl | CH | |
| 59 | " | " | " | " | Me | Me | CH | |
| 60 | " | " | " | Me | OMe | OMe | CH | |
| 61 | " | " | " | Me | OMe | Me | N | |
| 62 | " | " | CO₂-i-Pr | H | OMe | OMe | CH | |
| 63 | " | " | " | " | OMe | Me | N | |
| 64 | " | " | " | " | Me | Me | CH | |
| 65 | " | " | " | Me | OMe | Me | N | |
| 66 | n-Pr | CHO | CO₂Me | H | OMe | OMe | CH | |
| 67 | " | " | " | " | OMe | Cl | CH | |
| 68 | " | " | " | " | Me | Me | CH | |
| 69 | " | " | " | " | OMe | Me | N | |
| 70 | " | " | " | Me | OMe | OMe | CH | |
| 71 | " | " | " | Me | OMe | Me | N | |
| 72 | n-Pr | " | CO₂Et | H | OMe | Me | N | |
| 73 | " | " | " | " | OMe | OMe | CH | |
| 74 | " | " | " | " | Me | Me | CH | |
| 75 | " | " | CO₂n-Pr | " | OMe | OMe | CH | |
| 76 | i-Pr | " | CO₂Me | H | OMe | OMe | CH | |
| 77 | " | " | " | " | OMe | Me | N | |
| 78 | " | " | " | " | Me | Me | CH | |
| 79 | " | " | " | " | Cl | OMe | N | |
| 80 | " | " | " | Me | OMe | Me | N | |
| 81 | " | " | " | Me | OMe | OMe | CH | |
| 82 | Allyl | " | CO₂Me | H | OMe | OMe | CH | |
| 83 | " | " | " | " | OMe | Cl | CH | |
| 84 | " | " | " | " | Me | Me | CH | |
| 85 | " | " | " | " | OMe | Me | N | |
| 86 | " | " | CO₂Et | " | OMe | OMe | CH | |
| 87 | " | " | CO₂n-Pr | " | OMe | OMe | CH | |
| 88 | " | " | CO₂i-Pr | " | OMe | OMe | CH | |
| 89 | Me | CO—CH₃ | CO₂Me | " | OMe | OMe | CH | 197° C. |
| 90 | " | " | " | " | OMe | OMe | N | 198–200 |
| 91 | " | " | " | " | OMe | Me | N | 191–193 |
| 92 | " | " | " | " | OMe | Me | CH | 204 |
| 93 | " | " | " | " | NMe₂ | OCH₂CF₃ | N | 115–118 |
| 94 | " | " | " | " | Me | Me | CH | 192–193 |
| 95 | " | " | " | " | Me | Me | N | |
| 96 | " | " | " | " | Cl | OMe | CH | 191–193 |
| 97 | " | " | " | Me | OMe | OMe | CH | |
| 98 | " | " | " | Me | OMe | Me | N | |
| 99 | " | " | CO₂Et | H | OMe | OMe | CH | |
| 100 | " | " | " | " | OMe | Cl | CH | |
| 101 | " | " | " | " | Me | Me | CH | |
| 102 | " | " | " | " | OMe | Me | N | |
| 103 | " | " | " | " | NMe₂ | OCH₂CF₃ | N | |
| 104 | " | " | " | Me | OMe | OMe | CH | |
| 105 | " | " | " | Me | OMe | Me | N | |
| 106 | " | " | CO₂-n-Pr | H | OMe | OMe | CH | |
| 107 | " | " | " | " | OMe | OMe | N | |
| 108 | " | " | " | " | OMe | Me | N | |
| 109 | " | " | " | " | Me | Me | CH | |
| 110 | " | " | " | " | OMe | Cl | CH | |
| 111 | " | " | " | Me | Me | OMe | N | |
| 112 | " | " | " | Me | OMe | OMe | CH | |
| 113 | Me | COCH₃ | CO₂-i-Pr | H | OMe | OMe | CH | |
| 114 | " | " | " | " | OMe | OMe | N | |
| 115 | " | " | " | " | OMe | Me | N | |
| 116 | " | " | " | " | OMe | Cl | CH | |
| 117 | " | " | " | " | Me | Me | CH | |
| 118 | " | " | " | " | SMe | NEt₂ | N | |
| 119 | " | " | CO₂-i-Pr | Me | OMe | Me | N | |
| 120 | " | " | " | Me | OMe | OMe | CH | |
| 121 | Me | COCH₃ | CO₂-Allyl | H | OMe | OMe | CH | |

TABLE 1-continued

| No. | R¹ | R² | R³ | R⁴ | X | Y | Z | m.p. |
|---|---|---|---|---|---|---|---|---|
| 122 | Et | " | CO₂Me | H | OMe | OMe | CH | 126–129 |
| 123 | " | " | " | " | OMe | Me | N | |
| 124 | " | " | " | " | Me | Me | CH | |
| 125 | " | " | " | " | Cl | OMe | CH | |
| 126 | " | " | " | Me | OMe | OMe | CH | |
| 127 | " | " | " | Me | OMe | Me | N | |
| 128 | " | " | CO₂Et | H | OMe | OMe | CH | |
| 129 | " | " | " | " | OMe | Me | CH | |
| 130 | " | " | " | " | Cl | OMe | CH | |
| 131 | " | " | " | " | OMe | Me | N | |
| 132 | " | " | " | Me | OMe | OMe | CH | |
| 133 | " | " | " | Me | OMe | Me | N | |
| 134 | " | " | CO₂-n-Pr | H | OMe | OMe | CH | |
| 135 | " | " | " | " | OMe | Me | N | |
| 136 | " | " | " | " | OMe | Cl | CH | |
| 137 | " | " | " | " | Me | Me | CH | |
| 138 | " | " | " | Me | OMe | OMe | CH | |
| 139 | " | " | " | Me | OMe | Me | N | |
| 140 | " | " | CO₂-i-Pr | H | OMe | OMe | CH | |
| 141 | " | " | " | " | OMe | Me | N | |
| 142 | " | " | " | " | Me | Me | CH | |
| 143 | " | " | " | Me | OMe | Me | N | |
| 144 | n-Pr | CO—CH₃ | CO₂Me | H | OMe | OMe | CH | 160° C. |
| 145 | " | " | " | " | OMe | Cl | CH | |
| 146 | " | " | " | " | Me | Me | CH | |
| 147 | " | " | " | " | OMe | Me | N | |
| 148 | " | " | " | Me | OMe | OMe | CH | |
| 149 | " | " | " | Me | OMe | Me | N | |
| 150 | n-Pr | " | CO₂Et | H | OMe | Me | N | |
| 151 | " | " | " | " | OMe | OMe | CH | |
| 152 | " | " | " | " | Me | Me | CH | |
| 153 | " | " | CO₂-n-Pr | " | OMe | OMe | CH | |
| 154 | i-Pr | " | CO₂Me | H | OMe | OMe | CH | |
| 155 | " | " | " | " | OMe | Me | N | |
| 156 | " | " | " | " | Me | Me | CH | |
| 157 | " | " | " | " | Cl | OMe | N | |
| 158 | " | " | " | Me | OMe | Me | N | |
| 159 | " | " | " | Me | OMe | OMe | CH | |
| 160 | Allyl | " | CO₂Me | H | OMe | OMe | CH | |
| 161 | " | " | " | " | OMe | Cl | CH | |
| 162 | " | " | " | " | Me | Me | CH | |
| 163 | " | " | " | " | OMe | Me | N | |
| 164 | " | " | CO₂Et | H | OMe | OMe | CH | |
| 165 | " | " | CO₂-n-Pr | " | OMe | OMe | CH | |
| 166 | " | " | CO₂-i-Pr | " | OMe | OMe | CH | |
| 167 | Me | COCH₂CH₃ | CO₂Me | H | OMe | OMe | CH | 186–188 |
| 168 | " | " | " | " | OMe | OMe | N | |
| 169 | " | " | " | " | SMe | Me | N | |
| 170 | " | " | " | " | OMe | Me | N | 174–176 |
| 171 | " | " | " | " | OMe | Me | CH | |
| 172 | " | " | " | " | NMe₂ | OCH₂CF₃ | N | |
| 173 | " | " | " | " | Me | Me | CH | 161–164 |
| 174 | " | " | " | " | Me | Me | N | |
| 175 | " | " | " | " | Cl | OMe | CH | 149–152 |
| 176 | " | " | " | Me | OMe | OMe | CH | |
| 177 | " | " | CO₂Me | Me | OMe | Me | N | |
| 178 | " | " | CO₂Et | H | OMe | OMe | CH | |
| 179 | " | " | " | " | OMe | Cl | CH | |
| 180 | " | " | " | " | Me | Me | CH | |
| 181 | " | " | " | " | OMe | Me | N | |
| 182 | " | " | " | " | NMe₂ | OCH₂CF₃ | N | |
| 183 | " | " | " | Me | OMe | OMe | CH | |
| 184 | " | " | " | Me | OMe | Me | N | |
| 185 | " | " | CO₂-n-Pr | H | OMe | OMe | CH | |
| 186 | " | " | " | " | OMe | OMe | N | |
| 187 | " | " | " | " | OMe | Me | N | |
| 188 | " | " | " | " | Me | Me | CH | |
| 189 | " | " | " | " | OMe | Cl | CH | |

TABLE 1-continued

| No. | R¹ | R² | R³ | R⁴ | X | Y | Z | m.p. |
|---|---|---|---|---|---|---|---|---|
| 190 | " | " | " | Me | Me | OMe | N | |
| 191 | " | " | " | " | OMe | OMe | CH | |
| 192 | Me | COCH₂CH₃ | CO₂-i-Pr | H | OMe | OMe | CH | |
| 193 | " | " | " | " | OMe | OMe | N | |
| 194 | " | " | " | " | OMe | Me | N | |
| 195 | " | " | " | " | OMe | Cl | CH | |
| 196 | " | " | " | " | Me | Me | CH | |
| 197 | " | " | " | " | SMe | NEt₂ | N | |
| 198 | " | " | " | Me | OMe | Me | N | |
| 199 | " | " | " | " | OMe | OMe | CH | |
| 200 | Me | COCH₂CH₃ | CO₂-Allyl | H | OMe | OMe | CH | |
| 201 | Et | " | CO₂-Me | H | OMe | OMe | CH | |
| 202 | " | " | " | " | OMe | Me | N | |
| 203 | " | " | " | " | Me | Me | CH | |
| 204 | " | " | " | " | Cl | OMe | CH | |
| 205 | " | " | " | Me | OMe | OMe | CH | |
| 206 | " | " | " | " | OMe | Me | N | |
| 207 | " | " | CO₂-Et | H | OMe | OMe | CH | |
| 208 | " | " | " | " | OMe | Me | CH | |
| 209 | " | " | " | " | Cl | OMe | CH | |
| 210 | " | " | " | " | OMe | Me | N | |
| 211 | " | " | " | Me | OMe | OMe | CH | |
| 212 | " | " | " | " | " | Me | N | |
| 213 | " | " | CO₂-n-Pr | H | OMe | OMe | CH | |
| 214 | " | " | " | " | OMe | Me | N | |
| 215 | " | " | " | " | OMe | Cl | CH | |
| 216 | " | " | " | " | Me | Me | CH | |
| 217 | " | " | " | Me | OMe | OMe | CH | |
| 218 | " | " | " | " | OMe | Me | N | |
| 219 | " | " | CO₂-i-Pr | H | OMe | OMe | CH | |
| 220 | " | " | " | " | OMe | Me | N | |
| 221 | " | " | " | " | Me | Me | CH | |
| 222 | " | " | " | Me | OMe | Me | N | |
| 223 | n-Pr | COCH₂CH₃ | CO₂Me | H | OMe | OMe | CH | |
| 224 | " | " | " | " | OMe | Cl | CH | |
| 225 | " | " | " | " | Me | Me | CH | |
| 226 | " | " | " | " | OMe | Me | N | |
| 227 | " | " | " | Me | OMe | OMe | CH | |
| 228 | " | " | " | Me | OMe | Me | N | |
| 229 | n-Pr | " | CO₂Et | H | OMe | Me | N | |
| 230 | " | " | " | " | OMe | OMe | CH | |
| 231 | " | " | " | " | Me | Me | CH | |
| 232 | " | " | CO₂-n-Pr | " | OMe | OMe | CH | |
| 233 | i-Pr | " | CO₂Me | H | OMe | OMe | CH | |
| 234 | " | " | " | " | OMe | Me | N | |
| 235 | " | " | " | " | Me | Me | CH | |
| 236 | " | " | " | " | Cl | OMe | N | |
| 237 | " | " | " | Me | OMe | Me | N | |
| 238 | " | " | " | Me | OMe | OMe | CH | |
| 239 | Allyl | " | CO₂Me | H | OMe | OMe | CH | |
| 240 | " | " | " | " | OMe | Cl | CH | |
| 241 | " | " | " | " | Me | Me | CH | |
| 242 | " | " | " | " | OMe | Me | N | |
| 243 | " | " | CO₂Et | H | OMe | OMe | CH | |
| 244 | " | " | CO₂-n-Pr | " | OMe | OMe | CH | |
| 245 | " | " | CO₂-i-Pr | " | OMe | OMe | CH | |
| 246 | Me | CO-n-Pr | CO₂Me | H | OMe | OMe | CH | 186–188 |
| 247 | " | " | " | " | OMe | OMe | N | |
| 248 | " | " | " | " | OMe | Me | N | |
| 249 | " | " | " | " | OMe | Me | CH | |
| 250 | " | " | " | " | NMe₂ | OCH₂CF₃ | N | |
| 251 | " | " | " | " | Me | Me | CH | |
| 252 | " | " | " | " | Me | Me | N | |
| 253 | " | " | " | " | Cl | OMe | CH | |
| 254 | " | " | " | Me | OMe | OMe | CH | |
| 255 | " | " | " | Me | OMe | Me | N | |
| 256 | " | " | CO₂Et | H | OMe | OMe | CH | |
| 257 | " | " | " | " | OMe | Cl | CH | |

TABLE 1-continued

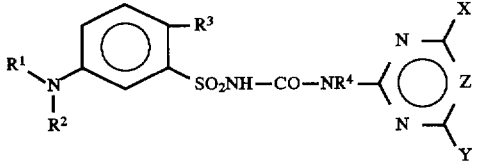

| No. | R¹ | R² | R³ | R⁴ | X | Y | Z | m.p. |
|---|---|---|---|---|---|---|---|---|
| 258 | " | " | " | " | Me | Me | CH | |
| 259 | " | " | " | " | OMe | Me | N | |
| 260 | " | " | " | " | NMe₂ | OCH₂CF₃ | N | |
| 261 | " | " | " | Me | OMe | OMe | CH | |
| 262 | " | " | " | Me | OMe | Me | N | |
| 263 | " | " | CO₂-n-Pr | H | OMe | OMe | N | |
| 264 | " | " | " | " | OMe | OMe | CH | |
| 265 | Me | CO-n-Pr | CO₂-n-Pr | H | OMe | OMe | CH | |
| 266 | " | " | " | " | OMe | OMe | N | |
| 267 | " | " | " | " | OMe | Cl | CH | |
| 268 | " | " | " | Me | Me | OMe | N | |
| 269 | " | " | " | Me | OMe | OMe | CH | |
| 270 | Me | CO-n-Pr | CO₂-i-Pr | H | OMe | OMe | CH | |
| 271 | " | " | " | " | OMe | OMe | N | |
| 272 | " | " | " | " | OMe | Me | N | |
| 273 | " | " | " | " | OMe | Cl | CH | |
| 274 | " | " | " | " | Me | Me | CH | |
| 275 | " | " | " | " | SMe | NEt₂ | N | |
| 276 | " | " | CO₂-i-Pr | Me | OMe | Me | N | |
| 277 | " | " | " | Me | OMe | OMe | CH | |
| 278 | Me | " | CO₂-Allyl | H | OMe | OMe | CH | |
| 279 | Et | " | CO₂Me | H | OMe | OMe | CH | |
| 280 | " | " | " | " | OMe | Me | N | |
| 281 | " | " | " | " | Me | Me | CH | |
| 282 | " | " | " | " | Cl | OMe | CH | |
| 283 | " | " | " | Me | OMe | OMe | CH | |
| 284 | " | " | " | Me | OMe | Me | N | |
| 285 | " | " | CO₂Et | H | OMe | OMe | CH | |
| 286 | " | " | " | " | OMe | Me | CH | |
| 287 | " | " | " | " | Cl | OMe | CH | |
| 288 | " | " | " | " | OMe | Me | N | |
| 289 | " | " | " | Me | OMe | OMe | CH | |
| 290 | " | " | " | Me | OMe | Me | N | |
| 291 | " | " | CO₂-n-Pr | H | OMe | OMe | CH | |
| 292 | " | " | " | " | OMe | Me | N | |
| 293 | " | " | " | " | OMe | Cl | CH | |
| 294 | " | " | " | " | Me | Me | CH | |
| 295 | " | " | " | Me | OMe | OMe | CH | |
| 296 | " | " | " | Me | OMe | Me | N | |
| 297 | " | " | CO₂-i-Pr | H | OMe | OMe | CH | |
| 298 | " | " | " | " | OMe | Me | N | |
| 299 | n-Pr | CO-n-Pr | CO₂-Me | H | OMe | OMe | CH | |
| 300 | " | " | " | " | OMe | Cl | CH | |
| 301 | " | " | " | " | Me | Me | CH | |
| 302 | " | " | " | " | OMe | Me | N | |
| 303 | " | " | " | Me | OMe | OMe | CH | |
| 304 | " | " | " | Me | OMe | Me | N | |
| 305 | n-Pr | " | CO₂Et | H | OMe | Me | N | |
| 306 | " | " | " | " | OMe | OMe | CH | |
| 307 | " | " | " | " | Me | Me | CH | |
| 308 | " | " | CO₂-n-Pr | " | OMe | OMe | CH | |
| 309 | i-Pr | " | CO₂Me | H | OMe | OMe | CH | |
| 310 | " | " | " | " | OMe | Me | N | |
| 311 | " | " | " | " | Me | Me | CH | |
| 312 | " | " | " | " | Cl | OMe | N | |
| 313 | " | " | " | Me | OMe | Me | N | |
| 314 | " | " | " | Me | OMe | OMe | CH | |
| 315 | Allyl | " | CO₂-Me | H | OMe | OMe | CH | |
| 316 | " | " | " | " | OMe | Cl | CH | |
| 317 | " | " | " | " | Me | Me | CH | |
| 318 | " | " | " | " | OMe | Me | N | |
| 319 | " | " | CO₂Et | H | OMe | OMe | CH | |
| 320 | " | " | CO₂-n-Pr | " | OMe | OMe | CH | |
| 321 | " | " | CO₂-i-Pr | " | OMe | OMe | CH | |
| 322 | Me | CO-i-Pr | CO₂-Me | H | OMe | OMe | CH | 150 |
| 323 | " | " | " | " | OMe | OMe | N | |
| 324 | " | " | " | " | " | Me | N | 165–167 |
| 325 | " | " | " | " | " | " | CH | 185–187 |

TABLE 1-continued

| No. | R¹ | R² | R³ | R⁴ | X | Y | Z | m.p. |
|---|---|---|---|---|---|---|---|---|
| 326 | " | " | " | " | NMe₂ | OCH₂CF₃ | N | |
| 327 | " | " | " | " | Me | Me | CH | 105–110 |
| 328 | " | " | " | " | Me | Me | N | |
| 329 | " | " | " | " | Cl | OMe | CH | |
| 330 | " | " | " | Me | OMe | OMe | CH | |
| 331 | " | " | " | " | " | Me | N | |
| 332 | " | " | CO₂-Et | H | OMe | OMe | CH | |
| 333 | " | " | " | " | " | Cl | CH | |
| 334 | " | " | " | " | Me | Me | CH | |
| 335 | " | " | " | " | OMe | Me | N | |
| 336 | " | " | " | " | NMe₂ | OCH₂CF₃ | N | |
| 337 | " | " | " | Me | OMe | OMe | CH | |
| 338 | " | " | " | " | OMe | Me | N | |
| 339 | " | " | CO₂-n-Pr | H | OMe | OMe | CH | |
| 340 | " | " | " | " | " | " | N | |
| 341 | " | " | " | " | OMe | Me | N | |
| 342 | " | " | " | " | Me | Me | CH | |
| 343 | " | " | " | " | OMe | Cl | CH | |
| 344 | " | " | " | Me | Me | OMe | N | |
| 345 | " | " | " | " | OMe | OMe | CH | |
| 346 | Me | CO-i-Pr | CO₂-i-Pr | H | OMe | OMe | CH | |
| 347 | " | " | " | " | " | " | N | |
| 348 | " | " | " | " | OMe | Me | N | |
| 349 | " | " | " | " | OMe | Cl | CH | |
| 350 | " | " | " | " | Me | Me | CH | |
| 351 | " | " | " | " | SMe | NEt₂ | N | |
| 352 | " | " | CO₂-i-Pr | Me | OMe | Me | N | |
| 353 | " | " | " | " | OMe | OMe | CH | |
| 354 | Me | COCHMe₂ | CH₂CHCH₂ | H | OMe | OMe | CH | |
| 355 | Et | " | CO₂-Me | H | OMe | OMe | CH | |
| 356 | " | " | " | H | OMe | Me | N | |
| 357 | " | " | " | " | Me | Me | CH | |
| 358 | " | " | " | " | Cl | OMe | CH | |
| 359 | " | " | " | Me | OMe | OMe | CH | |
| 360 | " | " | " | " | OMe | Me | N | |
| 361 | " | " | CO₂-Et | H | OMe | OMe | CH | |
| 362 | " | " | " | " | OMe | Me | CH | |
| 363 | " | " | " | " | Cl | OMe | CH | |
| 364 | " | " | " | " | OMe | Me | N | |
| 365 | " | " | " | Me | OMe | OMe | CH | |
| 366 | " | " | " | " | " | Me | N | |
| 367 | " | " | CO₂-n-Pr | H | OMe | OMe | CH | |
| 368 | " | " | " | " | OMe | Me | N | |
| 369 | " | " | " | " | OMe | Cl | CH | |
| 370 | " | " | " | " | Me | Me | CH | |
| 371 | " | " | " | Me | OMe | OMe | CH | |
| 372 | " | " | " | " | OMe | Me | N | |
| 373 | " | " | CO₂-i-Pr | H | OMe | OMe | CH | |
| 374 | " | " | " | " | OMe | Me | N | |
| 375 | " | " | " | " | Me | Me | CH | |
| 376 | " | " | " | Me | OMe | Me | N | |
| 377 | n-Pr | CO-i-Pr | CO₂-Me | H | OMe | OMe | CH | |
| 378 | " | " | " | " | " | Cl | CH | |
| 379 | " | " | " | " | Me | Me | CH | |
| 380 | " | " | " | " | OMe | Me | N | |
| 381 | " | " | " | Me | OMe | OMe | CH | |
| 382 | " | " | " | " | OMe | Me | N | |
| 383 | n-Pr | " | CO₂-Et | H | " | Me | N | |
| 384 | " | " | " | " | " | OMe | CH | |
| 385 | " | " | " | " | Me | Me | CH | |
| 386 | " | " | CO₂-n-Pr | " | OMe | OMe | CH | |
| 387 | i-Pr | " | CO₂-Me | H | OMe | OMe | CH | |
| 388 | " | " | " | " | OMe | Me | N | |
| 389 | " | " | " | " | Me | Me | CH | |
| 390 | " | " | " | " | Cl | OMe | N | |
| 391 | " | " | " | Me | OMe | Me | N | |
| 392 | " | " | " | " | " | OMe | CH | |
| 393 | Allyl | " | CO₂-Me | H | OMe | OMe | CH | |

TABLE 1-continued

| No. | R¹ | R² | R³ | R⁴ | X | Y | Z | m.p. |
|---|---|---|---|---|---|---|---|---|
| 394 | " | " | " | " | " | Cl | CH | |
| 395 | " | " | " | " | Me | Me | CH | |
| 396 | " | " | " | " | OMe | Me | N | |
| 397 | " | " | $CO_2$-Et | H | OMe | OMe | CH | |
| 398 | " | " | $CO_2$-n-Pr | " | OMe | OMe | CH | |
| 399 | " | " | $CO_2$-i-Pr | " | " | " | " | |
| 400 | Me | CO-t-Bu | $CO_2$-Me | H | OMe | OMe | CH | |
| 401 | " | " | " | " | " | OMe | N | |
| 402 | " | " | " | " | " | Me | N | |
| 403 | " | " | " | " | " | " | CH | |
| 404 | " | " | " | " | $NMe_2$ | $OCH_2CF_3$ | N | |
| 405 | " | " | " | " | Me | Me | CH | |
| 406 | " | " | " | " | " | " | N | |
| 407 | " | " | " | " | Cl | OMe | CH | |
| 408 | " | " | " | Me | OMe | OMe | CH | |
| 409 | " | " | " | " | " | Me | N | |
| 410 | " | " | $CO_2$-Et | H | OMe | OMe | CH | |
| 411 | " | " | " | " | " | Cl | CH | |
| 412 | " | " | " | " | Me | Me | CH | |
| 413 | " | " | " | " | OMe | Me | N | |
| 414 | " | " | " | " | $NMe_2$ | $OCH_2CF_3$ | N | |
| 415 | " | " | " | Me | OMe | OMe | CH | |
| 416 | " | " | " | " | OMe | Me | N | |
| 417 | " | " | $CO_2$-n-Pr | H | OMe | OMe | CH | |
| 418 | " | " | " | " | " | " | N | |
| 419 | " | " | " | " | OMe | Me | N | |
| 420 | " | " | " | " | Me | Me | CH | |
| 421 | " | " | " | " | OMe | Cl | CH | |
| 422 | " | " | " | Me | Me | OMe | N | |
| 423 | " | " | " | " | OMe | OMe | CH | |
| 424 | Me | CO-t-Bu | $CO_2$-i-Pr | H | OMe | OMe | CH | |
| 425 | " | " | " | " | " | " | N | |
| 426 | " | " | " | " | H | Me | N | |
| 427 | " | " | " | " | OMe | Cl | CH | |
| 428 | " | " | " | " | Me | Me | CH | |
| 429 | " | " | " | " | SMe | $NEt_2$ | N | |
| 430 | " | " | $CO_2$-i-Pr | Me | OMe | Me | N | |
| 431 | " | " | " | Et | OMe | OMe | CH | |
| 432 | Me | " | $CO_2$-Allyl | H | OMe | OMe | CH | |
| 433 | Et | " | $CO_2$-Me | H | OMe | OMe | CH | |
| 434 | " | " | " | H | OMe | Me | N | |
| 435 | " | " | " | " | Me | Me | CH | |
| 436 | " | " | " | " | Cl | OMe | CH | |
| 437 | " | " | " | Me | OMe | OMe | CH | |
| 438 | " | " | " | " | OMe | Me | N | |
| 439 | " | " | $CO_2$-Et | H | OMe | OMe | CH | |
| 440 | " | " | " | " | OMe | Me | CH | |
| 441 | " | " | " | " | Cl | OMe | CH | |
| 442 | " | " | " | " | OMe | Me | N | |
| 443 | " | " | " | Me | OMe | OMe | CH | |
| 444 | " | " | " | " | " | Me | N | |
| 445 | " | " | $CO_2$-n-Pr | H | OMe | OMe | CH | |
| 446 | " | " | " | " | OMe | Me | N | |
| 447 | " | " | " | " | OMe | Cl | CH | |
| 448 | " | " | " | " | Me | Me | CH | |
| 449 | " | " | " | Me | OMe | OMe | CH | |
| 450 | " | " | " | " | OMe | Me | N | |
| 451 | " | " | $CO_2$-iPr | H | OMe | OMe | CH | |
| 452 | " | " | " | " | OMe | Me | N | |
| 453 | " | " | " | " | Me | Me | CH | |
| 454 | " | " | " | Me | OMe | Me | N | |
| 455 | n-Pr | CO-t-Bu | $CO_2$-Me | H | OMe | OMe | CH | |
| 456 | " | " | " | " | OMe | Cl | CH | |
| 457 | " | " | " | " | Me | Me | CH | |
| 458 | " | " | " | " | OMe | Me | N | |
| 459 | " | " | " | Me | OMe | OMe | CH | |
| 460 | n-Pr | " | $CO_2$-Et | Me | OMe | Me | N | |
| 461 | n-Pr | " | $CO_2$-Et | H | OMe | Me | N | |

TABLE 1-continued

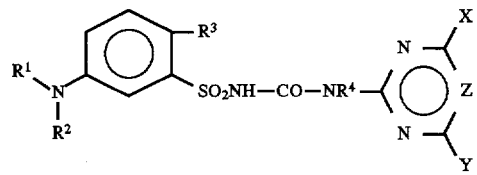

| No. | R¹ | R² | R³ | R⁴ | X | Y | Z | m.p. |
|---|---|---|---|---|---|---|---|---|
| 462 | " | " | " | " | OMe | OMe | CH | |
| 463 | " | " | " | " | Me | Me | CH | |
| 464 | i-Pr | " | CO₂-Me | " | OMe | OMe | CH | |
| 465 | i-Pr | " | " | Me | OMe | OMe | CH | |
| 466 | " | " | " | H | OMe | Me | N | |
| 467 | " | " | " | " | Me | Me | CH | |
| 468 | " | " | " | " | Cl | OMe | N | |
| 469 | " | " | " | Me | OMe | Me | N | |
| 470 | Allyl | " | " | H | OMe | OMe | CH | |
| 471 | " | " | " | H | OMe | Cl | CH | |
| 472 | " | " | " | " | OMe | Me | N | |
| 473 | " | " | " | " | Me | Me | CH | |
| 474 | " | " | CO₂-Et | H | OMe | OMe | CH | |
| 475 | " | " | CO₂-n-Pr | H | OMe | OMe | CH | |
| 476 | " | " | CO₂-i-Pr | H | OMe | OMe | CH | |
| 477 | Me | CO-c-Propyl | CO₂-Me | H | OMe | OMe | CH | 161° C |
| 478 | " | " | " | " | " | OMe | N | |
| 479 | " | " | " | " | " | Me | N | |
| 480 | " | " | " | " | " | " | CH | |
| 481 | " | " | " | " | NMe₂ | OCH₂CF₃ | N | |
| 482 | " | " | " | " | Me | Me | CH | |
| 483 | " | " | " | " | " | " | N | |
| 484 | " | " | " | " | Cl | OMe | CH | |
| 485 | " | " | " | Me | OMe | OMe | CH | |
| 486 | " | " | " | " | " | Me | N | |
| 487 | " | " | CO₂-Et | H | OMe | OMe | CH | |
| 488 | " | " | " | " | " | Cl | CH | |
| 489 | " | " | " | " | Me | Me | CH | |
| 490 | " | " | " | " | OMe | Me | N | |
| 491 | " | " | " | " | NMe₂ | OCH₂CF₃ | N | |
| 492 | " | " | " | Me | OMe | OMe | CH | |
| 493 | " | " | " | " | OMe | Me | N | |
| 494 | " | " | CO₂-n-Pr | H | OMe | OMe | CH | |
| 495 | " | " | " | " | " | " | N | |
| 496 | " | " | " | " | OMe | Me | N | |
| 497 | " | " | " | " | Me | Me | CH | |
| 498 | " | " | " | " | OMe | Cl | CH | |
| 499 | " | " | " | Me | Me | OMe | N | |
| 500 | " | " | " | " | OMe | OMe | CH | |
| 501 | Me | CO-c-Propyl | CO₂-i-Pr | H | OMe | OMe | CH | |
| 502 | " | " | " | " | " | " | N | |
| 503 | " | " | " | " | OMe | Me | N | |
| 504 | " | " | " | " | OMe | Cl | CH | |
| 505 | " | " | " | " | Me | Me | CH | |
| 506 | " | " | " | " | SMe | NEt₂ | N | |
| 507 | " | " | CO₂-i-Pr | Me | OMe | Me | N | |
| 508 | " | " | " | " | OMe | OMe | CH | |
| 509 | Me | " | CO₂-Allyl | H | OMe | OMe | CH | |
| 510 | Et | " | CO₂-Me | H | OMe | OMe | CH | |
| 511 | " | " | " | H | OMe | Me | N | |
| 512 | " | " | " | " | Me | Me | CH | |
| 513 | " | " | " | " | Cl | OMe | CH | |
| 514 | " | " | " | Me | OMe | OMe | CH | |
| 515 | " | " | " | " | OMe | Me | N | |
| 516 | " | " | CO₂-Et | H | OMe | OMe | CH | |
| 517 | " | " | " | " | Me | Me | CH | |
| 518 | " | " | " | " | Cl | OMe | CH | |
| 519 | " | " | " | " | OMe | Me | N | |
| 520 | " | " | " | Me | OMe | OMe | CH | |
| 521 | " | " | " | " | " | Me | N | |
| 522 | " | " | CO₂-n-Pr | H | OMe | OMe | CH | |
| 523 | " | " | " | " | OMe | Me | N | |
| 524 | " | " | " | " | OMe | Cl | CH | |
| 525 | " | " | " | " | Me | Me | CH | |
| 526 | " | " | " | Me | OMe | OMe | CH | |
| 527 | " | " | " | " | OMe | Me | N | |
| 528 | " | " | CO₂-i-Pr | H | OMe | OMe | CH | |
| 529 | " | " | " | " | OMe | Me | N | |

TABLE 1-continued

| No. | R¹ | R² | R³ | R⁴ | X | Y | Z | m.p. |
|---|---|---|---|---|---|---|---|---|
| 530 | " | " | " | " | Me | Me | CH | |
| 531 | " | " | " | Me | OMe | Me | N | |
| 532 | n-Pr | CO-c-Propyl | $CO_2$-Me | H | OMe | OMe | CH | |
| 533 | " | " | " | " | " | Cl | CH | |
| 534 | " | " | " | " | Me | Me | CH | |
| 535 | " | " | " | " | OMe | Me | N | |
| 536 | " | " | " | Me | OMe | OMe | CH | |
| 537 | " | " | " | " | OMe | Me | N | |
| 538 | n-Pr | " | $CO_2$-Et | H | " | " | N | |
| 539 | " | " | " | " | " | OMe | CH | |
| 540 | " | " | " | " | Me | Me | CH | |
| 541 | " | " | $CO_2$-n-Pr | " | OMe | OMe | CH | |
| 542 | i-Pr | " | $CO_2$-Me | H | OMe | OMe | CH | |
| 543 | " | " | " | " | OMe | Me | N | |
| 544 | " | " | " | " | Me | Me | CH | |
| 545 | " | " | " | " | Cl | OMe | N | |
| 546 | " | " | " | Me | OMe | Me | N | |
| 547 | " | " | " | " | " | OMe | CH | |
| 548 | Allyl | " | $CO_2$-Me | H | OMe | OMe | CH | |
| 549 | " | " | " | " | " | Cl | CH | |
| 550 | " | " | " | " | Me | Me | CH | |
| 551 | " | " | " | " | OMe | Me | N | |
| 552 | " | " | $CO_2$-Et | H | OMe | OMe | CH | |
| 553 | " | " | $CO_2$-n-Pr | H | OMe | OMe | CH | |
| 554 | " | " | $CO_2$-i-Pr | H | OMe | OMe | CH | |
| 555 | Me | CO-n-$C_5H_{11}$ | $CO_2$-Me | H | OMe | OMe | CH | 191–192 |
| 556 | " | " | " | " | OMe | OMe | N | |
| 557 | " | " | " | " | " | Me | N | |
| 558 | " | " | " | " | " | " | CH | |
| 559 | " | " | " | " | $NMe_2$ | $OCH_2CF_3$ | N | |
| 560 | " | " | " | " | Me | Me | CH | |
| 561 | " | " | " | " | " | " | N | |
| 562 | " | " | " | " | Cl | OMe | CH | |
| 563 | " | " | " | Me | OMe | OMe | CH | |
| 564 | " | " | " | " | " | Me | N | |
| 565 | " | " | $CO_2$-Et | H | OMe | OMe | CH | |
| 566 | " | " | " | " | " | Cl | CH | |
| 567 | " | " | " | " | Me | Me | CH | |
| 568 | " | " | " | " | OMe | Me | N | |
| 569 | " | " | " | " | $NMe_2$ | $OCH_2CF_3$ | N | |
| 570 | " | " | " | Me | OMe | OMe | CH | |
| 571 | " | " | " | " | OMe | Me | N | |
| 572 | " | " | $CO_2$-n-Pr | H | OMe | OMe | CH | |
| 573 | " | " | " | " | " | " | N | |
| 574 | " | " | " | " | OMe | Me | N | |
| 575 | " | " | " | " | Me | Me | CH | |
| 576 | " | " | " | " | OMe | Cl | CH | |
| 577 | " | " | " | Me | Me | OMe | N | |
| 578 | " | " | " | " | OMe | OMe | CH | |
| 579 | Me | CO-n-$C_5H_{11}$ | $CO_2$-i-Pr | H | OMe | OMe | CH | |
| 580 | " | " | " | " | " | " | N | |
| 581 | " | " | " | " | H | Me | N | |
| 582 | " | " | " | " | OMe | Cl | CH | |
| 583 | " | " | " | " | Me | Me | CH | |
| 584 | " | " | " | " | SMe | $NEt_2$ | N | |
| 585 | " | " | $CO_2$-i-Pr | Me | OMe | Me | N | |
| 586 | " | " | " | " | OMe | OMe | CH | |
| 587 | Me | " | $CO_2$-Allyl | H | OMe | OMe | CH | |
| 588 | Et | " | $CO_2$-Me | H | OMe | OMe | CH | |
| 589 | " | " | " | H | OMe | Me | N | |
| 590 | " | " | " | " | Me | Me | CH | |
| 591 | " | " | " | " | Cl | OMe | CH | |
| 592 | " | " | " | Me | OMe | OMe | CH | |
| 593 | " | " | " | " | OMe | Me | N | |
| 594 | " | " | $CO_2$-Et | H | OMe | OMe | CH | |
| 595 | " | " | " | " | OMe | Me | CH | |
| 596 | " | " | " | " | Cl | OMe | CH | |
| 597 | " | " | " | " | OMe | Me | N | |

TABLE 1-continued

| No. | R¹ | R² | R³ | R⁴ | X | Y | Z | m.p. |
|---|---|---|---|---|---|---|---|---|
| 598 | " | " | " | Me | OMe | OMe | CH | |
| 599 | " | " | " | " | " | Me | N | |
| 600 | " | " | CO₂-n-Pr | H | OMe | OMe | CH | |
| 601 | " | " | " | " | OMe | Me | N | |
| 602 | " | " | " | " | OMe | Cl | CH | |
| 603 | " | " | " | " | Me | Me | CH | |
| 604 | " | " | " | Me | OMe | OMe | CH | |
| 605 | " | " | " | " | OMe | Me | N | |
| 606 | " | " | CO₂-i-Pr | H | OMe | OMe | CH | |
| 607 | " | " | " | " | OMe | Me | N | |
| 608 | " | " | " | " | Me | Me | CH | |
| 609 | " | " | " | Me | OMe | Me | N | |
| 610 | n-Pr | CO-n-C₅H₁₁ | CO₂-Me | H | OMe | OMe | CH | |
| 611 | " | " | " | " | " | Cl | CH | |
| 612 | " | " | " | " | Me | Me | CH | |
| 613 | " | " | " | " | OMe | Me | N | |
| 614 | " | " | " | Me | OMe | OMe | CH | |
| 615 | " | " | " | " | OMe | Me | N | |
| 616 | n-Pr | " | CO₂-Et | H | OMe | Me | N | |
| 617 | " | " | " | " | " | OMe | CH | |
| 618 | " | " | " | " | Me | Me | CH | |
| 619 | " | " | CO₂-n-Pr | " | OMe | OMe | CH | |
| 620 | i-Pr | " | CO₂-Me | H | OMe | OMe | CH | |
| 621 | " | " | " | " | OMe | Me | N | |
| 622 | " | " | " | " | Me | Me | CH | |
| 623 | " | " | " | " | Cl | OMe | N | |
| 624 | " | " | " | " | Me | OMe | N | |
| 625 | " | " | " | " | " | OMe | CH | |
| 626 | Allyl | " | CO₂-Me | H | OMe | OMe | CH | |
| 627 | " | " | " | " | " | Cl | CH | |
| 628 | " | " | " | " | Me | Me | CH | |
| 629 | " | " | " | " | OMe | Me | N | |
| 630 | " | " | CO₂-Et | H | OMe | OMe | CH | |
| 631 | " | " | CO₂-n-Pr | " | " | " | CH | |
| 632 | " | " | CO₂-i-Pr | " | " | " | " | |
| 633 | Me | CO-CHMeEt | CO₂-Me | H | " | OMe | CH | |
| 634 | " | " | " | " | " | OMe | N | |
| 635 | " | " | " | " | " | Me | N | |
| 636 | " | " | " | " | " | " | CH | |
| 637 | " | " | " | " | NMe₂ | OCH₂CF₃ | N | |
| 638 | " | " | " | " | Me | Me | CH | |
| 639 | " | " | " | " | " | " | N | |
| 640 | " | " | " | " | Cl | OMe | CH | |
| 641 | " | " | " | Me | OMe | OMe | CH | |
| 642 | " | " | " | " | " | Me | N | |
| 643 | " | " | CO₂-Et | H | OMe | OMe | CH | |
| 644 | " | " | " | " | " | Cl | CH | |
| 645 | " | " | " | " | Me | Me | CH | |
| 646 | " | " | " | " | OMe | Me | N | |
| 647 | " | " | " | " | NMe₂ | OCH₂CF₃ | N | |
| 648 | " | " | " | Me | OMe | OMe | CH | |
| 649 | " | " | " | " | OMe | Me | N | |
| 650 | " | " | CO₂-n-Pr | H | OMe | OMe | CH | |
| 651 | " | " | " | " | " | " | N | |
| 652 | " | " | " | " | OMe | Me | N | |
| 653 | " | " | " | " | Me | Me | CH | |
| 654 | " | " | " | " | OMe | Cl | CH | |
| 655 | " | " | " | Me | Me | OMe | N | |
| 656 | " | " | " | " | OMe | OMe | CH | |
| 657 | Me | COCHMeEt | CO₂-i-Pr | H | OMe | OMe | CH | |
| 658 | " | " | " | " | " | " | N | |
| 659 | " | " | " | " | OMe | Me | N | |
| 660 | " | " | " | " | OMe | Cl | CH | |
| 661 | " | " | " | " | Me | Me | CH | |
| 662 | " | " | " | " | SMe | NEt₂ | N | |
| 663 | " | " | CO₂-i-Pr | Me | OMe | Me | N | |
| 664 | " | " | " | " | OMe | OMe | CH | |
| 665 | Me | " | CO₂-Allyl | H | OMe | OMe | CH | |

TABLE 1-continued

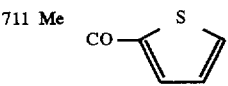

| No. | R¹ | R² | R³ | R⁴ | X | Y | Z | m.p. |
|---|---|---|---|---|---|---|---|---|
| 666 | Et | " | CO₂-Me | H | OMe | OMe | CH | |
| 667 | " | " | " | H | OMe | Me | N | |
| 668 | " | " | " | " | Me | Me | CH | |
| 669 | " | " | " | " | Cl | OMe | CH | |
| 670 | " | " | " | Me | OMe | OMe | CH | |
| 671 | " | " | " | " | OMe | Me | N | |
| 672 | " | " | CO₂-Et | H | OMe | OMe | CH | |
| 673 | " | " | " | " | OMe | Me | CH | |
| 674 | " | " | " | " | Cl | OMe | CH | |
| 675 | " | " | " | " | OMe | Me | N | |
| 676 | " | " | " | Me | OMe | OMe | CH | |
| 677 | " | " | " | " | " | Me | N | |
| 678 | " | " | CO₂-n-Pr | H | OMe | OMe | CH | |
| 679 | " | " | " | " | OMe | Me | N | |
| 680 | " | " | " | " | OMe | Cl | CH | |
| 681 | " | " | " | " | Me | Me | CH | |
| 682 | " | " | " | Me | OMe | OMe | CH | |
| 683 | " | " | " | " | OMe | Me | N | |
| 684 | " | " | CO₂-i-Pr | H | OMe | OMe | CH | |
| 685 | " | " | " | " | OMe | Me | N | |
| 686 | " | " | " | " | Me | Me | CH | |
| 687 | " | " | " | Me | OMe | Me | N | |
| 688 | n-Pr | CO—CHMeEt | CO₂-Me | H | OMe | OMe | CH | |
| 689 | " | " | " | " | " | Cl | CH | |
| 690 | " | " | " | " | Me | Me | CH | |
| 691 | " | " | " | " | OMe | Me | N | |
| 692 | " | " | " | Me | OMe | OMe | CH | |
| 693 | " | " | " | " | OMe | Me | N | |
| 694 | n-Pr | " | CO₂-Et | H | " | " | N | |
| 695 | " | " | " | " | " | OMe | CH | |
| 696 | " | " | " | " | Me | Me | CH | |
| 697 | " | " | CO₂-n-Pr | " | OMe | OMe | CH | |
| 698 | i-Pr | " | CO₂-Me | H | OMe | OMe | CH | |
| 699 | " | " | " | " | OMe | Me | N | |
| 700 | " | " | " | " | Me | Me | CH | |
| 701 | " | " | " | " | Cl | OMe | N | |
| 702 | " | " | " | Me | OMe | Me | N | |
| 703 | " | " | " | " | " | OMe | CH | |
| 704 | Allyl | " | CO₂-Me | H | OMe | OMe | CH | |
| 705 | " | " | " | " | " | Cl | CH | |
| 706 | " | " | " | " | Me | Me | CH | |
| 707 | " | " | " | " | OMe | Me | N | |
| 708 | " | " | CO₂-Et | H | OMe | OMe | CH | |
| 709 | " | " | CO₂-n-Pr | " | " | " | CH | |
| 710 | " | " | CO₂-i-Pr | " | " | " | CH | |
| 711 | Me | CO-[2-thienyl] | CO₂-Me | H | OMe | OMe | CH | |
| 712 | " | " | " | " | OMe | OMe | N | |
| 713 | " | " | " | " | " | Me | N | |
| 714 | " | " | " | " | " | " | CH | |
| 715 | " | " | " | " | NMe₂ | OCH₂CF₃ | N | |
| 716 | " | " | " | " | Me | Me | CH | |
| 717 | " | " | " | " | " | " | N | |
| 718 | " | " | " | " | Cl | OMe | CH | |
| 719 | " | " | " | Me | OMe | OMe | CH | |
| 720 | " | " | " | " | " | Me | N | |
| 721 | " | " | CO₂-Et | H | OMe | OMe | CH | |
| 722 | " | " | " | " | " | Cl | CH | |
| 723 | " | " | " | " | Me | Me | CH | |
| 724 | " | " | " | " | OMe | Me | N | |
| 725 | " | " | " | " | NMe₂ | OCH₂CF₃ | N | |
| 726 | " | " | " | Me | OMe | OMe | CH | |
| 727 | " | " | " | " | OMe | Me | N | |
| 728 | " | " | CO₂-n-Pr | H | OMe | OMe | CH | |

TABLE 1-continued

| No. | R¹ | R² | R³ | R⁴ | X | Y | Z | m.p. |
|---|---|---|---|---|---|---|---|---|
| 729 | " | " | " | " | " | " | N | |
| 730 | " | " | " | " | OMe | Me | N | |
| 731 | " | " | " | " | Me | Me | CH | |
| 732 | " | " | " | " | OMe | Cl | CH | |
| 733 | " | " | " | Me | Me | OMe | N | |
| 734 | " | " | " | " | OMe | OMe | CH | |
| 735 | Me | S-CO (thiophene) | $CO_2$-i-Pr | H | OMe | OMe | CH | |
| 736 | " | " | " | " | " | " | N | |
| 737 | " | " | " | " | OMe | Me | N | |
| 738 | " | " | " | " | OMe | Cl | CH | |
| 739 | " | " | " | " | Me | Me | CH | |
| 740 | " | " | " | " | SMe | $NEt_2$ | N | |
| 741 | " | " | $CO_2$-i-Pr | Me | OMe | Me | N | |
| 742 | " | " | " | " | OMe | OMe | CH | |
| 743 | Me | " | $CO_2$-Allyl | H | OMe | OMe | CH | |
| 744 | Et | " | $CO_2$-Me | H | OMe | OMe | CH | |
| 745 | " | " | " | H | OMe | Me | N | |
| 746 | " | " | " | " | Me | Me | CH | |
| 747 | " | " | " | " | Cl | OMe | CH | |
| 748 | " | " | " | Me | OMe | OMe | CH | |
| 749 | " | " | " | " | OMe | Me | N | |
| 750 | " | " | $CO_2$-Et | H | OMe | OMe | CH | |
| 751 | " | " | " | " | OMe | Me | CH | |
| 752 | " | " | " | " | Cl | OMe | CH | |
| 753 | " | " | " | " | OMe | Me | N | |
| 754 | " | " | " | Me | OMe | OMe | CH | |
| 755 | " | " | " | " | " | Me | N | |
| 756 | " | " | $CO_2$-n-Pr | H | OMe | OMe | CH | |
| 757 | " | " | " | " | OMe | Me | N | |
| 758 | " | " | " | " | OMe | Cl | CH | |
| 759 | " | " | " | " | Me | Me | CH | |
| 760 | " | " | " | Me | OMe | OMe | CH | |
| 761 | " | " | " | " | OMe | Me | N | |
| 762 | " | " | $CO_2$-i-Pr | H | OMe | OMe | CH | |
| 763 | " | " | " | " | OMe | Me | N | |
| 764 | " | " | " | " | Me | Me | CH | |
| 765 | " | " | " | Me | OMe | Me | N | |
| 766 | n-Pr | S-CO (thiophene) | $CO_2$-Me | H | OMe | OMe | CH | |
| 767 | " | " | " | " | " | Cl | CH | |
| 768 | " | " | " | " | Me | Me | CH | |
| 769 | " | " | " | " | OMe | Me | N | |
| 770 | " | " | " | Me | OMe | OMe | CH | |
| 771 | " | " | " | " | OMe | Me | N | |
| 772 | n-Pr | " | $CO_2$-Et | H | OMe | OMe | N | |
| 773 | " | " | " | " | " | OMe | CH | |
| 774 | " | " | " | " | Me | Me | CH | |
| 775 | " | " | $CO_2$-n-Pr | " | OMe | OMe | CH | |
| 776 | i-Pr | " | $CO_2$-Me | H | OMe | OMe | CH | |
| 777 | " | " | " | " | OMe | Me | N | |
| 778 | " | " | " | " | Me | Me | CH | |
| 779 | " | " | " | " | Cl | OMe | N | |
| 780 | " | " | " | Me | OMe | Me | N | |
| 781 | " | " | " | " | " | OMe | CH | |
| 782 | Allyl | " | $CO_2$Me | H | OMe | OMe | CH | |
| 783 | " | " | " | " | " | Cl | CH | |
| 784 | " | " | " | " | Me | Me | CH | |
| 785 | " | " | " | " | OMe | Me | N | |
| 786 | " | " | $CO_2$-Et | H | OMe | OMe | CH | |

TABLE 1-continued

| No. | R¹ | R² | R³ | R⁴ | X | Y | Z | m.p. |
|---|---|---|---|---|---|---|---|---|
| 787 | " | " | CO$_2$-n-Pr | " | " | " | " | |
| 788 | " | " | CO$_2$-i-Pr | " | " | " | " | |
| 789 | Me | CO-[thiophene-Cl] | CO$_2$Me | H | OMe | OMe | CH | |
| 790 | " | " | " | " | " | OMe | N | |
| 791 | " | " | " | " | " | Me | N | |
| 792 | " | " | " | " | " | " | CH | |
| 793 | " | " | " | " | NMe$_2$ | OCH$_2$CF$_3$ | N | |
| 794 | " | " | " | " | Me | Me | CH | |
| 795 | " | " | " | " | " | " | N | |
| 796 | " | " | " | " | Cl | OMe | CH | |
| 797 | " | " | " | Me | OMe | OMe | CH | |
| 798 | " | " | " | " | " | Me | N | |
| 799 | " | " | CO$_2$-Et | H | OMe | OMe | CH | |
| 800 | " | " | " | " | " | Cl | CH | |
| 801 | " | " | " | " | Me | Me | CH | |
| 802 | " | " | " | " | OMe | Me | N | |
| 803 | " | " | " | " | NMe$_2$ | OCH$_2$CF$_3$ | N | |
| 804 | " | " | " | Me | OMe | OMe | CH | |
| 805 | " | " | " | " | OMe | Me | N | |
| 806 | " | " | CO$_2$-n-Pr | H | OMe | OMe | CH | |
| 807 | " | " | " | " | " | " | N | |
| 808 | " | " | " | " | OMe | Me | N | |
| 809 | " | " | " | " | Me | Me | CH | |
| 810 | " | " | " | " | OMe | Cl | CH | |
| 811 | " | " | " | Me | Me | OMe | N | |
| 812 | " | " | " | " | OMe | OMe | CH | |
| 813 | Me | " | CO$_2$-i-Pr | H | OMe | OMe | CH | |
| 814 | " | " | " | " | " | " | N | |
| 815 | " | " | " | " | OMe | Me | N | |
| 816 | " | " | " | " | OMe | Cl | CH | |
| 817 | " | " | " | " | Me | Me | CH | |
| 818 | " | " | " | " | SMe | NEt$_2$ | N | |
| 819 | " | " | CO$_2$-i-Pr | Me | OMe | Me | N | |
| 820 | " | " | " | " | OMe | OMe | CH | |
| 821 | Me | " | CO$_2$-Allyl | H | OMe | OMe | CH | |
| 822 | Et | " | CO$_2$-Me | H | OMe | OMe | CH | |
| 823 | " | " | " | H | OMe | Me | N | |
| 824 | " | " | " | " | Me | Me | CH | |
| 825 | " | " | " | " | Cl | OMe | CH | |
| 826 | " | " | " | Me | OMe | OMe | CH | |
| 827 | " | " | " | " | OMe | Me | N | |
| 828 | " | " | CO$_2$-Et | H | OMe | OMe | CH | |
| 829 | " | " | " | " | OMe | Me | CH | |
| 830 | " | " | " | " | Cl | OMe | CH | |
| 831 | " | " | " | " | OMe | Me | N | |
| 832 | " | " | " | Me | OMe | OMe | CH | |
| 833 | " | " | " | " | " | Me | N | |
| 834 | " | " | CO$_2$-n-Pr | H | OMe | OMe | CH | |
| 835 | " | " | " | " | OMe | Me | N | |
| 836 | " | " | " | " | OMe | Cl | CH | |
| 837 | " | " | " | " | Me | Me | CH | |
| 838 | " | " | " | Me | OMe | OMe | CH | |
| 839 | " | " | " | " | OMe | Me | N | |
| 840 | " | " | CO$_2$-i-Pr | H | OMe | OMe | CH | |
| 841 | " | " | " | " | OMe | Me | N | |
| 842 | " | " | " | " | Me | Me | CH | |
| 843 | " | " | " | Me | OMe | Me | N | |
| 844 | n-Pr | " | CO$_2$-Me | H | OMe | OMe | CH | |
| 845 | " | " | " | " | " | Cl | CH | |
| 846 | " | " | " | " | Me | Me | CH | |
| 847 | " | " | " | " | OMe | Me | N | |
| 848 | " | " | " | Me | OMe | OMe | CH | |
| 849 | " | " | " | " | OMe | Me | N | |

TABLE 1-continued

| No. | R¹ | R² | R³ | R⁴ | X | Y | Z | m.p. |
|---|---|---|---|---|---|---|---|---|
| 850 | n-Pr | " | CO₂-Et | H | " | " | N | |
| 851 | " | " | " | " | " | OMe | CH | |
| 852 | " | " | " | " | Me | Me | CH | |
| 853 | " | " | CO₂-n-Pr | " | OMe | OMe | CH | |
| 854 | i-Pr | " | CO₂-Me | H | OMe | OMe | CH | |
| 855 | " | " | " | " | OMe | Me | N | |
| 856 | " | " | " | " | Me | Me | CH | |
| 857 | " | " | " | " | Cl | OMe | N | |
| 858 | " | " | " | Me | OMe | Me | N | |
| 859 | " | " | " | " | " | OMe | CH | |
| 860 | Allyl | " | CO₂-Me | H | OMe | OMe | CH | |
| 861 | " | " | " | " | " | Cl | CH | |
| 862 | " | " | " | " | Me | Me | CH | |
| 863 | " | " | " | " | OMe | Me | N | |
| 864 | " | " | CO₂-Et | H | OMe | OMe | CH | |
| 865 | " | " | CO₂-n-Pr | H | OMe | OMe | CH | |
| 866 | " | " | CO₂-i-Pr | " | " | " | CH | |
| 867 | Me | CO-thienyl | CO₂-Me | H | OMe | OMe | CH | |
| 868 | " | " | " | " | " | OMe | N | |
| 869 | " | " | " | " | " | Me | N | |
| 870 | " | " | " | " | " | " | CH | |
| 871 | " | " | " | " | NMe₂ | OCH₂CF₃ | N | |
| 872 | " | " | " | " | Me | Me | CH | |
| 873 | " | " | " | " | " | Cl | N | |
| 874 | " | " | " | " | Cl | OMe | CH | |
| 875 | " | " | " | Me | OMe | OMe | CH | |
| 876 | " | " | " | " | " | Me | N | |
| 877 | " | " | CO₂-Et | H | OMe | OMe | CH | |
| 878 | " | " | " | " | " | Cl | CH | |
| 879 | " | " | " | " | Me | Me | CH | |
| 880 | " | " | " | " | OMe | Me | N | |
| 881 | " | " | " | " | NMe₂ | OCH₂CF₃ | N | |
| 882 | " | " | " | Me | OMe | OMe | CH | |
| 883 | " | " | " | " | OMe | Me | N | |
| 884 | " | " | CO₂-n-Pr | H | OMe | OMe | CH | |
| 885 | " | " | " | " | " | " | N | |
| 886 | " | " | " | " | OMe | Me | N | |
| 887 | " | " | " | " | Me | Me | CH | |
| 888 | " | " | " | " | OMe | Cl | CH | |
| 889 | " | " | " | Me | Me | OMe | N | |
| 890 | " | " | " | " | OMe | OMe | CH | |
| 891 | Me | " | CO₂-i-Pr | H | OMe | OMe | CH | |
| 892 | " | " | " | " | " | " | N | |
| 893 | " | " | " | " | H | Me | N | |
| 894 | " | " | " | " | OMe | Cl | CH | |
| 895 | " | " | " | " | Me | Me | CH | |
| 896 | " | " | " | " | SMe | NEt₂ | N | |
| 897 | " | " | CO₂-i-Pr | Me | OMe | Me | N | |
| 898 | " | " | " | " | OMe | OMe | CH | |
| 899 | Me | " | CO₂-Allyl | H | OMe | OMe | CH | |
| 900 | Et | " | CO₂-Me | H | OMe | OMe | CH | |
| 901 | " | " | " | H | OMe | Me | N | |
| 902 | " | " | " | " | Me | Me | CH | |
| 903 | " | " | " | " | Cl | OMe | CH | |
| 904 | " | " | " | Me | OMe | OMe | CH | |
| 905 | " | " | " | " | OMe | Me | N | |
| 906 | " | " | CO₂-Et | H | OMe | OMe | CH | |
| 907 | " | " | " | " | OMe | Me | CH | |
| 908 | " | " | " | " | Cl | OMe | CH | |
| 909 | " | " | " | " | OMe | Me | N | |
| 910 | " | " | " | Me | OMe | OMe | CH | |
| 911 | " | " | " | " | " | Me | N | |
| 912 | " | " | CO₂-n-Pr | H | OMe | OMe | CH | |

TABLE 1-continued

[Structure: R¹R²N-phenyl(R³)-SO₂NH-CO-NR⁴-pyrimidine/triazine with X, Y, Z substituents]

| No. | R¹ | R² | R³ | R⁴ | X | Y | Z | m.p. |
|---|---|---|---|---|---|---|---|---|
| 913 | " | " | " | " | OMe | Me | N | |
| 914 | " | " | " | " | OMe | Cl | CH | |
| 915 | " | " | " | " | Me | Me | CH | |
| 916 | " | " | " | Me | OMe | OMe | CH | |
| 917 | " | " | " | " | OMe | Me | N | |
| 918 | " | " | CO₂-i-Pr | H | OMe | OMe | CH | |
| 919 | " | " | " | " | OMe | Me | N | |
| 920 | " | " | " | " | Me | Me | CH | |
| 921 | " | " | " | Me | OMe | Me | N | |
| 922 | n-Pr | " | CO₂-Me | H | OMe | OMe | CH | |
| 923 | " | " | " | " | " | Cl | CH | |
| 924 | " | " | " | " | Me | Me | CH | |
| 925 | " | " | " | " | OMe | Me | N | |
| 926 | " | " | " | Me | OMe | OMe | CH | |
| 927 | " | " | " | " | OMe | Me | N | |
| 928 | n-Pr | " | CO₂-Et | H | " | " | N | |
| 929 | " | " | " | " | " | OMe | CH | |
| 930 | " | " | " | " | Me | Me | CH | |
| 931 | " | " | CO₂-n-Pr | " | OMe | OMe | CH | |
| 932 | i-Pr | " | CO₂-Me | H | OMe | OMe | CH | |
| 933 | " | " | " | " | OMe | Me | N | |
| 934 | " | " | " | " | Me | Me | CH | |
| 935 | " | " | " | " | Cl | OMe | N | |
| 936 | " | " | " | Me | OMe | Me | N | |
| 937 | " | " | " | " | " | OMe | CH | |
| 938 | Allyl | " | CO₂-Me | H | OMe | OMe | CH | |
| 939 | " | " | " | " | " | Cl | CH | |
| 940 | " | " | " | " | Me | Me | CH | |
| 941 | " | " | " | " | OMe | Me | N | |
| 942 | " | " | CO₂-Et | H | OMe | OMe | CH | |
| 943 | " | " | CO₂-n-Pr | " | " | " | CH | |
| 944 | " | " | CO₂-i-Pr | " | " | " | " | |
| 945 | Me | CO-furyl | CO₂-Me | H | OMe | OMe | CH | 164–167 |
| 946 | " | " | " | " | " | OMe | N | |
| 947 | " | " | " | " | " | Me | N | |
| 948 | " | " | " | " | " | " | CH | |
| 949 | " | " | " | " | NMe₂ | OCH₂CF₃ | N | |
| 950 | " | " | " | " | Me | Me | CH | |
| 951 | " | " | " | " | " | " | N | |
| 952 | " | " | " | " | Cl | OMe | CH | |
| 953 | " | " | " | Me | OMe | OMe | CH | |
| 954 | " | " | " | " | " | Me | N | |
| 955 | " | " | CO₂-Et | H | OMe | OMe | CH | |
| 956 | " | " | " | " | " | Cl | CH | |
| 957 | " | " | " | " | Me | Me | CH | |
| 958 | " | " | " | " | OMe | Me | N | |
| 959 | " | " | " | " | NMe₂ | OCH₂CF₃ | N | |
| 960 | " | " | " | Me | OMe | OMe | CH | |
| 961 | " | " | " | " | OMe | Me | N | |
| 962 | " | " | CO₂-n-Pr | H | OMe | OMe | CH | |
| 963 | " | " | " | " | " | " | N | |
| 964 | " | " | " | " | OMe | Me | N | |
| 965 | " | " | " | " | Me | Me | CH | |
| 966 | " | " | " | " | OMe | Cl | CH | |
| 967 | " | " | " | Me | Me | OMe | N | |
| 968 | " | " | " | " | OMe | OMe | CH | |
| 969 | Me | CO-furyl | CO₂-i-Pr | H | OMe | OMe | CH | |
| 970 | " | " | " | " | " | " | N | |

TABLE 1-continued

Structure: R¹R²N-phenyl(R³)-SO₂NH-CO-NR⁴-pyrimidine/triazine(X,Y,Z)

| No. | R¹ | R² | R³ | R⁴ | X | Y | Z | m.p. |
|---|---|---|---|---|---|---|---|---|
| 971 | " | " | " | " | H | Me | N | |
| 972 | " | " | " | " | OMe | Cl | CH | |
| 973 | " | " | " | " | Me | Me | CH | |
| 974 | " | " | " | " | SMe | NEt₂ | N | |
| 975 | " | " | CO₂-i-Pr | Me | OMe | Me | N | |
| 976 | " | " | CO₂-Allyl | " | OMe | OMe | CH | |
| 977 | Me | " | CO₂-Allyl | H | OMe | OMe | CH | |
| 978 | Et | " | CO₂-Me | H | OMe | OMe | CH | |
| 979 | " | " | " | H | OMe | Me | N | |
| 980 | " | " | " | " | Me | Me | CH | |
| 981 | " | " | " | " | Cl | OMe | CH | |
| 982 | " | " | " | Me | OMe | OMe | CH | |
| 983 | " | " | " | " | OMe | Me | N | |
| 984 | " | " | CO₂-Et | H | OMe | OMe | CH | |
| 985 | " | " | " | " | OMe | Me | CH | |
| 986 | " | " | " | " | Cl | OMe | CH | |
| 987 | " | " | " | " | OMe | Me | N | |
| 988 | " | " | " | Me | OMe | OMe | CH | |
| 989 | " | " | " | " | " | Me | N | |
| 990 | " | " | CO₂-n-Pr | H | OMe | OMe | CH | |
| 991 | " | " | " | " | OMe | Me | N | |
| 992 | " | " | " | " | OMe | Cl | CH | |
| 993 | " | " | " | " | Me | Me | CH | |
| 994 | " | " | " | Me | OMe | OMe | CH | |
| 995 | " | " | " | " | OMe | Me | N | |
| 996 | " | " | CO₂-i-Pr | H | OMe | OMe | CH | |
| 997 | " | " | " | " | OMe | Me | N | |
| 998 | " | " | " | " | Me | Me | CH | |
| 999 | " | " | " | Me | OMe | Me | N | |
| 1.000 | n-Pr | " | CO₂-Me | H | OMe | OMe | CH | |
| 1.001 | " | " | " | " | " | Cl | CH | |
| 1.002 | " | " | " | " | Me | Me | CH | |
| 1.003 | " | " | " | " | OMe | Me | N | |
| 1.004 | " | " | " | Me | OMe | OMe | CH | |
| 1.005 | " | " | " | " | OMe | Me | N | |
| 1.006 | n-Pr | " | CO₂-Et | H | " | " | N | |
| 1.007 | " | " | " | " | Cl | OMe | CH | |
| 1.008 | " | " | " | " | Me | Me | CH | |
| 1.009 | " | " | CO₂-n-Pr | " | OMe | OMe | CH | |
| 1.010 | i-Pr | " | CO₂-Me | H | OMe | OMe | CH | |
| 1.011 | " | " | " | " | OMe | Me | N | |
| 1.012 | " | " | " | " | Me | Me | CH | |
| 1.013 | " | " | " | " | Cl | OMe | N | |
| 1.014 | " | " | " | Me | OMe | Me | N | |
| 1.015 | " | " | " | " | " | OMe | CH | |
| 1.016 | Allyl | " | CO₂-Me | H | OMe | OMe | CH | |
| 1.017 | " | " | " | " | " | Cl | CH | |
| 1.018 | " | " | " | " | Me | Me | CH | |
| 1.019 | " | " | " | " | OMe | Me | N | |
| 1.020 | " | " | CO₂-Et | H | OMe | OMe | CH | |
| 1.021 | " | " | CO₂-n-Pr | " | " | " | CH | |
| 1.022 | " | " | CO₂-i-Pr | " | " | " | CH | |
| 1.023 | Me | CO-Ph | CO₂-Me | H | " | " | CH | 177–183 |
| 1.024 | " | " | " | " | " | OMe | N | |
| 1.025 | " | " | " | " | " | Me | N | |
| 1.026 | " | " | " | " | OMe | " | CH | |
| 1.027 | " | " | " | " | NMe₂ | OCH₂CF₃ | N | |
| 1.028 | " | " | " | " | Me | Me | CH | |
| 1.029 | " | " | " | " | " | " | N | |
| 1.030 | " | " | " | " | Cl | OMe | CH | |
| 1.031 | " | " | " | Me | OMe | OMe | CH | |
| 1.032 | " | " | " | " | " | Me | N | |
| 1.033 | " | " | CO₂-Et | H | OMe | OMe | CH | |
| 1.034 | " | " | " | " | " | Cl | CH | |
| 1.035 | " | " | " | " | Me | Me | CH | |
| 1.036 | " | " | " | " | OMe | Me | N | |
| 1.037 | " | " | " | " | NMe₂ | OCH₂CF₃ | N | |
| 1.038 | " | " | " | Me | OMe | OMe | CH | |

TABLE 1-continued $$R^1R^2N-C_6H_3(R^3)-SO_2NH-CO-NR^4-\text{pyrimidine}(X,Y,Z)$$

| No. | R¹ | R² | R³ | R⁴ | X | Y | Z | m.p. |
|---|---|---|---|---|---|---|---|---|
| 1.039 | " | " | " | " | OMe | Me | N | |
| 1.040 | " | " | CO₂-n-Pr | H | OMe | OMe | CH | |
| 1.041 | " | " | " | " | " | " | N | |
| 1.042 | " | " | " | " | OMe | Me | N | |
| 1.043 | " | " | " | " | Me | Me | CH | |
| 1.044 | " | " | " | " | OMe | Cl | CH | |
| 1.045 | " | " | " | Me | Me | OMe | N | |
| 1.046 | " | " | " | " | OMe | OMe | CH | |
| 1.047 | Me | CO-Ph | CO₂-i-Pr | OMe | OMe | OMe | CH | |
| 1.048 | " | " | " | " | " | " | N | |
| 1.049 | " | " | " | " | OMe | Me | N | |
| 1.050 | " | " | " | " | OMe | Cl | CH | |
| 1.051 | " | " | " | " | Me | Me | CH | |
| 1.052 | " | " | " | " | SMe | NEt₂ | N | |
| 1.053 | " | " | CO₂-i-Pr | Me | OMe | Me | N | |
| 1.054 | " | " | " | " | OMe | OMe | CH | |
| 1.055 | Me | " | CO₂-Allyl | H | OMe | OMe | CH | |
| 1.056 | Et | " | CO₂-Me | H | OMe | OMe | CH | |
| 1.057 | " | " | " | H | OMe | Me | N | |
| 1.058 | " | " | " | " | Me | Me | CH | |
| 1.059 | " | " | " | " | Cl | OMe | CH | |
| 1.060 | " | " | " | Me | OMe | OMe | CH | |
| 1.061 | " | " | " | " | OMe | Me | N | |
| 1.062 | " | " | CO₂-Et | H | OMe | OMe | CH | |
| 1.063 | " | " | " | " | OMe | Me | CH | |
| 1.064 | " | " | " | " | Cl | OMe | CH | |
| 1.065 | " | " | " | " | OMe | Me | N | |
| 1.066 | " | " | " | Me | OMe | OMe | CH | |
| 1.067 | " | " | " | " | " | Me | N | |
| 1.068 | " | " | CO₂-n-Pr | H | OMe | OMe | CH | |
| 1.069 | " | " | " | " | OMe | Me | N | |
| 1.070 | " | " | " | " | OMe | Cl | CH | |
| 1.071 | " | " | " | " | Me | Me | CH | |
| 1.072 | " | " | " | Me | OMe | OMe | CH | |
| 1.073 | " | " | " | " | OMe | Me | N | |
| 1.074 | " | " | CO₂-i-Pr | H | OMe | OMe | CH | |
| 1.075 | " | " | " | " | OMe | Me | N | |
| 1.076 | " | " | " | Me | OMe | Me | N | |
| 1.077 | n-Pr | CO-Ph | CO₂-Me | H | OMe | OMe | CH | |
| 1.078 | " | " | " | " | " | Cl | CH | |
| 1.079 | " | " | " | " | Me | Me | CH | |
| 1.080 | " | " | " | " | OMe | Me | N | |
| 1.081 | " | " | " | Me | OMe | OMe | CH | |
| 1.082 | " | " | " | " | OMe | Me | N | |
| 1.083 | n-Pr | " | CO₂-Et | H | " | " | N | |
| 1.084 | " | " | " | " | " | OMe | CH | |
| 1.085 | " | " | " | " | Me | Me | CH | |
| 1.086 | " | " | CO₂-n-Pr | " | OMe | OMe | CH | |
| 1.087 | i-Pr | " | CO₂-Me | H | OMe | OMe | CH | |
| 1.088 | " | " | " | " | OMe | Me | N | |
| 1.089 | " | " | " | " | Me | Me | CH | |
| 1.090 | " | " | " | " | Cl | OMe | N | |
| 1.091 | " | " | " | Me | OMe | Me | N | |
| 1.092 | " | " | " | " | " | OMe | CH | |
| 1.093 | Allyl | " | CO₂-Me | H | OMe | OMe | CH | |
| 1.094 | " | " | " | " | " | Cl | CH | |
| 1.095 | " | " | " | " | Me | Me | CH | |
| 1.096 | " | " | " | " | OMe | Me | N | |
| 1.097 | " | " | CO₂-Et | H | OMe | OMe | CH | |
| 1.098 | " | " | CO₂-n-Pr | H | OMe | OMe | CH | |
| 1.099 | " | " | CO₂-i-Pr | " | " | " | CH | |
| 1.100 | Me, CO-(2,4-diCl-C₆H₃) | | CO₂-Me | H | OMe | OMe | CH | |
| 1.101 | " | " | " | " | " | OMe | N | |

TABLE 1-continued

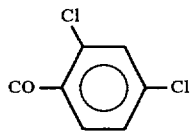

| No. | R¹ | R² | R³ | R⁴ | X | Y | Z | m.p. |
|---|---|---|---|---|---|---|---|---|
| 1.102 | " | " | " | " | " | Me | N | |
| 1.103 | " | " | " | " | " | " | CH | |
| 1.104 | " | " | " | " | NMe₂ | OCH₂CF₃ | N | |
| 1.105 | " | " | " | " | Me | Me | CH | |
| 1.106 | " | " | " | " | " | " | N | |
| 1.107 | " | " | " | " | Cl | OMe | CH | |
| 1.108 | " | " | " | Me | OMe | OMe | CH | |
| 1.109 | " | " | " | " | " | Me | N | |
| 1.110 | " | " | CO₂-Et | H | OMe | OMe | CH | |
| 1.111 | " | " | " | " | " | Cl | CH | |
| 1.112 | " | " | " | " | Me | Me | CH | |
| 1.113 | " | " | " | " | OMe | Me | N | |
| 1.114 | " | " | " | " | NMe₂ | OCH₂CF₃ | N | |
| 1.115 | " | " | " | Me | OMe | OMe | CH | |
| 1.116 | " | " | " | " | OMe | Me | N | |
| 1.117 | " | " | CO₂-n-Pr | H | OMe | OMe | CH | |
| 1.118 | " | " | " | " | " | " | N | |
| 1.119 | " | " | " | " | OMe | Me | N | |
| 1.120 | " | " | " | " | Me | Me | CH | |
| 1.121 | " | " | " | " | OMe | Cl | CH | |
| 1.122 | " | " | " | Me | Me | OMe | N | |
| 1.123 | " | " | " | " | OMe | OMe | CH | |
| 1.124 | Me | " | CO₂-i-Pr | H | OMe | OMe | CH | |
| 1.125 | " | " | " | " | " | " | N | |
| 1.126 | " | " | " | " | H | Me | N | |
| 1.127 | " | " | " | " | OMe | Cl | CH | |
| 1.128 | " | " | " | " | Me | Me | CH | |
| 1.129 | " | " | " | " | SMe | NEt₂ | N | |
| 1.130 | " | " | CO₂-i-Pr | Me | OMe | Me | N | |
| 1.131 | " | " | " | " | OMe | OMe | CH | |
| 1.132 | Me | " | CO₂-Allyl | H | OMe | OMe | CH | |
| 1.133 | Et | " | CO₂-Me | H | OMe | OMe | CH | |
| 1.134 | " | " | " | H | OMe | Me | N | |
| 1.135 | " | " | " | " | Me | Me | CH | |
| 1.136 | " | " | " | " | Cl | OMe | CH | |
| 1.137 | " | " | " | Me | OMe | OMe | CH | |
| 1.138 | " | " | " | " | OMe | Me | N | |
| 1.139 | " | " | CO₂-Et | H | OMe | OMe | CH | |
| 1.140 | " | " | " | " | OMe | Me | CH | |
| 1.141 | " | " | " | " | Cl | OMe | CH | |
| 1.142 | " | " | " | " | OMe | Me | N | |
| 1.143 | " | " | " | Me | OMe | OMe | CH | |
| 1.144 | " | " | " | " | " | Me | N | |
| 1.145 | " | " | CO₂-n-Pr | H | OMe | OMe | CH | |
| 1.146 | " | " | " | " | OMe | Me | N | |
| 1.147 | " | " | " | " | OMe | Cl | CH | |
| 1.148 | " | " | " | " | Me | Me | CH | |
| 1.149 | " | " | " | Me | OMe | OMe | CH | |
| 1.150 | " | " | " | Me | OMe | Me | N | |
| 1.151 | " | " | CO₂i-Pr | H | OMe | OMe | CH | |
| 1.152 | " | " | " | " | OMe | Me | N | |
| 1.153 | " | " | " | " | Me | Me | CH | |
| 1.154 | " | " | " | Me | OMe | Me | N | |
| 1.155 | n-Pr | 2,4-Cl₂-C₆H₃-CO | CO₂-Me | H | OMe | OMe | CH | |
| 1.156 | " | " | " | " | " | Cl | CH | |
| 1.157 | " | " | " | " | Me | Me | CH | |
| 1.158 | " | " | " | " | OMe | Me | N | |
| 1.159 | " | " | " | Me | OMe | OMe | CH | |
| 1.160 | " | " | " | " | OMe | Me | N | |
| 1.161 | n-Pr | " | CO₂-Et | H | OMe | Me | N | |
| 1.162 | " | " | " | " | " | OMe | CH | |

TABLE 1-continued

Structure: R¹R²N-phenyl(R³)-SO₂NH-CO-NR⁴-pyrimidine(X,Y,Z)

| No. | R¹ | R² | R³ | R⁴ | X | Y | Z | m.p. |
|---|---|---|---|---|---|---|---|---|
| 1.163 | " | " | " | " | Me | Me | CH | |
| 1.164 | " | " | CO₂-n-Pr | " | OMe | OMe | CH | |
| 1.165 | i-Pr | " | CO₂-Me | H | OMe | OMe | CH | |
| 1.166 | " | " | " | " | OMe | Me | N | |
| 1.167 | " | " | " | " | Me | Me | CH | |
| 1.168 | " | " | " | " | Cl | OMe | N | |
| 1.169 | " | " | " | Me | OMe | Me | N | |
| 1.170 | " | " | " | " | " | OMe | CH | |
| 1.171 | Allyl | " | CO₂-Me | H | OMe | OMe | CH | |
| 1.172 | " | " | " | " | " | Cl | CH | |
| 1.173 | " | " | " | " | Me | Me | CH | |
| 1.174 | " | " | " | " | OMe | Me | N | |
| 1.175 | " | " | CO₂-Et | H | OMe | OMe | CH | |
| 1.176 | " | " | CO₂-n-Pr | " | OMe | OMe | CH | |
| 1.177 | " | " | CO₂-i-Pr | H | OMe | OMe | CH | |
| 1.178 | Me | CO—OMe | CO₂-Me | H | OMe | OMe | CH | 128° C. |
| 1.179 | " | " | " | " | " | OMe | N | |
| 1.180 | " | " | " | " | " | Me | N | s. Bsp. o) |
| 1.181 | " | " | " | " | " | " | CH | 89–101 |
| 1.182 | " | " | " | " | NMe₂ | OCH₂CF₃ | N | |
| 1.183 | " | " | " | " | Me | Me | CH | s. Bsp. m) |
| 1.184 | " | " | " | " | " | " | N | |
| 1.185 | " | " | " | " | Cl | OMe | CH | s. Bsp. n) |
| 1.186 | " | " | " | Me | OMe | OMe | CH | 150–154 |
| 1.187 | " | " | " | " | " | Me | N | |
| 1.188 | " | " | CO₂-Et | H | OMe | OMe | CH | |
| 1.189 | " | " | " | " | " | Cl | CH | |
| 1.190 | " | " | " | " | Me | Me | CH | |
| 1.191 | " | " | " | " | OMe | Me | N | |
| 1.192 | " | " | " | " | NMe₂ | OCH₂CF₃ | N | |
| 1.193 | " | " | " | Me | OMe | OMe | CH | |
| 1.194 | " | " | " | " | OMe | Me | N | |
| 1.195 | " | " | CO₂-n-Pr | H | OMe | OMe | CH | |
| 1.196 | " | " | " | " | " | " | N | |
| 1.197 | " | " | " | " | OMe | Me | N | |
| 1.198 | " | " | " | " | Me | Me | CH | |
| 1.199 | " | " | " | " | OMe | Cl | CH | |
| 1.200 | " | " | " | Me | Me | OMe | N | |
| 1.201 | " | " | " | " | OMe | OMe | CH | |
| 1.202 | Me | CO—OMe | CO₂-i-Pr | H | OMe | OMe | CH | |
| 1.203 | " | " | " | " | " | " | N | |
| 1.204 | " | " | " | " | OMe | Me | N | |
| 1.205 | " | " | " | " | OMe | Cl | CH | |
| 1.206 | " | " | " | " | Me | Me | CH | |
| 1.207 | " | " | " | " | SMe | NEt₂ | N | |
| 1.208 | " | " | CO₂-i-Pr | Me | OMe | Me | N | |
| 1.209 | " | " | " | " | OMe | OMe | CH | |
| 1.210 | Me | " | CO₂-Allyl | H | OMe | OMe | CH | |
| 1.211 | Et | " | CO₂-Me | H | OMe | OMe | CH | |
| 1.212 | " | " | " | H | OMe | Me | N | |
| 1.213 | " | " | " | " | Me | Me | CH | |
| 1.214 | " | " | " | " | Cl | OMe | CH | |
| 1.215 | " | " | " | Me | OMe | OMe | CH | |
| 1.216 | " | " | " | " | OMe | Me | N | |
| 1.217 | " | " | CO₂-Et | H | OMe | OMe | CH | |
| 1.218 | " | " | " | " | OMe | Me | CH | |
| 1.219 | " | " | " | " | Cl | OMe | CH | |
| 1.220 | " | " | " | " | OMe | Me | N | |
| 1.221 | " | " | " | Me | OMe | OMe | CH | |
| 1.222 | " | " | " | " | " | Me | N | |
| 1.223 | " | " | CO₂-n-Pr | H | OMe | OMe | CH | |
| 1.224 | " | " | " | " | OMe | Me | N | |
| 1.225 | " | " | " | " | OMe | Cl | CH | |
| 1.226 | " | " | " | " | Me | Me | CH | |
| 1.227 | " | " | " | Me | OMe | OMe | CH | |
| 1.228 | " | " | " | " | OMe | Me | N | |
| 1.229 | " | " | CO₂-i-Pr | H | OMe | OMe | CH | |
| 1.230 | " | " | " | " | OMe | Me | N | |

TABLE 1-continued

| No. | R$^1$ | R$^2$ | R$^3$ | R$^4$ | X | Y | Z | m.p. |
|---|---|---|---|---|---|---|---|---|
| 1.231 | " | " | " | " | Me | Me | CH | |
| 1.232 | " | " | " | Me | OMe | Me | N | |
| 1.233 | n-Pr | CO—OMe | CO$_2$-Me | H | OMe | OMe | CH | |
| 1.234 | " | " | " | " | " | Cl | CH | |
| 1.235 | " | " | " | " | Me | Me | CH | |
| 1.236 | " | " | " | " | OMe | Me | N | |
| 1.237 | " | " | " | Me | OMe | OMe | CH | |
| 1.238 | " | " | " | " | OMe | Me | N | |
| 1.239 | n-Pr | " | CO$_2$-Et | H | OMe | Me | N | |
| 1.240 | " | " | " | " | " | OMe | CH | |
| 1.241 | " | " | " | " | Me | Me | CH | |
| 1.242 | " | " | CO$_2$-n-Pr | " | OMe | OMe | CH | |
| 1.243 | i-Pr | " | CO$_2$-Me | H | OMe | OMe | CH | |
| 1.244 | " | " | " | " | OMe | Me | N | |
| 1.245 | " | " | " | " | Me | Me | CH | |
| 1.246 | " | " | " | " | Cl | OMe | N | |
| 1.247 | " | " | " | Me | OMe | Me | N | |
| 1.248 | " | " | " | " | " | OMe | CH | |
| 1.249 | Allyl | " | CO$_2$-Me | H | OMe | OMe | CH | |
| 1.250 | " | " | " | " | " | Cl | CH | |
| 1.251 | " | " | " | " | Me | Me | CH | |
| 1.252 | " | " | " | " | OMe | Me | N | |
| 1.253 | " | " | CO$_2$-Et | H | OMe | OMe | CH | |
| 1.254 | " | " | CO$_2$-n-Pr | " | " | " | " | |
| 1.255 | " | " | CO$_2$-i-Pr | " | " | " | CH | |
| 1.256 | Me | CO—OEt | CO$_2$-Me | H | OMe | OMe | CH | 90–94 |
| 1.257 | " | " | " | " | " | OMe | N | |
| 1.258 | " | " | " | " | " | Me | N | |
| 1.259 | " | " | " | " | " | " | CH | |
| 1.260 | " | " | " | " | NMe$_2$ | OCH$_2$CF$_3$ | N | |
| 1.261 | " | " | " | " | Me | Me | CH | |
| 1.262 | " | " | " | " | " | " | N | |
| 1.263 | " | " | " | " | Cl | OMe | CH | |
| 1.264 | " | " | " | Me | OMe | OMe | CH | |
| 1.265 | " | " | " | " | " | Me | N | |
| 1.266 | " | " | CO$_2$-Et | H | OMe | OMe | CH | |
| 1.267 | " | " | " | " | " | Cl | CH | |
| 1.268 | " | " | " | " | Me | Me | CH | |
| 1.269 | " | " | " | " | OMe | Me | N | |
| 1.270 | " | " | " | " | NMe$_2$ | OCH$_2$CF$_3$ | N | |
| 1.271 | " | " | " | Me | OMe | OMe | CH | |
| 1.272 | " | " | " | " | OMe | Me | N | |
| 1.273 | " | " | CO$_2$-n-Pr | H | OMe | OMe | CH | |
| 1.274 | " | " | " | " | " | " | N | |
| 1.275 | " | " | " | " | OMe | Me | N | |
| 1.276 | " | " | " | " | Me | Me | CH | |
| 1.277 | " | " | " | " | OMe | Cl | CH | |
| 1.278 | " | " | " | Me | Me | OMe | N | |
| 1.279 | " | " | " | " | OMe | OMe | CH | |
| 1.280 | Me | CO—OEt | CO$_2$-i-Pr | H | OMe | OMe | CH | |
| 1.281 | " | " | " | " | " | " | N | |
| 1.282 | " | " | " | " | OMe | Me | N | |
| 1.283 | " | " | " | " | OMe | Cl | CH | |
| 1.284 | " | " | " | " | Me | Me | CH | |
| 1.285 | " | " | " | " | SMe | NEt$_2$ | N | |
| 1.286 | " | " | CO$_2$-i-Pr | Me | OMe | Me | N | |
| 1.287 | " | " | " | " | OMe | OMe | CH | |
| 1.288 | Me | " | CO$_2$-Allyl | H | OMe | OMe | CH | |
| 1.289 | Et | " | CO$_2$-Me | H | OMe | OMe | CH | |
| 1.290 | " | " | " | H | OMe | Me | N | |
| 1.291 | " | " | " | " | Me | Me | CH | |
| 1.292 | " | " | " | " | Cl | OMe | CH | |
| 1.293 | " | " | " | Me | OMe | OMe | CH | |
| 1.294 | " | " | " | " | OMe | Me | N | |
| 1.295 | " | " | CO$_2$-Et | H | OMe | OMe | CH | |
| 1.296 | " | " | " | " | OMe | Me | CH | |
| 1.297 | " | " | " | " | Cl | OMe | CH | |
| 1.298 | " | " | " | " | OMe | Me | N | |

TABLE 1-continued

![Structure: R1R2N-phenyl(R3)-SO2NH-CO-NR4-triazine/pyrimidine with X, Y, Z substituents]

| No. | R¹ | R² | R³ | R⁴ | X | Y | Z | m.p. |
|---|---|---|---|---|---|---|---|---|
| 1.299 | " | " | " | Me | OMe | OMe | CH | |
| 1.300 | " | " | " | " | " | Me | N | |
| 1.301 | " | " | CO₂-n-Pr | H | OMe | OMe | CH | |
| 1.302 | " | " | " | " | OMe | Me | N | |
| 1.303 | " | " | " | " | OMe | Cl | CH | |
| 1.304 | " | " | " | " | Me | Me | CH | |
| 1.305 | " | " | " | Me | OMe | OMe | CH | |
| 1.306 | " | " | " | " | OMe | Me | N | |
| 1.307 | " | " | CO₂-i-Pr | H | OMe | OMe | CH | |
| 1.308 | " | " | " | " | OMe | Me | N | |
| 1.309 | " | " | " | " | Me | Me | CH | |
| 1.310 | " | " | " | Me | OMe | Me | N | |
| 1.311 | n-Pr | CO—OEt | CO₂-Me | H | OMe | OMe | CH | |
| 1.312 | " | " | " | " | " | Cl | CH | |
| 1.313 | " | " | " | " | Me | Me | CH | |
| 1.314 | " | " | " | " | OMe | Me | N | |
| 1.315 | " | " | " | Me | OMe | OMe | CH | |
| 1.316 | " | " | " | " | OMe | Me | N | |
| 1.317 | n-Pr | " | CO₂-Et | H | " | " | N | |
| 1.318 | " | " | " | " | " | OMe | CH | |
| 1.319 | " | " | " | " | Me | Me | CH | |
| 1.320 | " | " | CO₂-n-Pr | " | OMe | OMe | CH | |
| 1.321 | i-Pr | " | CO₂-Me | H | OMe | OMe | CH | |
| 1.322 | " | " | " | " | OMe | Me | N | |
| 1.323 | " | " | " | " | Me | Me | CH | |
| 1.324 | " | " | " | " | Cl | OMe | N | |
| 1.325 | " | " | " | Me | OMe | Me | N | |
| 1.326 | " | " | " | " | " | OMe | CH | |
| 1.327 | Allyl | " | CO₂-Me | H | OMe | OMe | CH | |
| 1.328 | " | " | " | " | " | Cl | CH | |
| 1.329 | " | " | " | " | Me | Me | CH | |
| 1.330 | " | " | " | " | OMe | Me | N | |
| 1.331 | " | " | CO₂-Et | H | OMe | OMe | CH | |
| 1.332 | " | " | CO₂-n-Pr | H | OMe | OMe | CH | |
| 1.333 | " | " | CO₂-i-Pr | " | " | " | " | |
| 1.334 | Me | CO—O-i-Pr | CO₂-Me | H | OMe | OMe | CH | 159–162 |
| 1.335 | " | " | " | " | " | OMe | N | |
| 1.336 | " | " | " | " | " | Me | N | |
| 1.337 | " | " | " | " | " | " | CH | |
| 1.338 | " | " | " | " | NMe₂ | OCH₂CF₃ | N | |
| 1.339 | " | " | " | " | Me | Me | CH | |
| 1.340 | " | " | " | " | " | " | N | |
| 1.341 | " | " | " | " | Cl | OMe | CH | |
| 1.342 | " | " | " | Me | OMe | OMe | CH | |
| 1.343 | " | " | " | " | " | Me | N | |
| 1.344 | " | " | CO₂-Et | H | OMe | OMe | CH | |
| 1.345 | " | " | " | " | " | Cl | CH | |
| 1.346 | " | " | " | " | Me | Me | CH | |
| 1.347 | " | " | " | " | OMe | Me | N | |
| 1.348 | " | " | " | " | NMe₂ | OCH₂CF₃ | N | |
| 1.349 | " | " | " | Me | OMe | OMe | CH | |
| 1.350 | " | " | " | " | OMe | Me | N | |
| 1.351 | " | " | CO₂-n-Pr | H | OMe | OMe | CH | |
| 1.352 | " | " | " | " | " | " | N | |
| 1.353 | " | " | " | " | OMe | Me | N | |
| 1.354 | " | " | " | " | Me | Me | CH | |
| 1.355 | " | " | " | " | OMe | Cl | CH | |
| 1.356 | " | " | " | Me | Me | OMe | N | |
| 1.357 | " | " | " | " | OMe | OMe | CH | |
| 1.358 | Me | CO—O-i-Pr | CO₂-i-Pr | H | OMe | OMe | CH | |
| 1.359 | " | " | " | " | " | " | N | |
| 1.360 | " | " | " | " | H | Me | N | |
| 1.361 | " | " | " | " | OMe | Cl | CH | |
| 1.362 | " | " | " | " | Me | Me | CH | |
| 1.363 | " | " | " | " | SMe | NEt₂ | N | |
| 1.364 | " | " | CO₂-i-Pr | Me | OMe | N | | |
| 1.365 | " | " | " | " | OMe | OMe | CH | |
| 1.366 | Me | " | CO₂-Allyl | H | OMe | OMe | CH | |

TABLE 1-continued

| No. | R¹ | R² | R³ | R⁴ | X | Y | Z | m.p. |
|---|---|---|---|---|---|---|---|---|
| 1.367 | Et | " | $CO_2$-Me | H | OMe | OMe | CH | |
| 1.368 | " | " | " | H | OMe | Me | N | |
| 1.369 | " | " | " | " | Me | Me | CH | |
| 1.370 | " | " | " | " | Cl | OMe | CH | |
| 1.371 | " | " | " | Me | OMe | OMe | CH | |
| 1.372 | " | " | " | " | OMe | Me | N | |
| 1.373 | " | " | $CO_2$-Et | H | OMe | OMe | CH | |
| 1.374 | " | " | " | " | OMe | Me | CH | |
| 1.375 | " | " | " | " | Cl | OMe | CH | |
| 1.376 | " | " | " | " | OMe | Me | N | |
| 1.377 | " | " | " | Me | OMe | OMe | CH | |
| 1.378 | " | " | " | " | " | Me | N | |
| 1.379 | " | " | $CO_2$-n-Pr | H | OMe | OMe | CH | |
| 1.380 | " | " | " | " | OMe | Me | N | |
| 1.381 | " | " | " | " | OMe | Cl | CH | |
| 1.382 | " | " | " | " | Me | Me | CH | |
| 1.383 | " | " | " | Me | OMe | OMe | CH | |
| 1.384 | " | " | " | " | OMe | Me | N | |
| 1.385 | " | " | $CO_2$-i-Pr | H | OMe | OMe | CH | |
| 1.386 | " | " | " | " | OMe | Me | N | |
| 1.387 | " | " | " | " | Me | Me | CH | |
| 1.388 | " | " | " | Me | OMe | Me | N | |
| 1.389 | n-Pr | CO—O-i-Pr | $CO_2$-Me | H | OMe | OMe | CH | |
| 1.390 | " | " | " | " | " | Cl | CH | |
| 1.391 | " | " | " | " | Me | Me | CH | |
| 1.392 | " | " | " | " | OMe | Me | N | |
| 1.393 | " | " | " | Me | OMe | OMe | CH | |
| 1.394 | " | " | " | " | OMe | Me | N | |
| 1.395 | n-Pr | " | $CO_2$-Et | H | " | " | N | |
| 1.396 | " | " | " | " | " | OMe | CH | |
| 1.397 | " | " | " | " | Me | Me | CH | |
| 1.398 | " | " | $CO_2$-n-Pr | " | OMe | OMe | CH | |
| 1.399 | i-Pr | " | $CO_2$-Me | H | OMe | OMe | CH | |
| 1.400 | " | " | " | " | OMe | Me | N | |
| 1.401 | " | " | " | " | Me | Me | CH | |
| 1.402 | " | " | " | " | Cl | OMe | N | |
| 1.403 | " | " | " | Me | OMe | Me | N | |
| 1.404 | " | " | " | " | " | OMe | CH | |
| 1.405 | Allyl | " | $CO_2$-Me | H | OMe | OMe | CH | |
| 1.406 | " | " | " | " | " | Cl | CH | |
| 1.407 | " | " | " | " | Me | Me | CH | |
| 1.408 | " | " | " | " | OMe | Me | N | |
| 1.409 | " | " | $CO_2$-Et | H | OMe | OMe | CH | |
| 1.410 | " | " | $CO_2$-n-Pr | " | " | " | CH | |
| 1.411 | " | " | $CO_2$-i-Pr | " | " | " | CH | |
| 1.412 | Me | CO—O-n-Pr | $CO_2$-Me | H | OMe | OMe | CH | |
| 1.413 | " | " | " | " | " | OMe | N | |
| 1.414 | " | " | " | " | " | Me | N | |
| 1.415 | " | " | " | " | " | " | CH | |
| 1.416 | " | " | " | " | $NMe_2$ | $OCH_2CF_3$ | N | |
| 1.417 | " | " | " | " | Me | Me | CH | |
| 1.418 | " | " | " | " | " | " | N | |
| 1.419 | " | " | " | " | Cl | OMe | CH | |
| 1.420 | " | " | " | Me | OMe | OMe | CH | |
| 1.421 | " | " | " | " | " | Me | N | |
| 1.422 | " | " | $CO_2$-Et | H | OMe | OMe | CH | |
| 1.423 | " | " | " | " | " | Cl | CH | |
| 1.424 | " | " | " | " | Me | Me | CH | |
| 1.425 | " | " | " | " | OMe | Me | N | |
| 1.426 | " | " | " | " | $NMe_2$ | $OCH_2CF_3$ | N | |
| 1.427 | " | " | " | Me | OMe | OMe | CH | |
| 1.428 | " | " | " | " | OMe | Me | N | |
| 1.429 | " | " | $CO_2$-n-Pr | H | OMe | OMe | CH | |
| 1.430 | " | " | " | " | " | " | N | |
| 1.431 | " | " | " | " | OMe | Me | N | |
| 1.432 | " | " | " | " | Me | Me | CH | |
| 1.433 | " | " | " | " | OMe | Cl | CH | |
| 1.434 | " | " | " | Me | Me | OMe | N | |

TABLE 1-continued

| No. | R¹ | R² | R³ | R⁴ | X | Y | Z | m.p. |
|---|---|---|---|---|---|---|---|---|
| 1.435 | " | " | " | " | OMe | OMe | CH | |
| 1.436 | Me | CO—O-n-Pr | CO₂-i-Pr | H | OMe | OMe | CH | |
| 1.437 | " | " | " | " | " | " | N | |
| 1.438 | " | " | " | " | OMe | Me | N | |
| 1.439 | " | " | " | " | OMe | Cl | CH | |
| 1.440 | " | " | " | " | Me | Me | CH | |
| 1.441 | " | " | " | " | SMe | NEt₂ | N | |
| 1.442 | " | " | CO₂-i-Pr | Me | OMe | Me | N | |
| 1.443 | " | " | " | " | OMe | OMe | CH | |
| 1.444 | Me | " | CO₂-Allyl | H | OMe | OMe | CH | |
| 1.445 | Et | " | CO₂-Me | H | OMe | OMe | CH | |
| 1.446 | " | " | " | H | OMe | Me | N | |
| 1.447 | " | " | " | " | Me | Me | CH | |
| 1.448 | " | " | " | " | Cl | OMe | CH | |
| 1.449 | " | " | " | Me | OMe | OMe | CH | |
| 1.450 | " | " | " | " | OMe | Me | N | |
| 1.451 | " | " | CO₂-Et | H | OMe | OMe | CH | |
| 1.452 | " | " | " | " | OMe | Me | CH | |
| 1.453 | " | " | " | " | Cl | OMe | CH | |
| 1.454 | " | " | " | " | OMe | Me | N | |
| 1.455 | " | " | " | Me | OMe | OMe | CH | |
| 1.456 | " | " | " | " | " | Me | N | |
| 1.457 | " | " | CO₂-n-Pr | H | OMe | OMe | CH | |
| 1.458 | " | " | " | " | OMe | Me | N | |
| 1.459 | " | " | " | " | OMe | Cl | CH | |
| 1.460 | " | " | " | " | Me | Me | CH | |
| 1.461 | " | " | " | Me | OMe | OMe | CH | |
| 1.462 | " | " | " | " | OMe | Me | N | |
| 1.463 | " | " | CO₂-i-Pr | H | OMe | OMe | CH | |
| 1.464 | " | " | " | " | OMe | Me | N | |
| 1.465 | " | " | " | " | Me | Me | CH | |
| 1.466 | " | " | " | Me | OMe | Me | N | |
| 1.467 | n-Pr | CO—O-n-Pr | CO₂-Me | H | OMe | OMe | CH | |
| 1.468 | " | " | " | " | " | Cl | CH | |
| 1.469 | " | " | " | " | Me | Me | CH | |
| 1.470 | " | " | " | " | OMe | Me | N | |
| 1.471 | " | " | " | Me | OMe | OMe | CH | |
| 1.472 | " | " | " | " | OMe | Me | N | |
| 1.473 | n-Pr | " | CO₂-Et | H | " | " | N | |
| 1.474 | " | " | " | " | " | OMe | CH | |
| 1.475 | " | " | " | " | Me | Me | CH | |
| 1.476 | " | " | CO₂-n-Pr | " | OMe | OMe | CH | |
| 1.477 | i-Pr | " | CO₂-Me | H | OMe | OMe | CH | |
| 1.478 | " | " | " | " | OMe | Me | N | |
| 1.479 | " | " | " | " | Me | Me | CH | |
| 1.480 | " | " | " | " | Cl | OMe | N | |
| 1.481 | " | " | " | Me | OMe | Me | N | |
| 1.482 | " | " | " | " | " | OMe | CH | |
| 1.483 | Allyl | " | CO₂-Me | H | OMe | OMe | CH | |
| 1.484 | " | " | " | " | " | Cl | CH | |
| 1.485 | " | " | " | " | Me | Me | CH | |
| 1.486 | " | " | " | " | OMe | Me | N | |
| 1.487 | " | " | CO₂-Et | H | OMe | OMe | CH | |
| 1.488 | " | " | CO₂-n-Pr | " | " | " | CH | |
| 1.489 | " | " | CO₂-i-Pr | " | " | " | CH | |
| 1.490 | Me | CO—O-allyl | CO₂-Me | H | OMe | OMe | CH | |
| 1.491 | " | " | " | " | " | OMe | N | |
| 1.492 | " | " | " | " | " | Me | N | |
| 1.493 | " | " | " | " | " | " | CH | |
| 1.494 | " | " | " | " | NMe₂ | OCH₂CF₃ | N | |
| 1.495 | " | " | " | " | Me | Me | CH | |
| 1.496 | " | " | " | " | " | " | N | |
| 1.497 | " | " | " | " | Cl | OMe | CH | |
| 1.498 | " | " | " | Me | OMe | OMe | CH | |
| 1.499 | " | " | " | " | " | Me | N | |
| 1.500 | " | " | CO₂-Et | H | OMe | OMe | CH | |
| 1.501 | " | " | " | " | " | Cl | CH | |
| 1.502 | " | " | " | " | Me | Me | CH | |

TABLE 1-continued

| No. | R¹ | R² | R³ | R⁴ | X | Y | Z | m.p. |
|---|---|---|---|---|---|---|---|---|
| 1.503 | " | " | " | " | OMe | Me | N | |
| 1.504 | " | " | " | " | NMe₂ | OCH₂CF₃ | N | |
| 1.505 | " | " | " | Me | OMe | OMe | CH | |
| 1.506 | " | " | " | " | OMe | Me | N | |
| 1.507 | " | " | CO₂-n-Pr | H | OMe | OMe | CH | |
| 1.508 | " | " | " | " | " | " | N | |
| 1.509 | " | " | " | " | OMe | Me | N | |
| 1.510 | " | " | " | " | Me | Me | CH | |
| 1.511 | " | " | " | " | OMe | Cl | CH | |
| 1.512 | " | " | " | Me | Me | OMe | N | |
| 1.513 | " | " | " | " | OMe | OMe | CH | |
| 1.514 | Me | CO—O-allyl | CO₂-i-Pr | H | OMe | OMe | CH | |
| 1.515 | " | " | " | " | " | " | N | |
| 1.516 | " | " | " | " | H | Me | N | |
| 1.517 | " | " | " | " | OMe | Cl | CH | |
| 1.518 | " | " | " | " | Me | Me | CH | |
| 1.519 | " | " | " | " | SMe | NEt₂ | N | |
| 1.520 | " | " | CO₂-i-Pr | Me | OMe | Me | N | |
| 1.521 | " | " | " | " | OMe | OMe | CH | |
| 1.522 | Me | " | CO₂-Allyl | H | OMe | OMe | CH | |
| 1.523 | Et | " | CO₂-Me | H | OMe | OMe | CH | |
| 1.524 | " | " | " | H | OMe | Me | N | |
| 1.525 | " | " | " | " | Me | Me | CH | |
| 1.526 | " | " | " | " | Cl | OMe | CH | |
| 1.527 | " | " | " | Me | OMe | OMe | CH | |
| 1.528 | " | " | " | " | OMe | Me | N | |
| 1.529 | " | " | CO₂-Et | H | OMe | OMe | CH | |
| 1.530 | " | " | " | " | OMe | Me | CH | |
| 1.531 | " | " | " | " | Cl | OMe | CH | |
| 1.532 | " | " | " | " | OMe | Me | N | |
| 1.533 | " | " | " | Me | OMe | OMe | CH | |
| 1.534 | " | " | " | " | " | Me | N | |
| 1.535 | " | " | CO₂-n-Pr | H | OMe | OMe | CH | |
| 1.536 | " | " | " | " | OMe | Me | N | |
| 1.537 | " | " | " | " | OMe | Cl | CH | |
| 1.538 | " | " | " | " | Me | Me | CH | |
| 1.539 | " | " | " | Me | OMe | OMe | CH | |
| 1.540 | " | " | " | " | OMe | Me | N | |
| 1.541 | " | " | CO₂-i-Pr | H | OMe | OMe | CH | |
| 1.542 | " | " | " | " | OMe | Me | N | |
| 1.543 | " | " | " | " | Me | Me | CH | |
| 1.544 | " | " | " | Me | OMe | Me | N | |
| 1.545 | n-Pr | CO—O-allyl | CO₂-Me | H | OMe | OMe | CH | |
| 1.546 | " | " | " | " | " | Cl | CH | |
| 1.547 | " | " | " | " | Me | Me | CH | |
| 1.548 | " | " | " | " | OMe | Me | N | |
| 1.549 | " | " | " | Me | OMe | OMe | CH | |
| 1.550 | " | " | " | " | OMe | Me | N | |
| 1.551 | n-Pr | " | CO₂-Et | H | " | " | N | |
| 1.552 | " | " | " | " | " | OMe | CH | |
| 1.553 | " | " | " | " | Me | Me | CH | |
| 1.554 | " | " | CO₂-n-Pr | " | OMe | OMe | CH | |
| 1.555 | i-Pr | " | CO₂-Me | H | OMe | OMe | CH | |
| 1.556 | " | " | " | " | OMe | Me | N | |
| 1.557 | " | " | " | " | Me | Me | CH | |
| 1.558 | " | " | " | " | Cl | OMe | N | |
| 1.559 | " | " | " | Me | OMe | Me | N | |
| 1.560 | " | " | " | " | " | OMe | CH | |
| 1.561 | Allyl | " | CO₂-Me | H | OMe | OMe | CH | |
| 1.562 | " | " | " | " | " | Cl | CH | |
| 1.563 | " | " | " | " | Me | Me | CH | |
| 1.564 | " | " | " | " | OMe | Me | N | |
| 1.565 | " | " | CO₂-Et | H | OMe | OMe | CH | |
| 1.566 | " | " | CO₂-n-Pr | " | " | " | CH | |
| 1.567 | " | " | CO₂-i-Pr | " | " | " | CH | |
| 1.568 | Me | CO—NH—Et | CO₂-Me | H | OMe | OMe | CH | |
| 1.569 | " | " | " | " | " | OMe | N | |
| 1.570 | " | " | " | " | " | Me | N | |

TABLE 1-continued

| No. | R¹ | R² | R³ | R⁴ | X | Y | Z | m.p. |
|---|---|---|---|---|---|---|---|---|
| 1.571 | " | " | " | " | " | " | CH | |
| 1.572 | " | " | " | " | NMe₂ | OCH₂CF₃ | N | |
| 1.573 | " | " | " | " | Me | Me | CH | |
| 1.574 | " | " | " | " | " | " | N | |
| 1.575 | " | " | " | " | Cl | OMe | CH | |
| 1.576 | " | " | " | Me | OMe | OMe | CH | |
| 1.577 | " | " | " | " | " | Me | N | |
| 1.578 | " | " | CO₂-Et | H | OMe | OMe | CH | |
| 1.579 | " | " | " | " | " | Cl | CH | |
| 1.580 | " | " | " | " | Me | Me | CH | |
| 1.581 | " | " | " | " | OMe | Me | N | |
| 1.582 | " | " | " | " | NMe₂ | OCH₂CF₃ | N | |
| 1.583 | " | " | " | Me | OMe | OMe | CH | |
| 1.584 | " | " | " | " | OMe | Me | N | |
| 1.585 | " | " | CO₂-n-Pr | H | OMe | OMe | CH | |
| 1.586 | " | " | " | " | " | " | N | |
| 1.587 | " | " | " | " | OMe | Me | N | |
| 1.588 | " | " | " | " | Me | Me | CH | |
| 1.589 | " | " | " | " | OMe | Cl | CH | |
| 1.590 | " | " | " | Me | Me | OMe | N | |
| 1.591 | " | " | " | " | OMe | OMe | CH | |
| 1.592 | Me | CO—NHEt | CO₂-i-Pr | H | OMe | OMe | CH | |
| 1.593 | " | " | " | " | " | " | N | |
| 1.594 | " | " | " | " | OMe | Me | N | |
| 1.595 | " | " | " | " | OMe | Cl | CH | |
| 1.596 | " | " | " | " | Me | Me | CH | |
| 1.597 | " | " | " | " | SMe | NEt₂ | N | |
| 1.598 | " | " | CO₂-i-Pr | Me | OMe | Me | N | |
| 1.599 | " | " | " | " | OMe | OMe | CH | |
| 1.600 | Me | " | CO₂-Allyl | H | OMe | OMe | CH | |
| 1.601 | Et | " | CO₂-Me | H | OMe | OMe | CH | |
| 1.602 | " | " | " | H | OMe | Me | N | |
| 1.603 | " | " | " | " | Me | Me | CH | |
| 1.604 | " | " | " | " | Cl | OMe | CH | |
| 1.605 | " | " | " | Me | OMe | OMe | CH | |
| 1.606 | " | " | " | " | OMe | Me | N | |
| 1.607 | " | " | CO₂-Et | H | OMe | OMe | CH | |
| 1.608 | " | " | " | " | OMe | Me | CH | |
| 1.609 | " | " | " | " | Cl | OMe | CH | |
| 1.610 | " | " | " | " | OMe | Me | N | |
| 1.611 | " | " | " | Me | OMe | OMe | CH | |
| 1.612 | " | " | " | " | " | Me | N | |
| 1.613 | " | " | CO₂-n-Pr | H | OMe | OMe | CH | |
| 1.614 | " | " | " | " | OMe | Me | N | |
| 1.615 | " | " | " | " | OMe | Cl | CH | |
| 1.616 | " | " | " | " | Me | Me | CH | |
| 1.617 | " | " | " | Me | OMe | OMe | CH | |
| 1.618 | " | " | " | " | OMe | Me | N | |
| 1.619 | " | " | CO₂-i-Pr | H | OMe | OMe | CH | |
| 1.620 | " | " | " | " | OMe | Me | N | |
| 1.621 | " | " | " | " | Me | Me | CH | |
| 1.622 | " | " | " | Me | OMe | Me | N | |
| 1.623 | n-Pr | CO—NHEt | CO₂-Me | H | OMe | OMe | CH | |
| 1.624 | " | " | " | " | " | Cl | CH | |
| 1.625 | " | " | " | " | Me | Me | CH | |
| 1.626 | " | " | " | " | OMe | Me | N | |
| 1.627 | " | " | " | Me | OMe | OMe | CH | |
| 1.628 | " | " | " | " | OMe | Me | N | |
| 1.629 | n-Pr | " | CO₂-Et | H | " | " | N | |
| 1.630 | " | " | " | " | " | OMe | CH | |
| 1.631 | " | " | " | " | Me | Me | CH | |
| 1.632 | " | " | CO₂-n-Pr | " | OMe | OMe | CH | |
| 1.633 | i-Pr | " | CO₂-Me | H | OMe | OMe | CH | |
| 1.634 | " | " | " | " | OMe | Me | N | |
| 1.635 | " | " | " | " | Me | Me | CH | |
| 1.636 | " | " | " | " | Cl | OMe | N | |
| 1.637 | " | " | " | Me | OMe | Me | N | |
| 1.638 | " | " | " | " | " | OMe | CH | |

TABLE 1-continued

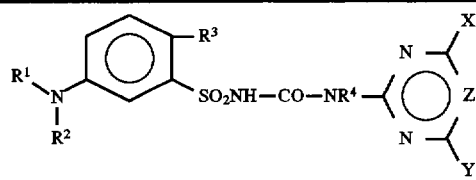

| No. | R¹ | R² | R³ | R⁴ | X | Y | Z | m.p. |
|---|---|---|---|---|---|---|---|---|
| 1.639 | Allyl | " | CO₂-Me | H | OMe | OMe | CH | |
| 1.640 | " | " | " | " | " | Cl | CH | |
| 1.641 | " | " | " | " | Me | Me | CH | |
| 1.642 | " | " | " | " | OMe | Me | N | |
| 1.643 | " | " | CO₂-Et | H | OMe | OMe | CH | |
| 1.644 | " | " | CO₂-n-Pr | " | " | " | CH | |
| 1.645 | " | " | CO₂-i-Pr | " | " | " | CH | |
| 1.646 | Me | CO—NHPr | CO₂-Me | H | " | " | CH | |
| 1.647 | " | " | " | " | " | OMe | N | |
| 1.648 | " | " | " | " | " | Me | N | |
| 1.649 | " | " | " | " | " | " | CH | |
| 1.650 | " | " | " | " | NMe₂ | OCH₂CF₃ | N | |
| 1.651 | " | " | " | " | Me | Me | CH | |
| 1.652 | " | " | " | " | " | " | N | |
| 1.653 | " | " | " | " | Cl | OMe | CH | |
| 1.654 | " | " | " | Me | OMe | OMe | CH | |
| 1.655 | " | " | " | " | " | Me | N | |
| 1.656 | " | " | CO₂-Et | H | OMe | OMe | CH | |
| 1.657 | " | " | " | " | " | Cl | CH | |
| 1.658 | " | " | " | " | Me | Me | CH | |
| 1.659 | " | " | " | " | OMe | Me | N | |
| 1.660 | " | " | " | " | NMe₂ | OCH₂CF₃ | N | |
| 1.661 | " | " | " | Me | OMe | OMe | CH | |
| 1.662 | " | " | " | " | OMe | Me | N | |
| 1.663 | " | " | CO₂-n-Pr | H | OMe | OMe | CH | |
| 1.664 | " | " | " | " | " | " | N | |
| 1.665 | " | " | " | " | OMe | Me | N | |
| 1.666 | " | " | " | " | Me | Me | CH | |
| 1.667 | " | " | " | " | OMe | Cl | CH | |
| 1.668 | " | " | " | Me | Me | OMe | N | |
| 1.669 | " | " | " | " | OMe | OMe | CH | |
| 1.670 | Me | CONHPr | CO₂-i-Pr | H | OMe | OMe | CH | |
| 1.671 | " | " | " | " | " | " | N | |
| 1.672 | " | " | " | " | OMe | Me | N | |
| 1.673 | " | " | " | " | OMe | Cl | CH | |
| 1.674 | " | " | " | " | Me | Me | CH | |
| 1.675 | " | " | " | " | SMe | NEt₂ | N | |
| 1.676 | " | " | CO₂-i-Pr | Me | OMe | Me | N | |
| 1.677 | " | " | " | " | OMe | OMe | CH | |
| 1.678 | Me | " | CO₂-Allyl | H | OMe | OMe | CH | |
| 1.679 | Et | " | CO₂-Me | H | OMe | OMe | CH | |
| 1.680 | " | " | " | H | OMe | Me | N | |
| 1.681 | " | " | " | " | Me | Me | CH | |
| 1.682 | " | " | " | " | Cl | OMe | CH | |
| 1.683 | " | " | " | Me | OMe | OMe | CH | |
| 1.684 | " | " | " | " | OMe | Me | N | |
| 1.685 | " | " | CO₂-Et | H | OMe | OMe | CH | |
| 1.686 | " | " | " | " | OMe | Me | CH | |
| 1.687 | " | " | " | " | Cl | OMe | CH | |
| 1.688 | " | " | " | " | OMe | Me | N | |
| 1.689 | " | " | " | Me | OMe | OMe | CH | |
| 1.690 | " | " | " | " | " | Me | N | |
| 1.691 | " | " | CO₂-n-Pr | H | OMe | OMe | CH | |
| 1.692 | " | " | " | " | OMe | Me | N | |
| 1.693 | " | " | " | " | OMe | Cl | CH | |
| 1.694 | " | " | " | " | Me | Me | CH | |
| 1.695 | " | " | " | Me | OMe | OMe | CH | |
| 1.696 | " | " | " | " | OMe | Me | N | |
| 1.697 | " | " | CO₂-i-Pr | H | OMe | OMe | CH | |
| 1.698 | " | " | " | " | OMe | Me | N | |
| 1.699 | " | " | " | " | Me | Me | CH | |
| 1.700 | " | " | " | Me | OMe | Me | N | |
| 1.701 | n-Pr | " | CO₂Me | H | OMe | OMe | CH | |
| 1.702 | " | " | " | " | " | Cl | CH | |
| 1.703 | " | " | " | " | Me | Me | CH | |
| 1.704 | " | " | " | " | OMe | Me | N | |
| 1.705 | " | " | " | Me | OMe | OMe | CH | |
| 1.706 | " | " | " | " | OMe | Me | N | |

TABLE 1-continued

| No. | R¹ | R² | R³ | R⁴ | X | Y | Z | m.p. |
|---|---|---|---|---|---|---|---|---|
| 1.707 | n-Pr | " | CO₂-Et | H | " | " | N | |
| 1.708 | " | " | " | " | " | OMe | CH | |
| 1.709 | " | " | " | " | Me | Me | CH | |
| 1.710 | " | " | CO₂-n-Pr | " | OMe | OMe | CH | |
| 1.711 | i-Pr | " | CO₂-Me | H | OMe | OMe | CH | |
| 1.712 | " | " | " | " | OMe | Me | N | |
| 1.713 | " | " | " | " | Me | Me | CH | |
| 1.714 | " | " | " | " | Cl | OMe | N | |
| 1.715 | " | " | " | Me | OMe | Me | N | |
| 1.716 | " | " | " | " | " | OMe | CH | |
| 1.717 | Allyl | " | CO₂-Me | H | OMe | OMe | CH | |
| 1.718 | " | " | " | " | " | Cl | CH | |
| 1.719 | " | " | " | " | Me | Me | CH | |
| 1.720 | " | " | " | " | OMe | Me | N | |
| 1.721 | " | " | CO₂-Et | H | OMe | OMe | CH | |
| 1.722 | " | " | CO₂-n-Pr | " | " | " | CH | |
| 1.723 | " | " | CO₂-i-Pr | " | " | " | CH | |
| 1.724 | Me | CONH-allyl | CO₂-Me | H | OMe | OMe | CH | |
| 1.725 | " | " | " | " | " | OMe | N | |
| 1.726 | " | " | " | " | " | Me | N | |
| 1.727 | " | " | " | " | " | " | CH | |
| 1.728 | " | " | " | " | NMe₂ | OCH₂CF₃ | N | |
| 1.729 | " | " | " | " | Me | Me | CH | |
| 1.730 | " | " | " | " | " | " | N | |
| 1.731 | " | " | " | " | Cl | OMe | CH | |
| 1.732 | " | " | " | Me | OMe | OMe | CH | |
| 1.733 | " | " | " | " | " | Me | N | |
| 1.734 | " | " | CO₂-Et | H | OMe | OMe | CH | |
| 1.735 | " | " | " | " | " | Cl | CH | |
| 1.736 | " | " | " | " | Me | Me | CH | |
| 1.737 | " | " | " | " | OMe | Me | N | |
| 1.738 | " | " | " | " | NMe₂ | OCH₂CF₃ | N | |
| 1.739 | " | " | " | Me | OMe | OMe | CH | |
| 1.740 | " | " | " | " | OMe | Me | N | |
| 1.741 | " | " | CO₂-n-Pr | H | OMe | OMe | CH | |
| 1.742 | " | " | " | " | " | " | N | |
| 1.743 | " | " | " | " | OMe | Me | N | |
| 1.744 | " | " | " | " | Me | Me | CH | |
| 1.745 | " | " | " | " | OMe | Cl | CH | |
| 1.746 | " | " | " | Me | Me | OMe | N | |
| 1.747 | " | " | " | " | OMe | OMe | CH | |
| 1.748 | Me | CONH-allyl | CO₂-i-Pr | H | OMe | OMe | CH | |
| 1.749 | " | " | " | " | " | " | N | |
| 1.750 | " | " | " | " | OMe | Me | N | |
| 1.751 | " | " | " | " | OMe | Cl | CH | |
| 1.752 | " | " | " | " | Me | Me | CH | |
| 1.753 | " | " | " | " | SMe | NEt₂ | N | |
| 1.754 | " | " | CO₂-i-Pr | Me | OMe | Me | N | |
| 1.755 | " | " | " | " | OMe | OMe | CH | |
| 1.756 | Me | " | CO₂-Allyl | H | OMe | OMe | CH | |
| 1.757 | Et | " | CO₂-Me | H | OMe | OMe | CH | |
| 1.758 | " | " | " | H | OMe | Me | N | |
| 1.759 | " | " | " | " | Me | Me | CH | |
| 1.760 | " | " | " | " | Cl | OMe | CH | |
| 1.761 | " | " | " | Me | OMe | OMe | CH | |
| 1.762 | " | " | " | " | OMe | Me | N | |
| 1.763 | " | " | CO₂-Et | H | OMe | OMe | CH | |
| 1.764 | " | " | " | " | OMe | Me | CH | |
| 1.765 | " | " | " | " | Cl | OMe | CH | |
| 1.766 | " | " | " | " | OMe | Me | N | |
| 1.767 | " | " | " | Me | OMe | OMe | CH | |
| 1.768 | " | " | " | " | " | Me | N | |
| 1.769 | " | " | CO₂-n-Pr | H | OMe | OMe | CH | |
| 1.770 | " | " | " | " | OMe | Me | N | |
| 1.771 | " | " | " | " | OMe | Cl | CH | |
| 1.772 | " | " | " | " | Me | Me | CH | |
| 1.773 | " | " | " | Me | OMe | OMe | CH | |
| 1.774 | " | " | " | " | OMe | Me | N | |

TABLE 1-continued

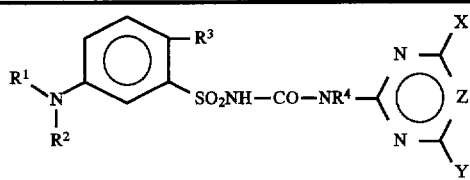

| No. | R¹ | R² | R³ | R⁴ | X | Y | Z | m.p. |
|---|---|---|---|---|---|---|---|---|
| 1.775 | " | " | CO₂-i-Pr | H | OMe | OMe | CH | |
| 1.776 | " | " | " | " | OMe | Me | N | |
| 1.777 | " | " | " | " | Me | Me | CH | |
| 1.778 | " | " | " | Me | OMe | Me | N | |
| 1.779 | n-Pr | CO—NH-allyl | CO₂-Me | H | OMe | OMe | CH | |
| 1.780 | " | " | " | " | " | Cl | CH | |
| 1.781 | " | " | " | " | Me | Me | CH | |
| 1.782 | " | " | " | " | OMe | Me | N | |
| 1.783 | " | " | " | Me | OMe | OMe | CH | |
| 1.784 | " | " | " | " | OMe | Me | N | |
| 1.785 | n-Pr | " | CO₂-Et | H | OMe | Me | N | |
| 1.786 | " | " | " | " | " | OMe | CH | |
| 1.787 | " | " | " | " | Me | Me | CH | |
| 1.788 | " | " | CO₂-n-Pr | " | OMe | OMe | CH | |
| 1.789 | i-Pr | " | CO₂-Me | H | OMe | OMe | CH | |
| 1.790 | " | " | " | " | OMe | Me | N | |
| 1.791 | " | " | " | " | Me | Me | CH | |
| 1.792 | " | " | " | " | Cl | OMe | N | |
| 1.793 | " | " | " | Me | OMe | Me | N | |
| 1.794 | " | " | " | " | " | OMe | CH | |
| 1.795 | Allyl | " | CO₂-Me | H | OMe | OMe | CH | |
| 1.796 | " | " | " | " | " | Cl | CH | |
| 1.797 | " | " | " | " | Me | Me | CH | |
| 1.798 | " | " | " | " | OMe | Me | N | |
| 1.799 | " | " | CO₂-Et | H | OMe | OMe | CH | |
| 1.800 | " | " | CO₂-n-Pr | " | " | " | " | |
| 1.801 | " | " | CO₂-i-Pr | " | " | " | " | |
| 1.802 | Me | CS—NHMe | CO₂-Me | H | OMe | OMe | CH | 190–193 |
| 1.803 | " | " | " | " | " | OMe | N | |
| 1.804 | " | " | " | " | " | Me | N | |
| 1.805 | " | " | " | " | " | " | CH | |
| 1.806 | " | " | " | " | NMe₂ | OCH₂CF₃ | N | |
| 1.807 | " | " | " | " | Me | Me | CH | |
| 1.808 | " | " | " | " | " | " | N | |
| 1.809 | " | " | " | " | Cl | OMe | CH | |
| 1.810 | " | " | " | Me | OMe | OMe | CH | |
| 1.811 | " | " | " | " | " | Me | N | |
| 1.812 | " | " | CO₂-Et | H | OMe | OMe | CH | |
| 1.813 | " | " | " | " | " | Cl | CH | |
| 1.814 | " | " | " | " | Me | Me | CH | |
| 1.815 | " | " | " | " | OMe | Me | N | |
| 1.816 | " | " | " | " | NMe₂ | OCH₂CF₃ | N | |
| 1.817 | " | " | " | Me | OMe | OMe | CH | |
| 1.818 | " | " | " | " | OMe | Me | N | |
| 1.819 | " | " | CO₂-n-Pr | H | OMe | OMe | CH | |
| 1.820 | " | " | " | " | " | " | N | |
| 1.821 | " | " | " | " | OMe | Me | N | |
| 1.822 | " | " | " | " | Me | Me | CH | |
| 1.823 | " | " | " | " | OMe | Cl | CH | |
| 1.824 | " | " | " | Me | Me | OMe | N | |
| 1.825 | " | " | " | " | OMe | OMe | CH | |
| 1.826 | Me | CS—NHMe | CO₂-i-Pr | H | OMe | OMe | CH | |
| 1.827 | " | " | " | " | " | " | N | |
| 1.828 | " | " | " | " | OMe | Me | N | |
| 1.829 | " | " | " | " | OMe | Cl | CH | |
| 1.830 | " | " | " | " | Me | Me | CH | |
| 1.831 | " | " | " | " | SMe | NEt₂ | N | |
| 1.832 | " | " | CO₂-i-Pr | Me | OMe | Me | N | |
| 1.833 | " | " | " | " | OMe | OMe | CH | |
| 1.834 | Me | " | CO₂-Allyl | H | OMe | OMe | CH | |
| 1.835 | Et | " | CO₂-Me | H | OMe | OMe | CH | |
| 1.836 | " | " | " | H | OMe | Me | N | |
| 1.837 | " | " | " | " | Me | Me | CH | |
| 1.838 | " | " | " | " | Cl | OMe | CH | |
| 1.839 | " | " | " | Me | OMe | OMe | CH | |
| 1.840 | " | " | " | " | OMe | Me | N | |
| 1.841 | " | " | CO₂-Et | H | OMe | OMe | CH | |
| 1.842 | " | " | " | " | OMe | Me | CH | |

TABLE 1-continued

| No. | R¹ | R² | R³ | R⁴ | X | Y | Z | m.p. |
|---|---|---|---|---|---|---|---|---|
| 1.843 | " | " | " | " | Cl | OMe | CH | |
| 1.844 | " | " | " | " | OMe | Me | N | |
| 1.845 | " | " | " | Me | OMe | OMe | CH | |
| 1.846 | " | " | " | " | " | Me | N | |
| 1.847 | " | " | CO₂-n-Pr | H | OMe | OMe | CH | |
| 1.848 | " | " | " | " | OMe | Me | N | |
| 1.849 | " | " | " | " | OMe | Cl | CH | |
| 1.850 | " | " | " | " | Me | Me | CH | |
| 1.851 | " | " | " | Me | OMe | OMe | CH | |
| 1.852 | " | " | " | " | OMe | Me | N | |
| 1.853 | " | " | CO₂-i-Pr | H | OMe | OMe | CH | |
| 1.854 | " | " | " | " | OMe | Me | N | |
| 1.855 | " | " | " | " | Me | Me | CH | |
| 1.856 | " | " | " | Me | OMe | Me | N | |
| 1.857 | n-Pr | CS—NHMe | CO₂-Me | H | OMe | OMe | CH | |
| 1.858 | " | " | " | " | " | Cl | CH | |
| 1.859 | " | " | " | " | Me | Me | CH | |
| 1.860 | " | " | " | " | OMe | Me | N | |
| 1.861 | " | " | " | Me | OMe | OMe | CH | |
| 1.862 | " | " | " | " | OMe | Me | N | |
| 1.863 | n-Pr | " | CO₂-Et | H | " | " | N | |
| 1.864 | " | " | " | " | " | OMe | CH | |
| 1.865 | " | " | " | " | Me | Me | CH | |
| 1.866 | " | " | CO₂-n-Pr | " | OMe | OMe | CH | |
| 1.867 | i-Pr | " | CO₂-Me | H | OMe | OMe | CH | |
| 1.868 | " | " | " | " | OMe | Me | N | |
| 1.869 | " | " | " | " | Me | Me | CH | |
| 1.870 | " | " | " | " | Cl | OMe | N | |
| 1.871 | " | " | " | Me | OMe | Me | N | |
| 1.872 | " | " | " | " | " | OMe | CH | |
| 1.873 | Allyl | " | CO₂-Me | H | OMe | OMe | CH | |
| 1.874 | " | " | " | " | " | Cl | CH | |
| 1.875 | " | " | " | " | Me | Me | CH | |
| 1.876 | " | " | " | " | OMe | Me | N | |
| 1.877 | " | " | CO₂-Et | H | OMe | OMe | CH | |
| 1.878 | " | " | CO₂-n-Pr | H | OMe | OMe | CH | |
| 1.879 | " | " | CO₂-i-Pr | " | " | " | " | |
| 1.880 | Me | CS—NHEt | CO₂-Me | H | OMe | OMe | CH | |
| 1.881 | " | " | " | " | " | OMe | N | |
| 1.882 | " | " | " | " | " | Me | N | |
| 1.883 | " | " | " | " | " | " | CH | |
| 1.884 | " | " | " | " | NMe₂ | OCH₂CF₃ | N | |
| 1.885 | " | " | " | " | Me | Me | CH | |
| 1.886 | " | " | " | " | " | " | N | |
| 1.887 | " | " | " | " | Cl | OMe | CH | |
| 1.888 | " | " | " | Me | OMe | OMe | CH | |
| 1.889 | " | " | " | " | " | Me | N | |
| 1.890 | " | " | CO₂-Et | H | OMe | OMe | CH | |
| 1.891 | " | " | " | " | " | Cl | CH | |
| 1.892 | " | " | " | " | Me | Me | CH | |
| 1.893 | " | " | " | " | OMe | Me | N | |
| 1.894 | " | " | " | " | NMe₂ | OCH₂CF₃ | N | |
| 1.895 | " | " | " | Me | OMe | OMe | CH | |
| 1.896 | " | " | " | " | OMe | Me | N | |
| 1.897 | " | " | CO₂-n-Pr | H | OMe | OMe | CH | |
| 1.898 | " | " | " | " | " | " | N | |
| 1.899 | " | " | " | " | OMe | Me | N | |
| 1.900 | " | " | " | " | Me | Me | CH | |
| 1.901 | " | " | " | " | OMe | Cl | CH | |
| 1.902 | " | " | " | Me | Me | OMe | N | |
| 1.903 | " | " | " | " | OMe | OMe | CH | |
| 1.904 | Me | CS—NHEt | CO₂-i-Pr | H | OMe | OMe | CH | |
| 1.905 | " | " | " | " | " | " | N | |
| 1.906 | " | " | " | " | OMe | Me | N | |
| 1.907 | " | " | " | " | OMe | Cl | CH | |
| 1.908 | " | " | " | " | Me | Me | CH | |
| 1.909 | " | " | " | " | SMe | NEt₂ | N | |
| 1.910 | " | " | CO₂-i-Pr | Me | OMe | Me | N | |

TABLE 1-continued

| No. | R¹ | R² | R³ | R⁴ | X | Y | Z | m.p. |
|---|---|---|---|---|---|---|---|---|
| 1.911 | " | " | " | " | OMe | OMe | CH | |
| 1.912 | Me | " | CO₂-Allyl | H | OMe | OMe | CH | |
| 1.913 | Et | " | CO₂-Me | H | OMe | OMe | CH | |
| 1.914 | " | " | " | H | OMe | Me | N | |
| 1.915 | " | " | " | " | Me | Me | CH | |
| 1.916 | " | " | " | " | Cl | OMe | CH | |
| 1.917 | " | " | " | Me | OMe | OMe | CH | |
| 1.918 | " | " | " | " | OMe | Me | N | |
| 1.919 | " | " | CO₂-Et | H | OMe | OMe | CH | |
| 1.920 | " | " | " | " | " | Me | CH | |
| 1.921 | " | " | " | " | Cl | OMe | CH | |
| 1.922 | " | " | " | " | OMe | Me | N | |
| 1.923 | " | " | " | Me | OMe | OMe | CH | |
| 1.924 | " | " | " | " | " | Me | N | |
| 1.925 | " | " | CO₂-n-Pr | H | OMe | OMe | CH | |
| 1.926 | " | " | " | " | OMe | Me | N | |
| 1.927 | " | " | " | " | OMe | Cl | CH | |
| 1.928 | " | " | " | " | Me | Me | CH | |
| 1.929 | " | " | " | Me | OMe | OMe | CH | |
| 1.930 | " | " | " | " | OMe | Me | N | |
| 1.931 | " | " | CO₂-i-Pr | H | OMe | OMe | CH | |
| 1.932 | " | " | " | " | OMe | Me | N | |
| 1.933 | " | " | " | " | Me | Me | CH | |
| 1.934 | " | " | " | Me | OMe | Me | N | |
| 1.935 | n-Pr | CS—NHEt | CO₂-Me | H | OMe | OMe | CH | |
| 1.936 | " | " | " | " | " | Cl | CH | |
| 1.937 | " | " | " | " | Me | Me | CH | |
| 1.938 | " | " | " | " | OMe | Me | N | |
| 1.939 | " | " | " | Me | OMe | OMe | CH | |
| 1.940 | " | " | " | " | OMe | Me | N | |
| 1.941 | n-Pr | " | CO₂-Et | H | " | " | N | |
| 1.942 | " | " | " | " | " | OMe | CH | |
| 1.943 | " | " | " | " | Me | Me | CH | |
| 1.944 | " | " | CO₂-n-Pr | " | OMe | OMe | CH | |
| 1.945 | i-Pr | " | CO₂-Me | H | OMe | OMe | CH | |
| 1.946 | " | " | " | " | OMe | Me | N | |
| 1.947 | " | " | " | " | Me | Me | CH | |
| 1.948 | " | " | " | " | Cl | OMe | N | |
| 1.949 | " | " | " | Me | OMe | Me | N | |
| 1.950 | " | " | " | " | OMe | OMe | CH | |
| 1.951 | Allyl | " | CO₂-Me | H | OMe | OMe | CH | |
| 1.952 | " | " | " | " | " | Cl | CH | |
| 1.953 | " | " | " | " | Me | Me | CH | |
| 1.954 | " | " | " | " | OMe | Me | N | |
| 1.955 | " | " | CO₂-Et | H | OMe | OMe | CH | |
| 1.956 | " | " | CO₂-n-Pr | " | " | " | CH | |
| 1.957 | " | " | CO₂-i-Pr | " | " | " | CH | |
| 1.958 | Me | CS—NH-n-Pr | CO₂-Me | H | OMe | OMe | CH | |
| 1.959 | " | " | " | " | " | OMe | N | |
| 1.960 | " | " | " | " | " | Me | N | |
| 1.961 | " | " | " | " | " | " | CH | |
| 1.962 | " | " | " | " | NMe₂ | OCH₂CF₃ | N | |
| 1.963 | " | " | " | " | Me | Me | CH | |
| 1.964 | " | " | " | " | " | " | N | |
| 1.965 | " | " | " | " | Cl | OMe | CH | |
| 1.966 | " | " | " | Me | OMe | OMe | CH | |
| 1.967 | " | " | " | " | " | Me | N | |
| 1.968 | " | " | CO₂-Et | H | OMe | OMe | CH | |
| 1.969 | " | " | " | " | " | Cl | CH | |
| 1.970 | " | " | " | " | Me | Me | CH | |
| 1.971 | " | " | " | " | OMe | Me | N | |
| 1.972 | " | " | " | " | NMe₂ | OCH₂CF₃ | N | |
| 1.973 | " | " | " | Me | OMe | OMe | CH | |
| 1.974 | " | " | " | " | OMe | Me | N | |
| 1.975 | " | " | CO₂-n-Pr | H | OMe | OMe | CH | |
| 1.976 | " | " | " | " | " | " | N | |
| 1.977 | " | " | " | " | OMe | Me | N | |
| 1.978 | " | " | " | " | Me | Me | CH | |

TABLE 1-continued

| No. | R¹ | R² | R³ | R⁴ | X | Y | Z | m.p. |
|---|---|---|---|---|---|---|---|---|
| 1.979 | " | " | " | " | OMe | Cl | CH | |
| 1.980 | " | " | " | Me | Me | OMe | N | |
| 1.981 | " | " | " | " | OMe | OMe | CH | |
| 1.982 | Me | CS—NH-n-Pr | CO₂-i-Pr | H | OMe | OMe | CH | |
| 1.983 | " | " | " | " | " | " | N | |
| 1.984 | " | " | " | " | OMe | Me | N | |
| 1.985 | " | " | " | " | OMe | Cl | CH | |
| 1.986 | " | " | " | " | Me | Me | CH | |
| 1.987 | " | " | " | " | SMe | NEt₂ | N | |
| 1.988 | " | " | CO₂-i-Pr | Me | OMe | Me | N | |
| 1.989 | " | " | " | " | OMe | OMe | CH | |
| 1.990 | Me | " | CO₂-Allyl | H | OMe | OMe | CH | |
| 1.991 | Et | " | CO₂-Me | H | OMe | OMe | CH | |
| 1.992 | " | " | " | H | OMe | Me | N | |
| 1.993 | " | " | " | " | Me | Me | CH | |
| 1.994 | " | " | " | " | Cl | OMe | CH | |
| 1.995 | " | " | " | Me | OMe | OMe | CH | |
| 1.996 | " | " | " | " | OMe | Me | N | |
| 1.997 | " | " | CO₂-Et | H | OMe | OMe | CH | |
| 1.998 | " | " | " | " | OMe | Me | CH | |
| 1.999 | " | " | " | " | Cl | OMe | CH | |
| 2.000 | " | " | " | " | OMe | Me | N | |
| 2.001 | " | " | " | Me | OMe | OMe | CH | |
| 2.002 | " | " | " | " | " | Me | N | |
| 2.003 | " | " | CO₂-n-Pr | H | OMe | OMe | CH | |
| 2.004 | " | " | " | " | OMe | Me | N | |
| 2.005 | " | " | " | " | OMe | Cl | CH | |
| 2.006 | " | " | " | " | Me | Me | CH | |
| 2.007 | " | " | " | Me | OMe | OMe | CH | |
| 2.008 | " | " | " | " | OMe | Me | N | |
| 2.009 | " | " | CO₂-i-Pr | H | OMe | OMe | CH | |
| 2.010 | " | " | " | " | OMe | Me | N | |
| 2.011 | " | " | " | " | Me | Me | CH | |
| 2.012 | " | " | " | Me | OMe | Me | N | |
| 2.013 | n-Pr | CS—NH-n-Pr | CO₂-Me | H | OMe | OMe | CH | |
| 2.014 | " | " | " | " | " | Cl | CH | |
| 2.015 | " | " | " | " | Me | Me | CH | |
| 2.016 | " | " | " | " | OMe | Me | N | |
| 2.017 | " | " | " | Me | OMe | OMe | CH | |
| 2.018 | " | " | " | " | OMe | Me | N | |
| 2.019 | n-Pr | " | CO₂-Et | H | " | " | N | |
| 2.020 | " | " | " | " | " | OMe | CH | |
| 2.021 | " | " | " | " | Me | Me | CH | |
| 2.022 | " | " | CO₂-n-Pr | " | OMe | OMe | CH | |
| 2.023 | i-Pr | " | CO₂-Me | H | " | " | CH | |
| 2.024 | " | " | " | " | " | Me | N | |
| 2.025 | " | " | " | " | Me | Me | CH | |
| 2.026 | " | " | " | " | Cl | OMe | N | |
| 2.027 | " | " | " | Me | OMe | Me | N | |
| 2.028 | " | " | " | " | " | OMe | CH | |
| 2.029 | Allyl | " | CO₂-Me | H | OMe | OMe | CH | |
| 2.030 | " | " | " | " | " | Cl | CH | |
| 2.031 | " | " | " | " | Me | Me | CH | |
| 2.032 | " | " | " | " | OMe | Me | N | |
| 2.033 | " | " | CO₂-Et | H | OMe | OMe | CH | |
| 2.034 | " | " | CO₂-n-Pr | " | " | " | CH | |
| 2.035 | " | " | CO₂-i-Pr | " | " | " | CH | |
| 2.036 | Me | CS—NH-i-Pr | CO₂-Me | H | OMe | OMe | CH | |
| 2.037 | " | " | " | " | " | OMe | N | |
| 2.038 | " | " | " | " | " | Me | N | |
| 2.039 | " | " | " | " | " | " | CH | |
| 2.040 | " | " | " | " | NMe₂ | OCH₂CF₃ | N | |
| 2.041 | " | " | " | " | Me | Me | CH | |
| 2.042 | " | " | " | " | " | " | N | |
| 2.043 | " | " | " | " | Cl | OMe | CH | |
| 2.044 | " | " | " | Me | OMe | OMe | CH | |
| 2.045 | " | " | " | " | " | Me | N | |
| 2.046 | " | " | CO₂-Et | H | OMe | OMe | CH | |

TABLE 1-continued

| No. | R¹ | R² | R³ | R⁴ | X | Y | Z | m.p. |
|---|---|---|---|---|---|---|---|---|
| 2.047 | " | " | " | " | " | Cl | CH | |
| 2.048 | " | " | " | " | Me | Me | CH | |
| 2.049 | " | " | " | " | OMe | Me | N | |
| 2.050 | " | " | " | " | NMe₂ | OCH₂CF₃ | N | |
| 2.051 | " | " | " | Me | OMe | OMe | CH | |
| 2.052 | " | " | " | " | OMe | Me | N | |
| 2.053 | " | " | CO₂-n-Pr | H | OMe | OMe | CH | |
| 2.054 | " | " | " | " | " | " | N | |
| 2.055 | " | " | " | " | OMe | Me | N | |
| 2.056 | " | " | " | " | Me | Me | CH | |
| 2.057 | " | " | " | " | OMe | Cl | CH | |
| 2.058 | " | " | " | Me | Me | OMe | N | |
| 2.059 | " | " | " | " | OMe | OMe | CH | |
| 2.060 | Me | CS—NH-i-Pr | CO₂-i-Pr | H | OMe | OMe | CH | |
| 2.061 | " | " | " | " | " | " | N | |
| 2.062 | " | " | " | " | OMe | Me | N | |
| 2.063 | " | " | " | " | OMe | Cl | CH | |
| 2.064 | " | " | " | " | Me | Me | CH | |
| 2.065 | " | " | " | " | SMe | NEt₂ | N | |
| 2.066 | " | " | CO₂-i-Pr | Me | OMe | Me | N | |
| 2.067 | " | " | " | " | OMe | OMe | CH | |
| 2.068 | Me | " | CO₂-Allyl | H | OMe | OMe | CH | |
| 2.069 | Et | " | CO₂-Me | H | OMe | OMe | CH | |
| 2.070 | " | " | " | H | OMe | Me | N | |
| 2.071 | " | " | " | " | Me | Me | CH | |
| 2.072 | " | " | " | " | Cl | OMe | CH | |
| 2.073 | " | " | " | Me | OMe | OMe | CH | |
| 2.074 | " | " | " | " | OMe | Me | N | |
| 2.075 | " | " | CO₂-Et | H | OMe | OMe | CH | |
| 2.076 | " | " | " | " | OMe | Me | CH | |
| 2.077 | " | " | " | " | Cl | OMe | CH | |
| 2.078 | " | " | " | " | OMe | Me | N | |
| 2.079 | " | " | " | Me | OMe | OMe | CH | |
| 2.080 | " | " | " | " | " | Me | N | |
| 2.081 | " | " | CO₂-n-Pr | H | OMe | OMe | CH | |
| 2.082 | " | " | " | " | OMe | Me | N | |
| 2.083 | " | " | " | " | OMe | Cl | CH | |
| 2.084 | " | " | " | " | Me | Me | CH | |
| 2.085 | " | " | " | Me | OMe | OMe | CH | |
| 2.086 | " | " | " | " | OMe | Me | N | |
| 2.087 | " | " | CO₂-i-Pr | H | OMe | OMe | CH | |
| 2.088 | " | " | " | " | OMe | Me | N | |
| 2.089 | " | " | " | " | Me | Me | CH | |
| 2.090 | " | " | " | Me | OMe | Me | N | |
| 2.091 | n-Pr | CS—NH-i-Pr | CO₂-Me | H | OMe | OMe | CH | |
| 2.092 | " | " | " | " | " | Cl | CH | |
| 2.093 | " | " | " | " | Me | Me | CH | |
| 2.094 | " | " | " | " | OMe | Me | N | |
| 2.095 | " | " | " | Me | OMe | OMe | CH | |
| 2.096 | " | " | " | " | OMe | Me | N | |
| 2.097 | n-Pr | " | CO₂-Et | H | " | " | N | |
| 2.098 | " | " | " | " | " | OMe | CH | |
| 2.099 | " | " | " | " | Me | Me | CH | |
| 2.100 | " | " | CO₂-n-Pr | " | OMe | OMe | CH | |
| 2.101 | i-Pr | " | CO₂-Me | H | OMe | OMe | CH | |
| 2.102 | " | " | " | " | OMe | Me | N | |
| 2.103 | " | " | " | " | Me | Me | CH | |
| 2.104 | " | " | " | " | Cl | OMe | N | |
| 2.105 | " | " | " | Me | OMe | Me | N | |
| 2.106 | " | " | " | " | " | OMe | CH | |
| 2.107 | Allyl | " | CO₂-Me | H | OMe | OMe | CH | |
| 2.108 | " | " | " | " | " | Cl | CH | |
| 2.109 | " | " | " | " | Me | Me | CH | |
| 2.110 | " | " | " | " | OMe | Me | N | |
| 2.111 | " | " | CO₂-Et | H | OMe | OMe | CH | |
| 2.112 | " | " | CO₂-n-Pr | " | " | " | CH | |
| 2.113 | " | " | CO₂-i-Pr | " | " | " | CH | |
| 2.114 | Me | CS—NH-allyl | CO₂-Me | H | OMe | OMe | CH | |

TABLE 1-continued

| No. | R¹ | R² | R³ | R⁴ | X | Y | Z | m.p. |
|---|---|---|---|---|---|---|---|---|
| 2.115 | " | " | " | " | " | OMe | N | |
| 2.116 | " | " | " | " | " | Me | N | |
| 2.117 | " | " | " | " | " | " | CH | |
| 2.118 | " | " | " | " | NMe₂ | OCH₂CF₃ | N | |
| 2.119 | " | " | " | " | Me | Me | CH | |
| 2.120 | " | " | " | " | " | " | N | |
| 2.121 | " | " | " | " | Cl | OMe | CH | |
| 2.122 | " | " | " | Me | OMe | OMe | CH | |
| 2.123 | " | " | " | " | " | Me | N | |
| 2.124 | " | " | CO₂-Et | H | OMe | OMe | CH | |
| 2.125 | " | " | " | " | " | Cl | CH | |
| 2.126 | " | " | " | " | Me | Me | CH | |
| 2.127 | " | " | " | " | OMe | Me | N | |
| 2.128 | " | " | " | " | NMe₂ | OCH₂CF₃ | N | |
| 2.129 | " | " | " | Me | OMe | OMe | CH | |
| 2.130 | " | " | " | " | OMe | Me | N | |
| 2.131 | " | " | CO₂-n-Pr | H | OMe | OMe | CH | |
| 2.132 | " | " | " | " | " | " | N | |
| 2.133 | " | " | " | " | OMe | Me | N | |
| 2.134 | " | " | " | " | Me | Me | CH | |
| 2.135 | " | " | " | " | OMe | Cl | CH | |
| 2.136 | " | " | " | Me | Me | OMe | N | |
| 2.137 | " | " | " | " | OMe | OMe | CH | |
| 2.138 | Me | CS—NH-allyl | CO₂-i-Pr | H | OMe | OMe | CH | |
| 2.139 | " | " | " | " | " | " | N | |
| 2.140 | " | " | " | " | H | Me | N | |
| 2.141 | " | " | " | " | OMe | Cl | CH | |
| 2.142 | " | " | " | " | Me | Me | CH | |
| 2.143 | " | " | " | " | SMe | NEt₂ | N | |
| 2.144 | " | " | CO₂-i-Pr | Me | OMe | Me | N | |
| 2.145 | " | " | " | " | OMe | OMe | CH | |
| 2.146 | Me | " | CO₂-Allyl | H | OMe | OMe | CH | |
| 2.147 | Et | " | CO₂-Me | H | OMe | OMe | CH | |
| 2.148 | " | " | " | H | OMe | Me | N | |
| 2.149 | " | " | " | " | Me | Me | CH | |
| 2.150 | " | " | " | " | Cl | OMe | CH | |
| 2.151 | " | " | " | Me | OMe | OMe | CH | |
| 2.152 | " | " | " | " | OMe | Me | N | |
| 2.153 | " | " | CO₂-Et | H | OMe | OMe | CH | |
| 2.154 | " | " | " | " | OMe | Me | CH | |
| 2.155 | " | " | " | " | Cl | OMe | CH | |
| 2.156 | " | " | " | " | OMe | Me | N | |
| 2.157 | " | " | " | Me | OMe | OMe | CH | |
| 2.158 | " | " | " | " | " | Me | N | |
| 2.159 | " | " | CO₂-n-Pr | H | OMe | OMe | CH | |
| 2.160 | " | " | " | " | OMe | Me | N | |
| 2.161 | " | " | " | " | OMe | Cl | CH | |
| 2.162 | " | " | " | " | Me | Me | CH | |
| 2.163 | " | " | " | Me | OMe | OMe | CH | |
| 2.164 | " | " | " | " | OMe | Me | N | |
| 2.165 | " | " | CO₂-i-Pr | H | OMe | OMe | CH | |
| 2.166 | " | " | " | " | OMe | Me | N | |
| 2.167 | " | " | " | " | Me | Me | CH | |
| 2.168 | " | " | " | Me | OMe | Me | N | |
| 2.169 | n-Pr | CS—NH-allyl | CO₂-Me | H | OMe | OMe | CH | |
| 2.170 | " | " | " | " | " | Cl | CH | |
| 2.171 | " | " | " | " | Me | Me | CH | |
| 2.172 | " | " | " | " | OMe | Me | CH | |
| 2.173 | " | " | " | Me | OMe | OMe | CH | |
| 2.174 | " | " | " | " | OMe | Me | N | |
| 2.175 | n-Pr | " | CO₂-Et | H | " | " | N | |
| 2.176 | " | " | " | " | " | OMe | CH | |
| 2.177 | " | " | " | " | Me | Me | CH | |
| 2.178 | " | " | CO₂-n-Pr | " | OMe | OMe | CH | |
| 2.179 | i-Pr | " | CO₂-Me | H | OMe | OMe | CH | |
| 2.180 | " | " | " | " | OMe | Me | N | |
| 2.181 | " | " | " | " | Me | Me | CH | |
| 2.182 | " | " | " | " | Cl | OMe | N | |

TABLE 1-continued

| No. | R¹ | R² | R³ | R⁴ | X | Y | Z | m.p. |
|---|---|---|---|---|---|---|---|---|
| 2.183 | " | " | " | Me | OMe | Me | N | |
| 2.184 | " | " | " | " | " | OMe | CH | |
| 2.185 | Allyl | " | CO₂-Me | H | OMe | OMe | CH | |
| 2.186 | " | " | " | " | " | Cl | CH | |
| 2.187 | " | " | " | " | Me | Me | CH | |
| 2.188 | " | " | " | " | OMe | Me | N | |
| 2.189 | " | " | CO₂-Et | OMe | OMe | OMe | CH | |
| 2.190 | " | " | CO₂-n-Pr | " | " | " | CH | |
| 2.191 | " | " | CO₂-i-Pr | " | " | " | CH | |
| 2.192 | Me | CS—NH—CO₂Et | CO₂-Me | H | OMe | OMe | CH | 144–145° C. |
| 2.193 | " | " | " | " | " | OMe | N | |
| 2.194 | " | " | " | " | " | Me | N | |
| 2.195 | " | " | " | " | " | " | CH | |
| 2.196 | " | " | " | " | NMe₂ | OCH₂CF₃ | N | |
| 2.197 | " | " | " | " | Me | Me | CH | |
| 2.198 | " | " | " | " | " | " | N | |
| 2.199 | " | " | " | " | Cl | OMe | CH | |
| 2.200 | " | " | " | Me | OMe | OMe | CH | |
| 2.201 | " | " | " | " | " | Me | N | |
| 2.202 | " | " | CO₂-Et | H | OMe | OMe | CH | |
| 2.203 | " | " | " | " | " | Cl | CH | |
| 2.204 | " | " | " | " | Me | Me | CH | |
| 2.205 | " | " | " | " | OMe | Me | N | |
| 2.206 | " | " | " | " | NMe₂ | OCH₂CF₃ | N | |
| 2.207 | " | " | " | M | OMe | OMe | CH | |
| 2.208 | " | " | " | " | OMe | Me | N | |
| 2.209 | " | " | CO₂-n-Pr | H | OMe | OMe | CH | |
| 2.210 | " | " | " | " | " | " | N | |
| 2.211 | " | " | " | " | OMe | OMe | N | |
| 2.212 | " | " | " | " | Me | Me | CH | |
| 2.213 | " | " | " | " | OMe | Cl | CH | |
| 2.214 | " | " | " | Me | Me | OMe | N | |
| 2.215 | " | " | " | " | OMe | OMe | CH | |
| 2.216 | Me | CS—NH—CO₂Et | CO₂-i-Pr | N | OMe | OMe | CH | |
| 2.217 | " | " | " | " | " | " | N | |
| 2.218 | " | " | " | " | OMe | Me | N | |
| 2.219 | " | " | " | " | OMe | Cl | CH | |
| 2.220 | " | " | " | " | Me | Me | CH | |
| 2.221 | " | " | " | " | SMe | NEt₂ | N | |
| 2.222 | " | " | CO₂-i-Pr | Me | OMe | Me | N | |
| 2.223 | " | " | " | " | OMe | OMe | CH | |
| 2.224 | Me | " | CO₂-Allyl | H | OMe | OMe | CH | |
| 2.225 | Et | " | CO₂-Me | H | OMe | OMe | CH | |
| 2.226 | " | " | " | H | OMe | Me | N | |
| 2.227 | " | " | " | " | Me | Me | CH | |
| 2.228 | " | " | " | " | Cl | OMe | CH | |
| 2.229 | " | " | " | Me | OMe | OMe | CH | |
| 2.230 | " | " | " | " | OMe | Me | N | |
| 2.231 | " | " | CO₂-Et | H | OMe | OMe | CH | |
| 2.232 | " | " | " | " | OMe | Me | CH | |
| 2.233 | " | " | " | " | Cl | OMe | CH | |
| 2.234 | " | " | " | " | OMe | Me | N | |
| 2.235 | " | " | " | Me | OMe | OMe | CH | |
| 2.236 | " | " | " | " | " | Me | N | |
| 2.237 | " | " | CO₂-n-Pr | H | OMe | OMe | CH | |
| 2.238 | " | " | " | " | OMe | Me | N | |
| 2.239 | " | " | " | " | OMe | Cl | CH | |
| 2.240 | " | " | " | " | Me | Me | CH | |
| 2.241 | " | " | " | Me | OMe | OMe | CH | |
| 2.242 | " | " | " | " | OMe | Me | N | |
| 2.243 | " | " | CO₂-i-Pr | H | OMe | OMe | CH | |
| 2.244 | " | " | " | " | OMe | Me | N | |
| 2.245 | " | " | " | " | Me | Me | CH | |
| 2.246 | " | " | " | Me | OMe | Me | N | |
| 2.247 | n-Pr | CS—NH—CO₂Et | CO₂-Me | H | OMe | OMe | CH | |
| 2.248 | " | " | " | " | " | Cl | CH | |
| 2.249 | " | " | " | " | Me | Me | CH | |
| 2.250 | " | " | " | " | OMe | Me | N | |

TABLE 1-continued

| No. | R¹ | R² | R³ | R⁴ | X | Y | Z | m.p. |
|---|---|---|---|---|---|---|---|---|
| 2.251 | " | " | " | Me | OMe | OMe | CH | |
| 2.252 | " | " | " | " | OMe | Me | N | |
| 2.253 | n-Pr | " | CO₂-Et | H | " | " | N | |
| 2.254 | " | " | " | " | " | OMe | CH | |
| 2.255 | " | " | " | " | Me | Me | CH | |
| 2.256 | " | " | CO₂-n-Pr | " | OMe | OMe | CH | |
| 2.257 | i-Pr | " | CO₂-Me | H | OMe | OMe | CH | |
| 2.258 | " | " | " | " | OMe | Me | N | |
| 2.259 | " | " | " | " | Me | Me | CH | |
| 2.260 | " | " | " | " | Cl | OMe | N | |
| 2.261 | " | " | " | Me | OMe | Me | N | |
| 2.262 | " | " | " | " | " | OMe | CH | |
| 2.263 | Allyl | " | CO₂-Me | H | OMe | OMe | CH | |
| 2.264 | " | " | " | " | " | Cl | CH | |
| 2.265 | " | " | " | " | Me | Me | CH | |
| 2.266 | " | " | " | " | OMe | Me | N | |
| 2.267 | " | " | CO₂-Et | H | OMe | OMe | CH | |
| 2.268 | " | " | CO₂-n-Pr | H | OMe | OMe | CH | |
| 2.269 | " | " | CO₂-i-Pr | " | " | " | CH | |
| 2.270 | Me | SO₂NHMe | CO₂-Me | H | OMe | OMe | CH | 117–118° C. |
| 2.271 | " | " | " | " | " | OMe | N | |
| 2.272 | " | " | " | " | " | Me | N | |
| 2.273 | " | " | " | " | " | " | CH | |
| 2.274 | " | " | " | " | NMe₂ | OCH₂CF₃ | N | |
| 2.275 | " | " | " | " | Me | Me | CH | |
| 2.276 | " | " | " | " | " | " | N | |
| 2.277 | " | " | " | " | Cl | OMe | CH | |
| 2.278 | " | " | " | Me | OMe | OMe | CH | |
| 2.279 | " | " | " | " | " | Me | N | |
| 2.280 | " | " | CO₂-Et | H | OMe | OMe | CH | |
| 2.281 | " | " | " | " | " | Cl | CH | |
| 2.282 | " | " | " | " | Me | Me | CH | |
| 2.283 | " | " | " | " | OMe | Me | N | |
| 2.284 | " | " | " | " | NMe₂ | OCH₂CF₃ | N | |
| 2.285 | " | " | " | Me | OMe | OMe | CH | |
| 2.286 | " | " | " | " | OMe | Me | N | |
| 2.287 | " | " | CO₂-n-Pr | H | OMe | OMe | CH | |
| 2.288 | " | " | " | " | " | " | N | |
| 2.289 | " | " | " | " | OMe | Me | N | |
| 2.290 | " | " | " | " | Me | Me | CH | |
| 2.291 | " | " | " | " | OMe | Cl | CH | |
| 2.292 | " | " | " | Me | Me | OMe | N | |
| 2.293 | " | " | " | " | OMe | OMe | CH | |
| 2.294 | Me | SO₂—NHMe | CO₂-i-Pr | H | OMe | OMe | CH | |
| 2.295 | " | " | " | " | " | " | N | |
| 2.296 | " | " | " | " | OMe | Me | N | |
| 2.297 | " | " | " | " | Me | Me | CH | |
| 2.298 | " | " | " | " | Me | Me | CH | |
| 2.299 | " | " | " | " | SMe | NEt₂ | N | |
| 2.300 | " | " | CO₂-i-Pr | Me | OMe | Me | N | |
| 2.301 | " | " | " | " | OMe | OMe | CH | |
| 2.302 | Me | " | CO₂-Allyl | H | OMe | OMe | CH | |
| 2.303 | Et | " | CO₂-Me | H | OMe | OMe | CH | |
| 2.304 | " | " | " | H | OMe | Me | N | |
| 2.305 | " | " | " | " | Me | Me | CH | |
| 2.306 | " | " | " | " | Cl | OMe | CH | |
| 2.307 | " | " | " | Me | OMe | OMe | CH | |
| 2.308 | " | " | " | " | OMe | Me | N | |
| 2.309 | " | " | CO₂-Et | H | OMe | OMe | CH | |
| 2.310 | " | " | " | " | OMe | Me | CH | |
| 2.311 | " | " | " | " | Cl | OMe | CH | |
| 2.312 | " | " | " | " | OMe | Me | N | |
| 2.313 | " | " | " | Me | OMe | OMe | CH | |
| 2.314 | " | " | " | " | " | Me | N | |
| 2.315 | " | " | CO₂-n-Pr | H | OMe | OMe | CH | |
| 2.316 | " | " | " | " | OMe | Me | N | |
| 2.317 | " | " | " | " | OMe | Cl | CH | |
| 2.318 | " | " | " | " | Me | Me | CH | |

TABLE 1-continued

Structure: R¹R²N-phenyl(R³)-SO₂NH-CO-NR⁴-[pyrimidine/triazine with X, Y, Z]

| No. | R¹ | R² | R³ | R⁴ | X | Y | Z | m.p. |
|---|---|---|---|---|---|---|---|---|
| 2.319 | " | " | " | Me | OMe | OMe | CH | |
| 2.320 | " | " | " | " | OMe | Me | N | |
| 2.321 | " | " | CO-i-Pr | H | OMe | OMe | CH | |
| 2.322 | " | " | " | " | OMe | Me | N | |
| 2.323 | " | " | " | " | Me | Me | CH | |
| 2.324 | " | " | " | Me | OMe | Me | N | |
| 2.325 | n-Pr | SO₂NHMe | CO₂-Me | H | OMe | OMe | CH | |
| 2.326 | " | " | " | " | " | Cl | CH | |
| 2.327 | " | " | " | " | Me | Me | CH | |
| 2.328 | " | " | " | " | OMe | Me | N | |
| 2.329 | " | " | " | Me | OMe | OMe | CH | |
| 2.330 | " | " | " | " | OMe | Me | N | |
| 2.331 | n-Pr | " | CO₂-Et | H | " | " | N | |
| 2.332 | " | " | " | " | " | OMe | CH | |
| 2.333 | " | " | " | " | Me | Me | CH | |
| 2.334 | " | " | CO₂-n-Pr | " | OMe | OMe | CH | |
| 2.335 | i-Pr | " | CO₂-Me | H | OMe | OMe | CH | |
| 2.336 | " | " | " | " | OMe | Me | N | |
| 2.337 | " | " | " | " | Me | Me | CH | |
| 2.338 | " | " | " | " | Cl | OMe | N | |
| 2.339 | " | " | " | Me | OMe | Me | N | |
| 2.340 | " | " | " | " | " | OMe | CH | |
| 2.341 | Allyl | " | CO₂-Me | H | OMe | OMe | CH | |
| 2.342 | " | " | " | " | " | Cl | CH | |
| 2.343 | " | " | " | " | Me | Me | CH | |
| 2.344 | " | " | " | " | OMe | Me | N | |
| 2.345 | " | " | CO₂-Et | H | OMe | OMe | CH | |
| 2.346 | " | " | CO₂-n-Pr | H | OMe | OMe | CH | |
| 2.347 | " | " | CO₂-i-Pr | " | " | " | CH | |
| 2.348 | Me | SO₂NMe₂ | CO₂-Me | H | OMe | OMe | CH | |
| 2.349 | " | " | " | " | " | OMe | N | |
| 2.350 | " | " | " | " | " | Me | N | |
| 2.351 | " | " | " | " | " | " | CH | |
| 2.352 | " | " | " | " | NMe₂ | OCH₂CF₃ | N | |
| 2.353 | " | " | " | " | Me | Me | CH | |
| 2.354 | " | " | " | " | " | " | N | |
| 2.355 | " | " | " | " | Cl | OMe | CH | |
| 2.356 | " | " | " | Me | OMe | OMe | CH | |
| 2.357 | " | " | " | " | " | Me | N | |
| 2.358 | " | " | CO₂-Et | H | OMe | OMe | CH | |
| 2.359 | " | " | " | " | " | Cl | CH | |
| 2.360 | " | " | " | " | Me | Me | CH | |
| 2.361 | " | " | " | " | OMe | Me | N | |
| 2.362 | " | " | " | " | NMe₂ | OCH₂CF₃ | N | |
| 2.363 | " | " | " | Me | OMe | OMe | CH | |
| 2.364 | " | " | " | " | OMe | Me | N | |
| 2.365 | " | " | CO₂-n-Pr | H | OMe | OMe | CH | |
| 2.366 | " | " | " | " | " | " | N | |
| 2.367 | " | " | " | " | OMe | Me | N | |
| 2.368 | " | " | " | " | Me | Me | CH | |
| 2.369 | " | " | " | " | OMe | Cl | CH | |
| 2.370 | " | " | " | Me | Me | OMe | N | |
| 2.371 | " | " | " | " | OMe | OMe | CH | |
| 2.372 | Me | SO₂NMe₂ | CO₂-i-Pr | H | OMe | OMe | CH | |
| 2.373 | " | " | " | " | " | " | N | |
| 2.374 | " | " | " | " | OMe | Me | N | |
| 2.375 | " | " | " | " | OMe | Cl | CH | |
| 2.376 | " | " | " | " | Me | Me | CH | |
| 2.377 | " | " | " | " | SMe | NEt₂ | N | |
| 2.378 | " | " | CO₂-i-Pr | Me | OMe | Me | N | |
| 2.379 | " | " | " | " | OMe | OMe | CH | |
| 2.380 | Me | " | CO₂-Allyl | H | OMe | OMe | CH | |
| 2.381 | Et | " | CO₂-Me | H | OMe | OMe | CH | |
| 2.382 | " | " | " | H | OMe | Me | N | |
| 2.383 | " | " | " | " | Me | Me | CH | |
| 2.384 | " | " | " | " | Cl | OMe | CH | |
| 2.385 | " | " | " | Me | OMe | OMe | CH | |
| 2.386 | " | " | " | " | OMe | Me | N | |

TABLE 1-continued

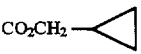

| No. | R¹ | R² | R³ | R⁴ | X | Y | Z | m.p. |
|---|---|---|---|---|---|---|---|---|
| 2.387 | " | " | CO₂-Et | H | OMe | OMe | CH | |
| 2.388 | " | " | " | " | OMe | Me | CH | |
| 2.389 | " | " | " | " | Cl | OMe | CH | |
| 2.390 | " | " | " | " | OMe | Me | N | |
| 2.391 | " | " | " | Me | OMe | OMe | CH | |
| 2.392 | " | " | " | " | " | Me | N | |
| 2.393 | " | " | CO₂-n-Pr | H | OMe | OMe | CH | |
| 2.394 | " | " | " | " | OMe | Me | N | |
| 2.395 | " | " | " | " | OMe | Cl | CH | |
| 2.396 | " | " | " | " | Me | Me | CH | |
| 2.397 | " | " | " | Me | OMe | OMe | CH | |
| 2.398 | " | " | " | " | OMe | Me | N | |
| 2.399 | " | " | CO₂-i-Pr | H | OMe | OMe | CH | |
| 2.400 | " | " | " | " | OMe | Me | N | |
| 2.401 | " | " | " | " | Me | Me | CH | |
| 2.402 | " | " | " | Me | OMe | Me | N | |
| 2.403 | n-Pr | SO₂NMe₂ | CO₂-Me | H | OMe | OMe | CH | |
| 2.404 | " | " | " | " | " | Cl | CH | |
| 2.405 | " | " | " | " | Me | Me | CH | |
| 2.406 | " | " | " | " | OMe | Me | N | |
| 2.407 | " | " | " | Me | OMe | OMe | CH | |
| 2.408 | " | " | " | " | OMe | Me | N | |
| 2.409 | n-Pr | " | CO₂-Et | H | OMe | Me | N | |
| 2.410 | " | " | " | " | " | OMe | CH | |
| 2.411 | " | " | " | " | Me | Me | CH | |
| 2.412 | " | " | CO₂-n-Pr | " | OMe | OMe | CH | |
| 2.413 | i-Pr | " | CO₂-Me | H | OMe | OMe | CH | |
| 2.414 | " | " | " | " | OMe | Me | N | |
| 2.415 | " | " | " | " | Me | Me | CH | |
| 2.416 | " | " | " | " | Cl | OMe | N | |
| 2.417 | " | " | " | Me | OMe | Me | N | |
| 2.418 | " | " | " | " | " | OMe | CH | |
| 2.419 | Allyl | " | CO₂-Me | H | OMe | OMe | CH | |
| 2.420 | " | " | " | " | " | Cl | CH | |
| 2.421 | " | " | " | " | Me | Me | CH | |
| 2.422 | " | " | " | " | OMe | Me | N | |
| 2.423 | " | " | CO₂-Et | H | OMe | OMe | CH | |
| 2.424 | " | " | CO₂-n-Pr | H | OMe | OMe | CH | |
| 2.425 | " | " | CO₂-i-Pr | " | " | " | CH | |
| 2.426 | Me | CHO | CO₂CH₂— | H | OMe | OMe | CH | |
| 2.427 | " | " | " | H | OMe | Me | N | |
| 2.428 | " | " | " | " | Me | Me | CH | |
| 2.429 | " | CO—CH₃ | " | " | OMe | OMe | CH | |
| 2.430 | " | " | " | " | OMe | Me | N | |
| 2.431 | " | " | " | " | Me | Me | CH | |
| 2.432 | " | COCH₂CH₃ | " | " | OMe | OMe | CH | |
| 2.433 | Et | CHO | " | " | " | " | CH | |
| 2.434 | Pr | " | " | " | " | " | CH | |
| 2.435 | Et | COCH₃ | " | " | " | " | CH | |
| 2.436 | Pr | " | " | " | " | " | CH | |
| 2.437 | Et | COCH₂CH₃ | " | " | " | " | CH | |
| 2.438 | Me | CO—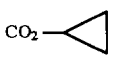 | " | " | " | " | CH | |
| 2.439 | Me | CO₂Me | " | " | " | " | CH | |
| 2.440 | Et | " | " | " | " | " | CH | |
| 2.441 | Pr | " | " | " | " | " | CH | |
| 2.442 | Me | CO—NHEt | " | " | " | " | CH | |
| 2.443 | Et | " | " | " | " | " | CH | |
| 2.444 | Pr | " | " | " | " | " | CH | |
| 2.445 | Me | CHO | CO₂—△ | H | OMe | OMe | CH | |

TABLE 1-continued

| No. | R¹ | R² | R³ | R⁴ | X | Y | Z | m.p. |
|---|---|---|---|---|---|---|---|---|
| 2.446 | " | " | " | H | OMe | Me | N | |
| 2.447 | " | " | " | " | Me | Me | CH | |
| 2.448 | " | CO—CH₃ | " | " | OMe | OMe | CH | |
| 2.449 | " | " | " | " | OMe | Me | N | |
| 2.450 | " | " | " | " | Me | Me | CH | |
| 2.451 | " | COCH₂CH₃ | " | " | OMe | OMe | CH | |
| 2.452 | Et | CHO | " | " | " | " | CH | |
| 2.453 | Pr | " | " | " | " | " | CH | |
| 2.454 | Et | COCH₃ | " | " | " | " | CH | |
| 2.455 | Pr | " | " | " | " | " | CH | |
| 2.456 | Et | COCH₂CH₃ | " | " | " | " | CH | |
| 2.457 | Me | CO—△ | " | " | " | " | CH | |
| 2.458 | Me | CO₂Me | " | " | " | " | CH | |
| 2.459 | Et | " | " | " | " | " | CH | |
| 2.460 | Pr | " | " | " | " | " | CH | |
| 2.461 | Me | CO—NHEt | " | " | " | " | CH | |
| 2.462 | Et | " | " | " | " | " | CH | |
| 2.463 | Pr | " | " | " | " | " | CH | |
| 2.464 | Me | CHO | CO₂—N=CHMe₂ | H | OMe | OMe | CH | |
| 2.465 | " | " | " | H | OMe | Me | N | |
| 2.466 | " | " | " | " | Me | Me | CH | |
| 2.467 | " | CO—CH₃ | " | " | OMe | OMe | CH | |
| 2.468 | " | " | " | " | OMe | Me | N | |
| 2.469 | " | " | " | " | Me | Me | CH | |
| 2.470 | " | COCH₂CH₃ | " | " | OMe | OMe | CH | |
| 2.471 | Et | CHO | " | " | " | " | CH | |
| 2.472 | Pr | " | " | " | " | " | CH | |
| 2.473 | Et | COCH₃ | " | " | " | " | CH | |
| 2.474 | Pr | " | " | " | " | " | CH | |
| 2.475 | Et | COCH₂CH₃ | " | " | " | " | CH | |
| 2.476 | Me | CO—△ | " | " | " | " | CH | |
| 2.477 | Me | CO₂Me | " | " | " | " | CH | |
| 2.478 | Et | " | " | " | " | " | CH | |
| 2.479 | Pr | " | " | " | " | " | CH | |
| 2.480 | Me | CO—NHEt | " | " | " | " | CH | |
| 2.481 | Et | " | " | " | " | " | CH | |
| 2.482 | Pr | " | " | " | " | " | CH | |
| 2.483 | Me | CHO | CO₂CH₂CH₂Cl | H | OMe | OMe | CH | |
| 2.484 | " | " | " | " | OMe | Me | N | |
| 2.485 | " | " | " | " | Me | Me | CH | |
| 2.486 | " | CO—CH₃ | " | " | OMe | OMe | CH | |
| 2.487 | " | " | " | " | OMe | Me | N | |
| 2.488 | " | " | " | " | Me | Me | CH | |
| 2.489 | " | COCH₂CH₃ | " | " | OMe | OMe | CH | |
| 2.490 | Et | CHO | " | " | " | " | " | |
| 2.491 | Pr | " | " | " | " | " | " | |
| 2.492 | Et | COCH₃ | " | " | " | " | " | |
| 2.493 | Pr | " | " | " | " | " | " | |
| 2.494 | Et | COCH₂CH₃ | " | " | " | " | " | |
| 2.495 | Me | CO—△ | " | " | " | " | " | |
| 2.496 | Me | CO₂Me | " | " | " | " | " | |
| 2.497 | Et | " | " | " | " | " | " | |
| 2.498 | Pr | " | " | " | " | " | " | |
| 2.499 | Me | CO—NHEt | " | " | " | " | " | |
| 2.500 | Et | " | " | " | " | " | " | |
| 2.501 | Pr | " | " | " | " | " | " | |
| 2.502 | Me | CHO | CO₂(CH₂)₂OMe | H | OMe | OMe | CH | |

TABLE 1-continued

Structure: R¹R²N-phenyl(R³)-SO₂NH-CO-NR⁴-[triazine/pyrimidine ring with X, Y, Z]

| No. | R¹ | R² | R³ | R⁴ | X | Y | Z | m.p. |
|---|---|---|---|---|---|---|---|---|
| 2.503 | " | " | " | H | OMe | Me | N | |
| 2.504 | " | " | " | " | Me | Me | CH | |
| 2.505 | " | CO—CH₃ | " | " | OMe | OMe | CH | |
| 2.506 | " | " | " | " | OMe | Me | N | |
| 2.507 | " | " | " | " | Me | Me | CH | |
| 2.508 | " | COCH₂CH₃ | " | " | OMe | OMe | CH | |
| 2.509 | Et | CHO | " | " | " | " | " | |
| 2.510 | Pr | " | " | " | " | " | " | |
| 2.511 | Et | COCH₃ | " | " | " | " | " | |
| 2.512 | Pr | " | " | " | " | " | " | |
| 2.513 | Et | COCH₂CH₃ | " | " | " | " | " | |
| 2.514 | Me | CO—◁ | " | " | " | " | " | |
| 2.515 | Me | CO₂Me | " | " | " | " | " | |
| 2.516 | Et | " | " | " | " | " | " | |
| 2.517 | Pr | " | " | " | " | " | " | |
| 2.518 | Me | CO—NHEt | " | " | " | " | " | |
| 2.519 | Et | " | " | " | " | " | " | |
| 2.520 | Pr | " | " | " | " | " | " | |
| 2.521 | Me | CHO | CO₂CH₂CCl₃ | H | OMe | OMe | CH | |
| 2.522 | " | " | " | H | OMe | Me | N | |
| 2.523 | " | " | " | " | Me | Me | CH | |
| 2.524 | " | CO—CH₃ | " | " | OMe | OMe | CH | |
| 2.525 | " | " | " | " | OMe | Me | N | |
| 2.526 | " | " | " | " | Me | Me | CH | |
| 2.527 | " | COCH₂CH₃ | " | " | OMe | OMe | CH | |
| 2.528 | Et | CHO | " | " | " | " | " | |
| 2.529 | Pr | " | " | " | " | " | " | |
| 2.530 | Et | COCH₃ | " | " | " | " | " | |
| 2.531 | Pr | " | " | " | " | " | " | |
| 2.532 | Et | COCH₂CH₃ | " | " | " | " | " | |
| 2.533 | Me | CO—◁ | " | " | " | " | " | |
| 2.534 | Me | CO₂Me | " | " | " | " | " | |
| 2.535 | Et | " | " | " | " | " | " | |
| 2.536 | Pr | " | " | " | " | " | " | |
| 2.537 | Me | CO—NHEt | " | " | " | " | " | |
| 2.538 | Et | " | " | " | " | " | " | |
| 2.539 | Pr | " | " | " | " | " | " | |
| 2.540 | Me | CHO | CO₂CH₂C≡CH | H | OMe | OMe | CH | |
| 2.541 | " | " | " | H | OMe | Me | N | |
| 2.542 | " | " | " | " | Me | Me | CH | |
| 2.543 | " | CO—CH₃ | " | " | OMe | OMe | CH | |
| 2.544 | " | " | " | " | OMe | Me | N | |
| 2.545 | " | " | " | " | Me | Me | CH | |
| 2.546 | " | COCH₂CH₃ | " | " | OMe | OMe | CH | |
| 2.547 | Et | CHO | " | " | " | " | " | |
| 2.548 | Pr | " | " | " | " | " | " | |
| 2.549 | Et | COCH₃ | " | " | " | " | " | |
| 2.550 | Pr | " | " | " | " | " | " | |
| 2.551 | Et | COCH₂CH₃ | " | " | " | " | " | |
| 2.552 | Me | CO—◁ | " | " | " | " | " | |
| 2.553 | Me | CO₂Me | " | " | " | " | " | |
| 2.554 | Et | " | " | " | " | " | " | |
| 2.555 | Pr | " | " | " | " | " | " | |
| 2.556 | Me | CO—NHEt | " | " | " | " | " | |
| 2.557 | Et | " | " | " | " | " | " | |
| 2.558 | Pr | " | " | " | " | " | " | |
| 2.559 | Me | SO₂Et | CO₂Me | H | OMe | OMe | CH | |

TABLE 1-continued

| No. | R¹ | R² | R³ | R⁴ | X | Y | Z | m.p. |
|---|---|---|---|---|---|---|---|---|
| 2.560 | " | " | " | " | " | OMe | N | |
| 2.561 | " | " | " | " | " | Me | N | |
| 2.562 | " | " | " | " | " | " | CH | |
| 2.563 | " | " | " | " | NMe₂ | OCH₂CF₃ | N | |
| 2.564 | " | " | " | " | Me | Me | CH | |
| 2.565 | " | " | " | " | " | " | N | |
| 2.566 | " | " | " | " | Cl | OMe | CH | |
| 2.567 | " | " | " | Me | OMe | OMe | CH | |
| 2.568 | " | " | " | " | " | Me | N | |
| 2.569 | " | " | CO₂Et | H | OMe | OMe | CH | |
| 2.570 | " | " | " | " | " | Cl | CH | |
| 2.571 | " | " | " | " | Me | Me | CH | |
| 2.572 | " | " | " | " | OMe | Me | N | |
| 2.573 | " | " | " | " | NMe₂ | OCH₂CF₃ | N | |
| 2.574 | " | " | " | Me | OMe | OMe | CH | |
| 2.575 | " | " | " | " | OMe | Me | N | |
| 2.576 | " | " | CO₂-n-Pr | H | OMe | OMe | CH | |
| 2.577 | " | " | " | " | " | " | N | |
| 2.578 | " | " | " | " | OMe | Me | N | |
| 2.579 | " | " | " | " | Me | Me | CH | |
| 2.580 | " | " | " | " | OMe | Cl | CH | |
| 2.581 | " | " | " | Me | Me | OMe | N | |
| 2.582 | " | " | " | " | OMe | OMe | CH | |
| 2.583 | Me | SO₂Et | CO₂-i-Pr | H | OMe | OMe | CH | |
| 2.584 | " | " | " | " | " | " | N | |
| 2.585 | " | " | " | " | OMe | Me | N | |
| 2.586 | " | " | " | " | OMe | Cl | CH | |
| 2.587 | " | " | " | " | Me | Me | CH | |
| 2.588 | " | " | " | " | SMe | NEt₂ | N | |
| 2.589 | " | " | CO₂-i-Pr | Me | OMe | Me | N | |
| 2.590 | " | " | " | " | OMe | OMe | CH | |
| 2.591 | Me | " | CO₂-allyl | H | OMe | OMe | CH | |
| 2.592 | Et | " | CO₂Me | H | OMe | OMe | CH | |
| 2.593 | " | " | " | H | OMe | Me | N | |
| 2.594 | " | " | " | " | Me | Me | CH | |
| 2.595 | " | " | " | " | Cl | OMe | CH | |
| 2.596 | " | " | " | Me | OMe | OMe | CH | |
| 2.597 | " | " | " | " | OMe | Me | N | |
| 2.598 | " | " | CO₂Et | H | OMe | OMe | CH | |
| 2.599 | " | " | " | " | OMe | Me | CH | |
| 2.600 | " | " | " | " | Cl | OMe | CH | |
| 2.601 | " | " | " | " | OMe | Me | N | |
| 2.602 | " | " | " | Me | OMe | OMe | CH | |
| 2.603 | " | " | " | " | " | Me | N | |
| 2.604 | " | " | CO₂-n-Pr | H | OMe | OMe | CH | |
| 2.605 | " | " | " | " | OMe | Me | N | |
| 2.606 | " | " | " | " | OMe | Cl | CH | |
| 2.607 | " | " | " | " | Me | Me | CH | |
| 2.608 | " | " | " | Me | OMe | OMe | CH | |
| 2.609 | " | " | " | " | OMe | Me | N | |
| 2.610 | " | " | CO₂-i-Pr | H | OMe | OMe | CH | |
| 2.611 | " | " | " | " | OMe | Me | N | |
| 2.612 | " | " | " | " | Me | Me | CH | |
| 2.613 | " | " | " | Me | OMe | Me | N | |
| 2.614 | n-Pr | SO₂Et | CO₂Me | H | OMe | OMe | CH | |
| 2.615 | " | " | " | " | " | Cl | CH | |
| 2.616 | " | " | " | " | Me | Me | CH | |
| 2.617 | " | " | " | " | OMe | Me | N | |
| 2.618 | " | " | " | Me | OMe | OMe | CH | |
| 2.619 | " | " | " | " | OMe | Me | N | |
| 2.620 | n-Pr | " | CO₂Et | H | " | " | N | |
| 2.621 | " | " | " | " | " | OMe | CH | |
| 2.622 | " | " | " | " | Me | Me | CH | |
| 2.623 | " | " | CO₂-n-Pr | " | OMe | OMe | CH | |
| 2.624 | i-Pr | " | CO₂Me | H | " | " | CH | |
| 2.625 | " | " | " | " | " | Me | N | |
| 2.626 | " | " | " | " | Me | Me | CH | |
| 2.627 | " | " | " | " | Cl | OMe | N | |

TABLE 1-continued

| No. | R¹ | R² | R³ | R⁴ | X | Y | Z | m.p. |
|---|---|---|---|---|---|---|---|---|
| 2.628 | " | " | " | Me | OMe | Me | N | |
| 2.629 | " | " | " | " | " | OMe | CH | |
| 2.630 | Allyl | " | CO₂Me | H | OMe | OMe | CH | |
| 2.631 | " | " | " | " | " | Cl | CH | |
| 2.632 | " | " | " | " | Me | Me | CH | |
| 2.633 | " | " | " | " | OMe | Me | N | |
| 2.634 | " | " | CO₂-Et | H | OMe | OMe | CH | |
| 2.635 | " | " | CO₂-n-Pr | H | OMe | OMe | CH | |
| 2.636 | " | " | CO₂-i-Pr | " | " | " | CH | |
| 2.637 | Me | SO₂CH₂Cl | CO₂-Me | H | OMe | OMe | CH | |
| 2.638 | " | " | " | " | " | OMe | N | |
| 2.639 | " | " | " | " | " | Me | N | |
| 2.640 | " | " | " | " | " | " | CH | |
| 2.641 | " | " | " | " | NMe₂ | OCH₂CF₃ | N | |
| 2.642 | " | " | " | " | Me | Me | CH | |
| 2.643 | " | " | " | " | " | " | N | |
| 2.644 | " | " | " | " | Cl | OMe | CH | |
| 2.645 | " | " | " | Me | OMe | OMe | CH | |
| 2.646 | " | " | " | " | " | Me | N | |
| 2.647 | " | " | CO₂-Et | H | OMe | OMe | CH | |
| 2.648 | " | " | " | " | " | Cl | CH | |
| 2.649 | " | " | " | " | Me | Me | CH | |
| 2.650 | " | " | " | " | OMe | Me | N | |
| 2.651 | " | " | " | " | NMe₂ | OCH₂CF₃ | N | |
| 2.652 | " | " | " | Me | OMe | OMe | CH | |
| 2.653 | " | " | " | " | OMe | Me | N | |
| 2.654 | " | " | CO₂-n-Pr | H | OMe | OMe | CH | |
| 2.655 | " | " | " | " | " | " | N | |
| 2.656 | " | " | " | " | OMe | Me | N | |
| 2.657 | " | " | " | " | Me | Me | CH | |
| 2.658 | " | " | " | " | OMe | Cl | CH | |
| 2.659 | " | " | " | Me | Me | OMe | N | |
| 2.660 | " | " | " | " | OMe | OMe | CH | |
| 2.661 | Me | SO₂CH₂Cl | CO₂-i-Pr | H | OMe | OMe | CH | |
| 2.662 | " | " | " | " | " | " | N | |
| 2.663 | " | " | " | " | OMe | Me | N | |
| 2.664 | " | " | " | " | OMe | Cl | CH | |
| 2.665 | " | " | " | " | Me | Me | CH | |
| 2.666 | " | " | " | " | SMe | NEt₂ | N | |
| 2.667 | " | " | CO₂-i-Pr | Me | OMe | Me | N | |
| 2.668 | " | " | " | " | OMe | OMe | CH | |
| 2.669 | Me | " | CO₂-Allyl | H | OMe | OMe | CH | |
| 2.670 | Et | " | CO₂-Me | H | OMe | OMe | CH | |
| 2.671 | " | " | " | H | OMe | Me | N | |
| 2.672 | " | " | " | " | Me | Me | CH | |
| 2.673 | " | " | " | " | Cl | OMe | CH | |
| 2.674 | " | " | " | Me | OMe | OMe | CH | |
| 2.675 | " | " | " | " | OMe | Me | N | |
| 2.676 | " | " | CO₂-Et | H | OMe | OMe | CH | |
| 2.677 | " | " | " | " | OMe | Me | CH | |
| 2.678 | " | " | " | " | Cl | OMe | CH | |
| 2.679 | " | " | " | " | OMe | Me | N | |
| 2.680 | " | " | " | Me | OMe | OMe | CH | |
| 2.681 | " | " | " | " | " | Me | N | |
| 2.682 | " | " | CO₂-n-Pr | H | OMe | OMe | CH | |
| 2.683 | " | " | " | " | OMe | Me | N | |
| 2.684 | " | " | " | " | OMe | Cl | CH | |
| 2.685 | " | " | " | " | Me | Me | CH | |
| 2.686 | " | " | " | Me | OMe | OMe | CH | |
| 2.687 | " | " | " | " | " | Me | N | |
| 2.688 | " | " | CO₂i-Pr | H | OMe | OMe | CH | |
| 2.689 | " | " | " | " | OMe | Me | N | |
| 2.690 | " | " | " | " | Me | Me | CH | |
| 2.691 | " | " | " | Me | OMe | Me | N | |
| 2.692 | n-Pr | SO₂CH₂Cl | CO₂-Me | H | OMe | OMe | CH | |
| 2.693 | " | " | " | " | " | Cl | CH | |
| 2.694 | " | " | " | " | Me | Me | CH | |
| 2.695 | " | " | " | " | OMe | Me | N | |

TABLE 1-continued

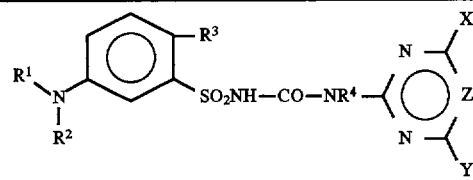

| No. | R¹ | R² | R³ | R⁴ | X | Y | Z | m.p. |
|---|---|---|---|---|---|---|---|---|
| 2.696 | " | " | " | Me | OMe | OMe | CH | |
| 2.697 | " | " | " | " | " | Me | N | |
| 2.698 | n-Pr | " | CO₂-Et | H | " | " | N | |
| 2.699 | " | " | " | " | " | OMe | CH | |
| 2.700 | " | " | " | " | Me | Me | CH | |
| 2.701 | " | " | CO₂-n-Pr | " | OMe | OMe | CH | |
| 2.702 | i-Pr | " | CO₂-Me | H | " | OMe | CH | |
| 2.703 | " | " | " | " | " | Me | N | |
| 2.704 | " | " | " | " | Me | Me | CH | |
| 2.705 | " | " | " | " | Cl | OMe | N | |
| 2.706 | " | " | " | Me | OMe | Me | N | |
| 2.707 | " | " | " | " | " | OMe | CH | |
| 2.708 | Allyl | " | CO₂-Me | H | OMe | OMe | CH | |
| 2.709 | " | " | " | " | " | Cl | CH | |
| 2.710 | " | " | " | " | Me | Me | CH | |
| 2.711 | " | " | " | " | OMe | Me | N | |
| 2.712 | " | " | CO₂-Et | H | OMe | OMe | CH | |
| 2.713 | " | " | CO₂-n-Pr | " | " | " | CH | |
| 2.714 | " | " | CO₂-i-Pr | " | " | " | CH | |
| 2.715 | Me | SO₂CH₃ | CO₂-Me | H | OMe | OMe | CH | 119° C. |
| 2.716 | " | " | " | " | " | OMe | N | |
| 2.717 | " | " | " | " | " | Me | N | |
| 2.718 | " | " | " | " | " | " | CH | |
| 2.719 | " | " | " | " | NMe₂ | OCH₂CF₃ | N | |
| 2.720 | " | " | " | " | Me | Me | CH | |
| 2.721 | " | " | " | " | " | " | N | |
| 2.722 | " | " | " | " | Cl | OMe | CH | |
| 2.723 | " | " | " | Me | OMe | OMe | CH | |
| 2.724 | " | " | " | " | " | Me | N | |
| 2.725 | " | " | CO₂-Et | H | OMe | OMe | CH | |
| 2.726 | " | " | " | " | " | Cl | CH | |
| 2.727 | " | " | " | " | Me | Me | CH | |
| 2.728 | " | " | " | " | OMe | Me | N | |
| 2.729 | " | " | " | " | NMe₂ | OCH₂CF₃ | N | |
| 2.730 | " | " | " | Me | OMe | OMe | CH | |
| 2.731 | " | " | " | " | OMe | Me | N | |
| 2.732 | " | " | CO₂-n-Pr | H | OMe | OMe | CH | |
| 2.733 | " | " | " | " | " | " | N | |
| 2.734 | " | " | " | " | OMe | Me | N | |
| 2.735 | " | " | " | " | Me | Me | CH | |
| 2.736 | " | " | " | " | OMe | Cl | CH | |
| 2.737 | " | " | " | Me | Me | OMe | N | |
| 2.738 | " | " | " | " | OMe | OMe | CH | |
| 2.739 | Me | SO₂Me | CO₂-i-Pr | H | OMe | OMe | CH | |
| 2.740 | " | " | " | " | " | " | N | |
| 2.741 | " | " | " | " | OMe | Me | N | |
| 2.742 | " | " | " | " | OMe | Cl | CH | |
| 2.743 | " | " | " | " | Me | Me | CH | |
| 2.744 | " | " | " | " | SMe | NEt₂ | N | |
| 2.745 | " | " | CO₂-i-Pr | Me | OMe | Me | N | |
| 2.746 | " | " | " | " | OMe | OMe | CH | |
| 2.747 | Me | " | CO₂-Allyl | H | OMe | OMe | CH | |
| 2.748 | Et | " | CO₂-Me | H | OMe | OMe | CH | |
| 2.749 | " | " | " | H | OMe | Me | N | |
| 2.750 | " | " | " | " | Me | Me | CH | |
| 2.751 | " | " | " | " | Cl | OMe | CH | |
| 2.752 | " | " | " | Me | OMe | OMe | CH | |
| 2.753 | " | " | " | " | OMe | Me | N | |
| 2.754 | " | " | CO₂-Et | H | OMe | OMe | CH | |
| 2.755 | " | " | " | " | OMe | Me | CH | |
| 2.756 | " | " | " | " | Cl | OMe | CH | |
| 2.757 | " | " | " | " | OMe | Me | N | |
| 2.758 | " | " | " | Me | OMe | OMe | CH | |
| 2.759 | " | " | " | " | " | Me | N | |
| 2.760 | " | " | CO₂-n-Pr | H | OMe | OMe | CH | |
| 2.761 | " | " | " | " | OMe | Me | N | |
| 2.762 | " | " | " | " | OMe | Cl | CH | |
| 2.763 | " | " | " | " | Me | Me | CH | |

TABLE 1-continued

| No. | R¹ | R² | R³ | R⁴ | X | Y | Z | m.p. |
|---|---|---|---|---|---|---|---|---|
| 2.764 | " | " | " | Me | OMe | OMe | CH | |
| 2.765 | " | " | " | " | OMe | Me | N | |
| 2.766 | " | " | CO₂-i-Pr | H | OMe | OMe | CH | |
| 2.767 | " | " | " | " | OMe | Me | N | |
| 2.768 | " | " | " | " | Me | Me | CH | |
| 2.769 | " | " | " | Me | OMe | Me | N | |
| 2.770 | n-Pr | SO₂Me | CO₂-Me | H | OMe | OMe | CH | |
| 2.771 | " | " | " | " | " | Cl | CH | |
| 2.772 | " | " | " | " | Me | Me | CH | |
| 2.773 | " | " | " | " | OMe | Me | N | |
| 2.774 | " | " | " | Me | OMe | OMe | CH | |
| 2.775 | " | " | " | " | OMe | Me | N | |
| 2.776 | n-Pr | " | CO₂-Et | H | " | " | N | |
| 2.777 | " | " | " | " | " | OMe | CH | |
| 2.778 | " | " | " | " | Me | Me | CH | |
| 2.779 | " | " | CO₂-n-Pr | " | OMe | OMe | CH | |
| 2.780 | i-Pr | " | CO₂-Me | H | OMe | OMe | CH | |
| 2.781 | " | " | " | " | OMe | Me | N | |
| 2.782 | " | " | " | " | Me | Me | CH | |
| 2.783 | " | " | " | " | Cl | OMe | N | |
| 2.784 | " | " | " | Me | OMe | Me | N | |
| 2.785 | " | " | " | " | " | OMe | CH | |
| 2.786 | Allyl | " | CO₂-Me | H | OMe | OMe | CH | |
| 2.787 | " | " | " | " | " | Cl | CH | |
| 2.788 | Allyl | " | CO₂-Me | H | OMe | OMe | CH | |
| 2.789 | " | " | " | " | " | Cl | CH | |
| 2.790 | " | " | " | " | Me | Me | CH | |
| 2.791 | " | " | " | " | OMe | Me | N | |
| 2.792 | " | " | CO₂-Et | H | OMe | OMe | CH | |
| 2.793 | " | " | CO₂-n-Pr | " | " | " | CH | |
| 2.794 | " | " | CO₂-i-Pr | " | " | " | CH | |
| 2.795 | Me | CONH—CH₂CH₂Cl | CO₂-Me | H | OMe | OMe | CH | |
| 2.796 | " | " | " | " | " | OMe | N | |
| 2.797 | " | " | " | " | " | Me | N | |
| 2.798 | " | " | " | " | " | " | CH | |
| 2.799 | " | " | " | " | NMe₂ | OCH₂CF₃ | N | |
| 2.800 | " | " | " | " | Me | Me | CH | |
| 2.801 | " | " | " | " | " | " | N | |
| 2.802 | " | " | " | " | Cl | OMe | CH | |
| 2.803 | " | " | " | Me | OMe | OMe | CH | |
| 2.804 | " | " | " | " | " | Me | N | |
| 2.805 | " | " | CO₂-Et | H | OMe | OMe | CH | |
| 2.806 | " | " | " | " | " | Cl | CH | |
| 2.807 | " | " | " | " | Me | Me | CH | |
| 2.808 | " | " | " | " | OMe | Me | N | |
| 2.809 | " | " | " | " | NMe₂ | OCH₂CF₃ | N | |
| 2.810 | " | " | " | Me | OMe | OMe | CH | |
| 2.811 | " | " | " | " | OMe | Me | N | |
| 2.812 | " | " | CO₂-n-Pr | H | OMe | OMe | CH | |
| 2.813 | " | " | " | " | " | " | N | |
| 2.814 | " | " | " | " | OMe | Me | N | |
| 2.815 | " | " | " | " | Me | Me | CH | |
| 2.816 | " | " | " | " | OMe | Cl | CH | |
| 2.817 | " | " | " | Me | Me | OMe | N | |
| 2.818 | " | " | " | " | OMe | OMe | CH | |
| 2.819 | Me | CO—NHCH₂CH₂Cl | CO₂-i-Pr | H | OMe | OMe | CH | |
| 2.820 | " | " | " | " | " | " | N | |
| 2.821 | " | " | " | " | OMe | Me | N | |
| 2.822 | " | " | " | " | OMe | Cl | CH | |
| 2.823 | " | " | " | " | Me | Me | CH | |
| 2.824 | " | " | " | " | SMe | NEt₂ | N | |
| 2.825 | " | " | CO₂-i-Pr | Me | OMe | Me | N | |
| 2.826 | " | " | " | " | OMe | OMe | CH | |
| 2.827 | Me | " | CO₂-Allyl | H | OMe | OMe | CH | |
| 2.828 | Et | " | CO₂-Me | H | OMe | OMe | CH | |
| 2.829 | " | " | " | H | OMe | Me | N | |

TABLE 1-continued

[Structure: R¹R²N-phenyl(R³)-SO₂NH-CO-NR⁴-[ring with N, X, Y, Z]]

| No. | R¹ | R² | R³ | R⁴ | X | Y | Z | m.p. |
|---|---|---|---|---|---|---|---|---|
| 2.830 | " | " | " | " | Me | Me | CH | |
| 2.831 | " | " | " | " | Cl | OMe | CH | |
| 2.832 | " | " | " | Me | OMe | OMe | CH | |
| 2.833 | " | " | " | " | OMe | Me | N | |
| 2.834 | " | " | CO₂-Et | H | OMe | OMe | CH | |
| 2.835 | " | " | " | " | OMe | Me | CH | |
| 2.836 | " | " | " | " | Cl | OMe | CH | |
| 2.837 | " | " | " | " | OMe | Me | N | |
| 2.838 | " | " | " | Me | OMe | OMe | CH | |
| 2.839 | " | " | " | " | " | Me | N | |
| 2.840 | " | " | CO₂-n-Pr | H | OMe | OMe | CH | |
| 2.841 | " | " | " | H | OMe | Me | N | |
| 2.842 | " | " | " | " | OMe | Cl | CH | |
| 2.843 | " | " | " | " | Me | Me | CH | |
| 2.844 | " | " | " | Me | OMe | OMe | CH | |
| 2.845 | " | " | " | " | OMe | Me | N | |
| 2.846 | " | " | CO₂-i-Pr | H | OMe | OMe | CH | |
| 2.847 | " | " | " | H | OMe | Me | N | |
| 2.848 | " | " | " | " | Me | Me | CH | |
| 2.849 | " | " | " | Me | OMe | Me | N | |
| 2.850 | n-Pr | CO—NH—CH₂CH₂Cl | CO₂Me | H | OMe | OMe | CH | |
| 2.851 | " | " | " | " | " | Cl | CH | |
| 2.852 | " | " | " | " | Me | Me | CH | |
| 2.853 | " | " | " | " | OMe | Me | N | |
| 2.854 | " | " | " | Me | OMe | OMe | CH | |
| 2.855 | " | " | " | " | OMe | Me | N | |
| 2.856 | n-Pr | " | CO₂-Et | H | " | " | N | |
| 2.857 | " | " | " | " | " | OMe | CH | |
| 2.858 | " | " | " | " | Me | Me | CH | |
| 2.859 | " | " | CO₂-n-Pr | " | OMe | OMe | CH | |
| 2.860 | i-Pr | " | CO₂-Me | H | OMe | OMe | CH | |
| 2.861 | " | " | " | " | OMe | Me | N | |
| 2.862 | " | " | " | " | Me | Me | CH | |
| 2.863 | " | " | " | " | Cl | OMe | N | |
| 2.864 | " | " | " | Me | OMe | Me | N | |
| 2.865 | " | " | " | " | " | OMe | CH | |
| 2.866 | Allyl | " | CO₂-Me | H | OMe | OMe | CH | |
| 2.867 | " | " | " | " | " | Cl | CH | |
| 2.868 | " | " | " | " | Me | Me | CH | |
| 2.869 | " | " | " | " | OMe | Me | N | |
| 2.870 | " | " | CO₂-Et | H | OMe | OMe | CH | |
| 2.871 | " | " | CO₂-n-Pr | " | " | " | CH | |
| 2.872 | " | " | CO₂-i-Pr | " | " | " | CH | |
| 2.873 | Me | CO—OCH₂CCl₃ | CO₂-Me | H | OMe | OMe | CH | |
| 2.874 | " | " | " | " | " | OMe | N | |
| 2.875 | " | " | " | " | " | Me | N | |
| 2.876 | " | " | " | " | " | " | CH | |
| 2.877 | " | " | " | " | NMe₂ | OCH₂CF₃ | N | |
| 2.878 | " | " | " | " | Me | Me | CH | |
| 2.879 | " | " | " | " | " | " | N | |
| 2.880 | " | " | " | " | Cl | OMe | CH | |
| 2.881 | " | " | " | Me | OMe | OMe | CH | |
| 2.882 | " | " | " | " | " | Me | N | |
| 2.883 | " | " | CO₂-Et | H | OMe | OMe | CH | |
| 2.884 | " | " | " | " | " | Cl | CH | |
| 2.885 | " | " | " | " | Me | Me | CH | |
| 2.886 | " | " | " | " | OMe | Me | N | |
| 2.887 | " | " | " | " | NMe₂ | OCH₂CF₃ | N | |
| 2.888 | " | " | " | Me | OMe | OMe | CH | |
| 2.889 | " | " | " | " | OMe | Me | N | |
| 2.890 | " | " | CO₂-n-Pr | H | OMe | OMe | CH | |
| 2.891 | " | " | " | " | " | " | N | |
| 2.892 | " | " | " | " | OMe | Me | N | |
| 2.893 | " | " | " | " | Me | Me | CH | |
| 2.894 | " | " | " | " | OMe | Cl | CH | |
| 2.895 | " | " | " | Me | Me | OMe | N | |
| 2.896 | " | " | " | " | OMe | OMe | CH | |

TABLE 1-continued

| No. | R¹ | R² | R³ | R⁴ | X | Y | Z | m.p. |
|---|---|---|---|---|---|---|---|---|
| 2.897 | Me | CO—OCH₂CCl₃ | CO₂-i-Pr | H | OMe | OMe | CH | |
| 2.898 | " | " | " | " | " | " | N | |
| 2.899 | " | " | " | " | OMe | Me | N | |
| 2.900 | " | " | " | " | OMe | Cl | CH | |
| 2.901 | " | " | " | " | Me | Me | CH | |
| 2.902 | " | " | " | " | SMe | NEt₂ | N | |
| 2.903 | " | " | CO₂-i-Pr | Me | OMe | Me | N | |
| 2.904 | " | " | " | " | OMe | OMe | CH | |
| 2.905 | Me | " | CO₂-Allyl | H | OMe | OMe | CH | |
| 2.906 | Et | " | CO₂-Me | H | OMe | OMe | CH | |
| 2.907 | " | " | " | H | OMe | Me | N | |
| 2.908 | " | " | " | " | Me | Me | CH | |
| 2.909 | " | " | " | " | Cl | OMe | CH | |
| 2.910 | " | " | " | Me | OMe | OMe | CH | |
| 2.911 | " | " | " | " | OMe | Me | N | |
| 2.912 | " | " | CO₂-Et | H | OMe | OMe | CH | |
| 2.913 | " | " | " | " | OMe | Me | CH | |
| 2.914 | " | " | " | " | Cl | OMe | CH | |
| 2.915 | " | " | " | " | OMe | Me | N | |
| 2.916 | " | " | " | Me | OMe | OMe | CH | |
| 2.917 | " | " | " | " | " | Me | N | |
| 2.918 | " | " | CO₂-n-Pr | H | OMe | OMe | CH | |
| 2.919 | " | " | " | " | OMe | Me | N | |
| 2.920 | " | " | " | " | OMe | Cl | CH | |
| 2.921 | " | " | " | " | Me | Me | CH | |
| 2.922 | " | " | " | Me | OMe | OMe | CH | |
| 2.923 | " | " | " | " | OMe | Me | N | |
| 2.924 | " | " | CO₂-i-Pr | H | OMe | OMe | CH | |
| 2.925 | " | " | " | " | OMe | Me | N | |
| 2.926 | " | " | " | " | Me | Me | CH | |
| 2.927 | " | " | " | Me | OMe | Me | N | |
| 2.928 | n-Pr | CO—OCH₂CCl₃ | CO₂-Me | H | OMe | OMe | CH | |
| 2.929 | " | " | " | " | " | Cl | CH | |
| 2.930 | " | " | " | " | Me | Me | CH | |
| 2.931 | " | " | " | " | OMe | Me | N | |
| 2.932 | " | " | " | Me | OMe | OMe | CH | |
| 2.933 | " | " | " | " | OMe | Me | N | |
| 2.934 | n-Pr | " | CO₂-Et | H | OMe | Me | N | |
| 2.935 | " | " | " | " | " | OMe | CH | |
| 2.936 | " | " | " | " | Me | Me | CH | |
| 2.937 | " | " | CO₂-n-Pr | " | OMe | OMe | CH | |
| 2.938 | i-Pr | " | CO₂-Me | H | OMe | OMe | CH | |
| 2.939 | " | " | " | " | OMe | Me | N | |
| 2.940 | " | " | " | " | Me | Me | CH | |
| 2.941 | " | " | " | " | Cl | OMe | N | |
| 2.942 | " | " | " | Me | OMe | Me | N | |
| 2.943 | " | " | " | " | " | OMe | CH | |
| 2.944 | Allyl | " | CO₂-Me | H | OMe | OMe | CH | |
| 2.945 | " | " | " | " | " | Cl | CH | |
| 2.946 | " | " | " | " | Me | Me | CH | |
| 2.947 | " | " | " | " | OMe | Me | N | |
| 2.948 | " | " | CO₂-Et | H | OMe | OMe | CH | |
| 2.949 | " | " | CO₂-n-Pr | H | OMe | OMe | CH | |
| 2.950 | " | " | CO₂-i-Pr | " | " | " | CH | |
| 2.951 | Me | COCH₂Br | CO₂-Me | H | OMe | OMe | CH | 155–161 |
| 2.952 | " | " | " | " | " | OMe | N | |
| 2.953 | " | " | " | " | " | Me | N | |
| 2.954 | " | " | " | " | " | " | CH | |
| 2.955 | " | " | " | " | NMe₂ | OCH₂CF₃ | N | |
| 2.956 | " | " | " | " | Me | Me | CH | |
| 2.957 | " | " | " | " | " | " | N | |
| 2.958 | " | " | " | " | Cl | OMe | CH | |
| 2.959 | " | " | " | Me | OMe | OMe | CH | |
| 2.960 | " | " | " | " | " | Me | N | |
| 2.961 | " | " | CO₂-Et | H | OMe | OMe | CH | |
| 2.962 | " | " | " | " | " | Cl | CH | |
| 2.963 | " | " | " | " | Me | Me | CH | |
| 2.964 | " | " | " | " | OMe | Me | N | |

TABLE 1-continued

| No. | R¹ | R² | R³ | R⁴ | X | Y | Z | m.p. |
|---|---|---|---|---|---|---|---|---|
| 2.965 | " | " | " | " | NMe₂ | OCH₂CF₃ | N | |
| 2.966 | " | " | " | Me | OMe | OMe | CH | |
| 2.967 | " | " | " | " | OMe | Me | N | |
| 2.968 | " | " | CO₂-n-Pr | H | OMe | OMe | CH | |
| 2.969 | " | " | " | " | " | " | N | |
| 2.970 | " | " | " | " | OMe | Me | N | |
| 2.971 | " | " | " | " | Me | Me | CH | |
| 2.972 | " | " | " | " | OMe | Cl | CH | |
| 2.973 | " | " | " | Me | Me | OMe | N | |
| 2.974 | " | " | " | " | OMe | OMe | CH | |
| 2.975 | Me | COCH₂Br | CO₂-i-Pr | H | " | " | CH | |
| 2.976 | " | " | " | " | " | " | N | |
| 2.977 | " | " | " | " | H | Me | N | |
| 2.978 | " | " | " | " | OMe | Cl | CH | |
| 2.979 | " | " | " | " | Me | Me | CH | |
| 2.980 | " | " | " | " | SMe | NEt₂ | N | |
| 2.981 | " | " | CO₂-i-Pr | Me | OMe | Me | N | |
| 2.982 | " | " | " | " | OMe | OMe | CH | |
| 2.983 | Me | " | CO₂-Allyl | H | OMe | OMe | CH | |
| 2.984 | Et | " | CO₂-Me | H | OMe | OMe | CH | |
| 2.985 | " | " | " | H | OMe | Me | N | |
| 2.986 | " | " | " | " | Me | Me | CH | |
| 2.987 | " | " | " | " | Cl | OMe | CH | |
| 2.988 | " | " | " | Me | OMe | OMe | CH | |
| 2.989 | " | " | " | " | OMe | Me | N | |
| 2.990 | " | " | CO₂-Et | H | OMe | OMe | CH | |
| 2.991 | " | " | " | " | OMe | Me | CH | |
| 2.992 | " | " | " | " | Cl | OMe | CH | |
| 2.993 | " | " | " | " | OMe | Me | N | |
| 2.994 | " | " | " | Me | OMe | OMe | CH | |
| 2.995 | " | " | " | " | " | Me | N | |
| 2.996 | " | " | CO₂-n-Pr | H | OMe | OMe | CH | |
| 2.997 | " | " | " | " | OMe | Me | N | |
| 2.998 | " | " | " | " | OMe | Cl | CH | |
| 2.999 | " | " | " | " | Me | Me | CH | |
| 3.000 | " | " | " | Me | OMe | OMe | CH | |
| 3.001 | " | " | " | " | OMe | Me | N | |
| 3.002 | " | " | CO₂-i-Pr | H | OMe | OMe | CH | |
| 3.003 | " | " | " | " | OMe | Me | N | |
| 3.004 | " | " | " | " | Me | Me | CH | |
| 3.005 | " | " | " | Me | OMe | Me | N | |
| 3.006 | n-Pr | COCH₂Br | CO₂-Me | H | OMe | OMe | CH | |
| 3.007 | " | " | " | " | " | Cl | CH | |
| 3.008 | " | " | " | " | Me | Me | CH | |
| 3.009 | " | " | " | " | OMe | Me | N | |
| 3.010 | " | " | " | Me | OMe | OMe | CH | |
| 3.011 | " | " | " | " | OMe | Me | N | |
| 3.012 | n-Pr | " | CO₂-Et | H | " | " | N | |
| 3.013 | " | " | " | " | " | OMe | CH | |
| 3.014 | " | " | " | " | Me | Me | CH | |
| 3.015 | " | " | CO₂-n-Pr | " | OMe | OMe | CH | |
| 3.016 | i-Pr | " | CO₂-Me | H | OMe | OMe | CH | |
| 3.017 | " | " | " | " | OMe | Me | N | |
| 3.018 | " | " | " | " | Me | Me | CH | |
| 3.019 | " | " | " | " | Cl | OMe | N | |
| 3.020 | " | " | " | Me | OMe | Me | N | |
| 3.021 | " | " | " | " | " | OMe | CH | |
| 3.022 | Allyl | " | CO₂-Me | H | OMe | OMe | CH | |
| 3.023 | " | " | " | " | " | Cl | CH | |
| 3.024 | " | " | " | " | Me | Me | CH | |
| 3.025 | " | " | " | " | OMe | Me | N | |
| 3.026 | " | " | CO₂-Et | H | OMe | OMe | CH | |
| 3.027 | " | " | CO₂-n-Pr | " | " | " | CH | |
| 3.028 | " | " | CO₂-i-Pr | " | " | " | CH | |
| 3.029 | Me | COCCl₃ | CO₂-Me | H | OMe | OMe | CH | |
| 3.030 | " | " | " | " | " | OMe | N | |
| 3.031 | " | " | " | " | " | Me | N | |
| 3.032 | " | " | " | " | " | " | CH | |

TABLE 1-continued

![Structure: R¹R²N-phenyl(R³)-SO₂NH-CO-NR⁴-pyrimidine/triazine with X, Y, Z substituents]

| No. | R¹ | R² | R³ | R⁴ | X | Y | Z | m.p. |
|---|---|---|---|---|---|---|---|---|
| 3.033 | " | " | " | " | NMe₂ | OCH₂CF₃ | N | |
| 3.034 | " | " | " | " | Me | Me | CH | |
| 3.035 | " | " | " | " | " | " | N | |
| 3.036 | " | " | " | " | Cl | OMe | CH | |
| 3.037 | " | " | " | Me | OMe | OMe | CH | |
| 3.038 | " | " | " | " | " | Me | N | |
| 3.039 | " | " | CO₂-Et | H | OMe | OMe | CH | |
| 3.040 | " | " | " | " | " | Cl | CH | |
| 3.041 | " | " | " | " | Me | Me | CH | |
| 3.042 | " | " | " | " | OMe | Me | N | |
| 3.043 | " | " | " | " | NMe₂ | OCH₂CF₃ | N | |
| 3.044 | " | " | " | Me | OMe | OMe | CH | |
| 3.045 | " | " | " | " | OMe | Me | N | |
| 3.046 | " | " | CO₂-n-Pr | H | OMe | OMe | CH | |
| 3.047 | " | " | " | " | " | " | N | |
| 3.048 | " | " | " | " | OMe | Me | N | |
| 3.049 | " | " | " | " | Me | Me | CH | |
| 3.050 | " | " | " | " | OMe | Cl | CH | |
| 3.051 | " | " | " | Me | Me | OMe | N | |
| 3.052 | " | " | " | " | OMe | OMe | CH | |
| 3.053 | Me | COCCl₃ | CO₂-i-Pr | H | OMe | OMe | CH | |
| 3.054 | " | " | " | " | " | " | N | |
| 3.055 | " | " | " | " | OMe | Me | N | |
| 3.056 | " | " | " | " | OMe | Cl | CH | |
| 3.057 | " | " | " | " | Me | Me | CH | |
| 3.058 | " | " | " | " | SMe | NEt₂ | N | |
| 3.059 | " | " | CO₂-i-Pr | Me | OMe | Me | N | |
| 3.060 | " | " | " | " | OMe | OMe | CH | |
| 3.061 | Me | " | CO₂-Allyl | H | OMe | OMe | CH | |
| 3.062 | Et | " | CO₂-Me | H | OMe | OMe | CH | |
| 3.063 | " | " | " | H | OMe | Me | N | |
| 3.064 | " | " | " | " | Me | Me | CH | |
| 3.065 | " | " | " | " | Cl | OMe | CH | |
| 3.066 | " | " | " | Me | OMe | OMe | CH | |
| 3.067 | " | " | " | " | OMe | Me | N | |
| 3.068 | " | " | CO₂-Et | H | OMe | OMe | CH | |
| 3.069 | " | " | " | " | OMe | Me | CH | |
| 3.070 | " | " | " | " | Cl | OMe | CH | |
| 3.071 | " | " | " | " | OMe | Me | N | |
| 3.072 | " | " | " | Me | OMe | OMe | CH | |
| 3.073 | " | " | " | " | " | Me | N | |
| 3.074 | " | " | CO₂-n-Pr | H | OMe | OMe | CH | |
| 3.075 | " | " | " | " | OMe | Me | N | |
| 3.076 | " | " | " | " | OMe | Cl | CH | |
| 3.077 | " | " | " | " | Me | Me | CH | |
| 3.078 | " | " | " | Me | OMe | OMe | CH | |
| 3.079 | " | " | " | " | OMe | Me | N | |
| 3.080 | " | " | CO₂-i-Pr | H | OMe | OMe | CH | |
| 3.081 | " | " | " | " | OMe | Me | N | |
| 3.082 | " | " | " | " | Me | Me | CH | |
| 3.083 | " | " | " | Me | OMe | Me | N | |
| 3.084 | n-Pr | COCCl₃ | CO₂-Me | H | OMe | OMe | CH | |
| 3.085 | " | " | " | " | " | Cl | CH | |
| 3.086 | " | " | " | " | Me | Me | CH | |
| 3.087 | " | " | " | " | OMe | Me | N | |
| 3.088 | " | " | " | Me | OMe | OMe | CH | |
| 3.089 | " | " | " | " | OMe | Me | N | |
| 3.090 | n-Pr | " | CO₂-Et | H | " | " | N | |
| 3.091 | " | " | " | " | " | OMe | CH | |
| 3.092 | " | " | " | " | Me | Me | CH | |
| 3.093 | " | " | CO₂-n-Pr | " | OMe | OMe | CH | |
| 3.094 | i-Pr | " | CO₂-Me | H | OMe | OMe | CH | |
| 3.095 | " | " | " | " | OMe | Me | N | |
| 3.096 | " | " | " | " | Me | Me | CH | |
| 3.097 | " | " | " | " | Cl | OMe | N | |
| 3.098 | " | " | " | Me | OMe | Me | N | |
| 3.099 | " | " | " | " | " | OMe | CH | |
| 3.100 | Allyl | " | CO₂-Me | H | OMe | OMe | CH | |

TABLE 1-continued

| No. | R¹ | R² | R³ | R⁴ | X | Y | Z | m.p. |
|---|---|---|---|---|---|---|---|---|
| 3.101 | " | " | " | " | " | Cl | CH | |
| 3.102 | " | " | " | " | Me | Me | CH | |
| 3.103 | " | " | " | " | OMe | Me | N | |
| 3.104 | " | " | CO₂-Et | H | OMe | OMe | CH | |
| 3.105 | " | " | CO₂-n-Pr | " | " | " | CH | |
| 3.106 | " | " | CO₂-i-Pr | " | " | " | CH | |
| 3.107 | Me | COCHCl₂ | CO₂-Me | H | OMe | OMe | CH | |
| 3.108 | " | " | " | " | " | " | OMe | N |
| 3.109 | " | " | " | " | " | " | Me | N |
| 3.110 | " | " | " | " | " | " | " | CH |
| 3.111 | " | " | " | " | NMe₂ | OCH₂CF₃ | N | |
| 3.112 | " | " | " | " | Me | Me | CH | |
| 3.113 | " | " | " | " | " | " | N | |
| 3.114 | " | " | " | " | Cl | OMe | CH | |
| 3.115 | " | " | " | Me | OMe | OMe | CH | |
| 3.116 | " | " | " | " | " | Me | N | |
| 3.117 | " | " | CO₂-Et | H | OMe | OMe | CH | |
| 3.118 | " | " | " | " | " | Cl | CH | |
| 3.119 | " | " | " | " | Me | Me | CH | |
| 3.120 | " | " | " | " | OMe | Me | N | |
| 3.121 | " | " | " | " | NMe₂ | OCH₂CF₃ | N | |
| 3.122 | " | " | " | Me | OMe | OMe | CH | |
| 3.123 | " | " | " | " | OMe | Me | N | |
| 3.124 | " | " | CO₂-n-Pr | H | OMe | OMe | CH | |
| 3.125 | " | " | " | " | " | " | N | |
| 3.126 | " | " | " | " | OMe | Me | N | |
| 3.127 | " | " | " | " | Me | Me | CH | |
| 3.128 | " | " | " | " | OMe | Cl | CH | |
| 3.129 | " | " | " | Me | Me | OMe | N | |
| 3.130 | " | " | " | " | OMe | OMe | CH | |
| 3.131 | Me | COCHCl₂ | CO₂-i-Pr | H | OMe | OMe | CH | |
| 3.132 | " | " | " | " | " | " | N | |
| 3.133 | " | " | " | " | OMe | Me | N | |
| 3.134 | " | " | " | " | OMe | Cl | CH | |
| 3.135 | " | " | " | " | Me | Me | CH | |
| 3.136 | " | " | " | " | SMe | NEt₂ | N | |
| 3.137 | " | " | CO₂-i-Pr | Me | OMe | Me | N | |
| 3.138 | " | " | " | " | OMe | OMe | CH | |
| 3.139 | Me | " | CO₂-Allyl | H | OMe | OMe | CH | |
| 3.140 | Et | " | CO₂-Me | H | OMe | OMe | CH | |
| 3.141 | " | " | " | H | OMe | Me | N | |
| 3.142 | " | " | " | " | Me | Me | CH | |
| 3.143 | " | " | " | " | Cl | OMe | CH | |
| 3.144 | " | " | " | Me | OMe | OMe | CH | |
| 3.145 | " | " | " | " | OMe | Me | N | |
| 3.146 | " | " | CO₂-Et | H | OMe | OMe | CH | |
| 3.147 | " | " | " | " | OMe | Me | CH | |
| 3.148 | " | " | " | " | Cl | OMe | CH | |
| 3.149 | " | " | " | " | OMe | Me | N | |
| 3.150 | " | " | " | Me | OMe | OMe | CH | |
| 3.151 | " | " | " | " | " | Me | N | |
| 3.152 | " | " | CO₂-n-Pr | H | OMe | OMe | CH | |
| 3.153 | " | " | " | " | OMe | Me | N | |
| 3.154 | " | " | " | " | OMe | Cl | CH | |
| 3.155 | " | " | " | " | Me | Me | CH | |
| 3.156 | " | " | " | Me | OMe | OMe | CH | |
| 3.157 | " | " | " | " | OMe | Me | N | |
| 3.158 | " | " | CO₂-i-Pr | H | OMe | OMe | CH | |
| 3.159 | " | " | " | " | OMe | Me | N | |
| 3.160 | " | " | " | " | Me | Me | CH | |
| 3.161 | " | " | " | Me | OMe | Me | N | |
| 3.162 | n-Pr | COCHCl₂ | CO₂-Me | H | OMe | OMe | CH | |
| 3.163 | " | " | " | " | " | Cl | CH | |
| 3.164 | " | " | " | " | Me | Me | CH | |
| 3.165 | " | " | " | " | OMe | Me | N | |
| 3.166 | " | " | " | Me | OMe | OMe | CH | |
| 3.167 | " | " | " | " | OMe | Me | N | |
| 3.168 | n-Pr | " | CO₂-Et | H | " | " | N | |

TABLE 1-continued

| No. | R¹ | R² | R³ | R⁴ | X | Y | Z | m.p. |
|---|---|---|---|---|---|---|---|---|
| 3.169 | " | " | " | " | " | OMe | CH | |
| 3.170 | " | " | " | " | Me | Me | CH | |
| 3.171 | " | " | $CO_2$-n-Pr | " | OMe | OMe | CH | |
| 3.172 | i-Pr | " | $CO_2$-Me | H | OMe | OMe | CH | |
| 3.173 | " | " | " | " | OMe | Me | N | |
| 3.174 | " | " | " | " | Me | Me | CH | |
| 3.175 | " | " | " | " | Cl | OMe | N | |
| 3.176 | " | " | " | Me | OMe | Me | N | |
| 3.177 | " | " | " | " | " | OMe | CH | |
| 3.178 | Allyl | " | $CO_2$-Me | H | OMe | OMe | CH | |
| 3.179 | " | " | " | " | " | Cl | CH | |
| 3.180 | " | " | " | " | Me | Me | CH | |
| 3.181 | " | " | " | " | OMe | Me | N | |
| 3.182 | " | " | $CO_2$-Et | H | OMe | OMe | CH | |
| 3.183 | " | " | $CO_2$-n-Pr | " | " | " | CH | |
| 3.184 | " | " | $CO_2$-i-Pr | " | " | " | CH | |
| 3.185 | Me | $COCH_2Cl$ | $CO_2$-Me | H | OMe | OMe | CH | |
| 3.186 | " | " | " | " | " | OMe | N | |
| 3.187 | " | " | " | " | " | Me | N | |
| 3.188 | " | " | " | " | " | " | CH | |
| 3.189 | " | " | " | " | $NMe_2$ | $OCH_2CF_3$ | N | |
| 3.190 | " | " | " | " | Me | Me | CH | |
| 3.191 | " | " | " | " | " | " | N | |
| 3.192 | " | " | " | " | Cl | OMe | CH | |
| 3.193 | " | " | " | Me | OMe | OMe | CH | |
| 3.194 | " | " | " | " | " | Me | N | |
| 3.195 | " | " | $CO_2$-Et | H | OMe | OMe | CH | |
| 3.196 | " | " | " | " | " | Cl | CH | |
| 3.197 | " | " | " | " | Me | Me | CH | |
| 3.198 | " | " | " | " | OMe | Me | N | |
| 3.199 | " | " | " | " | $NMe_2$ | $OCH_2CF_3$ | N | |
| 3.200 | " | " | " | Me | OMe | OMe | CH | |
| 3.201 | " | " | " | " | OMe | Me | N | |
| 3.202 | " | " | $CO_2$-n-Pr | H | OMe | OMe | CH | |
| 3.203 | " | " | " | " | " | " | N | |
| 3.204 | " | " | " | " | OMe | Me | N | |
| 3.205 | " | " | " | " | Me | Me | CH | |
| 3.206 | " | " | " | " | OMe | Cl | CH | |
| 3.207 | " | " | " | Me | Me | OMe | N | |
| 3.208 | " | " | " | " | OMe | OMe | CH | |
| 3.209 | Me | $COCH_2Cl$ | $CO_2$-i-Pr | H | OMe | OMe | CH | |
| 3.210 | " | " | " | " | " | " | N | |
| 3.211 | " | " | " | " | OMe | Me | N | |
| 3.212 | " | " | " | " | OMe | Cl | CH | |
| 3.213 | " | " | " | " | Me | Me | CH | |
| 3.214 | " | " | " | " | SMe | $NEt_2$ | N | |
| 3.215 | " | " | $CO_2$-i-Pr | Me | OMe | Me | N | |
| 3.216 | " | " | " | " | OMe | OMe | CH | |
| 3.217 | Me | " | $CO_2$-Allyl | H | OMe | OMe | CH | |
| 3.218 | Et | " | $CO_2$-Me | H | OMe | OMe | CH | |
| 3.219 | " | " | " | H | OMe | Me | N | |
| 3.220 | " | " | " | " | Me | Me | CH | |
| 3.221 | " | " | " | " | Cl | OMe | CH | |
| 3.222 | " | " | " | Me | OMe | OMe | CH | |
| 3.223 | " | " | " | " | OMe | Me | N | |
| 3.224 | " | " | $CO_2$-Et | H | OMe | OMe | CH | |
| 3.225 | " | " | " | " | OMe | Me | CH | |
| 3.226 | " | " | " | " | Cl | OMe | CH | |
| 3.227 | " | " | " | " | OMe | Me | N | |
| 3.228 | " | " | " | Me | OMe | OMe | CH | |
| 3.229 | " | " | " | " | " | Me | N | |
| 3.230 | " | " | $CO_2$-n-Pr | H | OMe | OMe | CH | |
| 3.231 | " | " | " | " | OMe | Me | N | |
| 3.232 | " | " | " | " | OMe | Cl | CH | |
| 3.233 | " | " | " | " | Me | Me | CH | |
| 3.234 | " | " | " | Me | OMe | OMe | CH | |
| 3.235 | " | " | " | " | OMe | Me | N | |
| 3.236 | " | " | $CO_2$-i-Pr | H | OMe | OMe | CH | |

TABLE 1-continued

| No. | R¹ | R² | R³ | R⁴ | X | Y | Z | m.p. |
|---|---|---|---|---|---|---|---|---|
| 3.237 | " | " | " | " | OMe | Me | N | |
| 3.238 | " | " | " | " | Me | Me | CH | |
| 3.239 | " | " | " | Me | OMe | Me | N | |
| 3.240 | n-Pr | COCH₂Cl | CO₂-Me | H | OMe | OMe | CH | |
| 3.241 | " | " | " | " | " | Cl | CH | |
| 3.242 | " | " | " | " | Me | Me | CH | |
| 3.243 | " | " | " | " | OMe | Me | N | |
| 3.244 | " | " | " | Me | OMe | OMe | CH | |
| 3.245 | " | " | " | " | OMe | Me | N | |
| 3.246 | n-Pr | " | CO₂-Et | H | " | " | N | |
| 3.247 | " | " | " | " | " | OMe | CH | |
| 3.248 | " | " | " | " | Me | Me | CH | |
| 3.249 | " | " | CO₂-n-Pr | " | OMe | OMe | CH | |
| 3.250 | i-Pr | " | CO₂-Me | H | OMe | OMe | CH | |
| 3.251 | " | " | " | " | OMe | Me | N | |
| 3.252 | " | " | " | " | Me | Me | CH | |
| 3.253 | " | " | " | " | Cl | OMe | N | |
| 3.254 | " | " | " | Me | OMe | Me | N | |
| 3.255 | " | " | " | " | " | OMe | CH | |
| 3.256 | Allyl | " | CO₂-Me | H | OMe | OMe | CH | |
| 3.257 | " | " | " | " | " | Cl | CH | |
| 3.258 | " | " | " | " | Me | Me | CH | |
| 3.259 | " | " | " | " | OMe | Me | N | |
| 3.260 | " | " | CO₂-Et | H | OMe | OMe | CH | |
| 3.261 | " | " | CO₂-n-Pr | " | " | " | CH | |
| 3.262 | " | " | CO₂-i-Pr | " | " | " | CH | |
| 3.263 | Me | COCF₃ | CO₂Me | H | OMe | OMe | CH | |
| 3.264 | " | " | " | " | " | OMe | N | |
| 3.265 | " | " | " | " | " | Me | N | |
| 3.266 | " | " | " | " | " | " | CH | |
| 3.267 | " | " | " | " | NMe₂ | OCH₂CF₃ | N | |
| 3.268 | " | " | " | " | Me | Me | CH | |
| 3.269 | " | " | " | " | " | " | N | |
| 3.270 | " | " | " | " | Cl | OMe | CH | |
| 3.271 | " | " | " | Me | OMe | OMe | CH | |
| 3.272 | " | " | " | " | " | Me | N | |
| 3.273 | " | " | CO₂-Et | H | OMe | OMe | CH | |
| 3.274 | " | " | " | " | " | Cl | CH | |
| 3.275 | " | " | " | " | Me | Me | CH | |
| 3.276 | " | " | " | " | OMe | Me | N | |
| 3.277 | " | " | " | " | NMe₂ | OCH₂CF₃ | N | |
| 3.278 | " | " | " | Me | OMe | OMe | CH | |
| 3.279 | " | " | " | " | OMe | Me | N | |
| 3.280 | " | " | CO₂-n-Pr | H | OMe | OMe | CH | |
| 3.281 | " | " | " | " | " | " | N | |
| 3.282 | " | " | " | " | OMe | Me | N | |
| 3.283 | " | " | " | " | Me | Me | CH | |
| 3.284 | " | " | " | " | OMe | Cl | CH | |
| 3.285 | " | " | " | Me | Me | OMe | N | |
| 3.286 | " | " | " | " | OMe | OMe | CH | |
| 3.287 | Me | COCF₃ | CO₂-i-Pr | H | OMe | OMe | CH | |
| 3.288 | " | " | " | " | " | " | N | |
| 3.289 | " | " | " | " | OMe | Me | N | |
| 3.290 | " | " | " | " | OMe | Cl | CH | |
| 3.291 | " | " | " | " | Me | Me | CH | |
| 3.292 | " | " | " | " | SMe | NEt₂ | N | |
| 3.293 | " | " | CO₂-i-Pr | Me | OMe | Me | N | |
| 3.294 | " | " | " | " | OMe | OMe | CH | |
| 3.295 | Me | " | CO₂-Allyl | H | OMe | OMe | CH | |
| 3.296 | Et | " | CO₂-Me | H | OMe | OMe | CH | |
| 3.297 | " | " | " | H | OMe | Me | N | |
| 3.298 | " | " | " | " | Me | Me | CH | |
| 3.299 | " | " | " | " | Cl | OMe | CH | |
| 3.300 | " | " | " | Me | OMe | OMe | CH | |
| 3.301 | " | " | " | " | OMe | Me | N | |
| 3.302 | " | " | CO₂-Et | H | OMe | OMe | CH | |
| 3.303 | " | " | " | " | OMe | Me | CH | |
| 3.304 | " | " | " | " | Cl | OMe | CH | |

TABLE 1-continued

[Structure: R¹R²N-phenyl(R³)-SO₂NH-CO-NR⁴-pyrimidine/triazine ring with X, Y, Z substituents]

| No. | R¹ | R² | R³ | R⁴ | X | Y | Z | m.p. |
|---|---|---|---|---|---|---|---|---|
| 3.305 | " | " | " | " | OMe | Me | N | |
| 3.306 | " | " | " | Me | OMe | OMe | CH | |
| 3.307 | " | " | " | " | " | Me | N | |
| 3.308 | " | " | CO₂-n-Pr | H | OMe | OMe | CH | |
| 3.309 | " | " | " | " | OMe | Me | N | |
| 3.310 | " | " | " | " | OMe | Cl | CH | |
| 3.311 | " | " | " | " | Me | Me | CH | |
| 3.312 | " | " | " | Me | OMe | OMe | CH | |
| 3.313 | " | " | " | " | OMe | Me | N | |
| 3.314 | " | " | CO₂-i-Pr | H | OMe | OMe | CH | |
| 3.315 | " | " | " | " | OMe | Me | N | |
| 3.316 | " | " | " | " | Me | Me | CH | |
| 3.317 | " | " | " | Me | OMe | Me | N | |
| 3.318 | n-Pr | COCF₃ | CO₂-Me | H | OMe | OMe | CH | |
| 3.319 | " | " | " | " | " | Cl | CH | |
| 3.320 | " | " | " | " | Me | Me | CH | |
| 3.321 | " | " | " | " | OMe | Me | N | |
| 3.322 | " | " | " | Me | OMe | OMe | CH | |
| 3.323 | " | " | " | " | OMe | Me | N | |
| 3.324 | n-Pr | " | CO₂-Et | H | " | " | N | |
| 3.325 | " | " | " | " | " | OMe | CH | |
| 3.326 | " | " | " | " | Me | Me | CH | |
| 3.327 | " | " | CO₂-n-Pr | " | OMe | OMe | CH | |
| 3.328 | i-Pr | " | CO₂-Me | H | OMe | OMe | CH | |
| 3.329 | " | " | " | " | OMe | Me | N | |
| 3.330 | " | " | " | " | Me | Me | CH | |
| 3.331 | " | " | " | " | Cl | OMe | N | |
| 3.332 | " | " | " | Me | OMe | Me | N | |
| 3.333 | " | " | " | " | " | OMe | CH | |
| 3.334 | Allyl | " | CO₂-Me | H | OMe | OMe | CH | |
| 3.335 | " | " | " | " | " | Cl | CH | |
| 3.336 | " | " | " | " | Me | Me | CH | |
| 3.337 | " | " | " | " | OMe | Me | N | |
| 3.338 | " | " | CO₂-Et | H | OMe | OMe | CH | |
| 3.339 | " | " | n-Pr | " | " | " | CH | |
| 3.340 | " | " | i-Pr | " | " | " | CH | |
| 3.341 | Me | COCH₃ | CHO | " | " | " | CH | |
| 3.342 | " | CO₂CH₃ | " | " | " | " | CH | |
| 3.343 | " | COCH₃ | CO—CH₃ | " | " | " | CH | |
| 3.344 | " | CO₂CH₃ | " | " | " | " | CH | |
| 3.345 | " | CO—CH₃ | CO—S-i-Pr | " | " | " | CH | |
| 3.346 | " | CO₂Et | " | " | " | " | CH | |
| 3.347 | " | CHO | CONMe₂ | " | " | " | CH | 180–181 |
| 3.348 | " | " | " | " | OMe | Me | N | |
| 3.349 | " | COCH₃ | " | " | OMe | OMe | CH | 174–175 |
| 3.350 | " | " | CONH₂ | " | " | " | CH | |
| 3.351 | " | COCH₃ | CS—NMe₂ | " | OMe | OMe | CH | |
| 3.352 | " | CO₂Et | " | " | " | " | CH | |
| 3.353 | " | CO—CH₂CH₃ | " | " | " | " | CH | |
| 3.354 | " | CO₂Me | CS—O-i-Pr | " | " | " | CH | |
| 3.355 | " | CHO | " | " | " | " | CH | |
| 3.356 | " | " | C(=N—NMe₂) | " | " | " | CH | |
| 3.357 | Me | CO—CH₃ | C(=N—OMe)OMe | H | OMe | OMe | CH | |
| 3.358 | " | CO₂CH₃ | H | " | " | " | CH | |
| 3.359 | " | CHO | " | " | " | " | CH | |
| 3.360 | " | " | C(=NOH)H | " | " | " | CH | |
| 3.361 | " | CO₂Me | " | " | " | " | CH | |
| 3.362 | " | COCH₃ | C(=NOMe)H | " | " | " | CH | |
| 3.363 | " | " | CO₂H | " | " | " | CH | |
| 3.364 | " | CO₂Me | " | " | " | " | CH | |
| 3.365 | " | COCH₃ | C(=N-Et)OMe | " | " | " | CH | |
| 3.366 | " | " | C(=N-i-Pr)H | " | " | " | CH | |
| 3.367 | " | CO₂CH₂CH₂Cl | COOMe | H | OMe | OMe | CH | 141–143 |
| 3.368 | Me | CO₂CH₂CH₂Cl | COOMe | H | OCH₂CF₃ | NMe₂ | N | 123–126 |
| 3.369 | Me | COCH₂CH₃ | CONMe₂ | H | OMe | OMe | CH | 159–161 |
| 3.370 | Me | COOMe | CONMe₂ | H | OMe | OMe | CH | 133 |
| 3.371 | Me | CO-ⁿC₄H₉ | COOMe | H | OMe | OMe | CH | 189–191 |

B) FORMULATION EXAMPLES a) A dusting agent is obtained by mixing 10 parts by weight of a compound of the formula (I) and 90 parts by weight of talc as inert substance, and comminuting them in an impact mill.

b) A wettable powder which is easily dispersible in water is obtained by mixing 25 parts by weight of a compound of the formula (I), 64 parts by weight of kaolin-containing quartz as inert substance, 10 parts by weight of potassium ligninsulfonate and part by weight of sodium oleoylmethyltaurine as wetting and dispersing agent, and milling them in a pin mill.

c) A dispersion concentrate which is easily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range e.g. about 255° to over 277° C.) and milling them in an attrition ball mill to a fineness of less than 5 microns.

d) An emulsifiable concentrate is obtained from
15 parts by weight of a compound of the formula (I),
75 parts by weight of cyclohexanone as solvent and
10 parts by weight of ethoxylated nonylphenol as emulsifier.

e) Water-dispersible granules are obtained by mixing
75 parts by weight of a compound of the formula (I),
10 parts by weight of calcium ligninsulfonate,
5 parts by weight of sodium lauryl sulfate,
3 parts by weight of polyvinyl alcohol and
7 parts by weight of kaolin,
milling them in a pin mill and granulating the powder in a fluidized bed, spraying on water as the granulation fluid.

c) BIOLOGICAL EXAMPLES

1. Pre-emergence action on weeds

Seeds and/or pieces of rhizome of mono- and dicotyledon weeds were planted in plastic pots in sandy loam soil and covered with earth. The compounds according to the invention, formulated as wettable powders or emulsifiable concentrates, were then applied as an aqueous suspension or emulsion at an equivalent water application rate of 600 to 800 l/ha in different, metered amounts to the surface of the covering earth.

After treatment, the pots are placed in a greenhouse and maintained under good growth conditions for the weeds. The visual assessment of the plants and/or the emergence damage is made following the emergence of the test plants after a test period of 3 to 4 weeks, in comparison to untreated controls. As the test results show, the compounds according to the invention display a good herbicidal pre-emergence activity against a broad spectrum of graminaceous and other weeds. For example, the compounds from Examples 12, 13, 15, 16, 18, 44, 89, 90, 91, 92, 93, 94, 96, 122, 167, 170, 173, 175, 246, 322, 324, 325, 327, 477, 555, 945, 1.023, 1.178, 1.256, 1.334, 1.802, 2.192, 2.270, 2.715, 2.951, 3.347, 3.349, 3.367, 3.368, 3.369, 3.370 and 3.371 from Table 1 have a very good herbicidal action against harmful plants such as Sinapis alba, Chrysanthemum segetum, Avena sative, Stellaria media, Echinochloa crus-galli and Lolium multiflorum in the pre-emergence method at an application rate of 0.3 kg or less of active substance per hectare.

2. Post-emergence action on weeds

Seeds and/or pieces of rhizome from mono- and dicotyledon weeds were placed in plastic pots in sandy loam soil, covered with earth and cultivated in a greenhouse under good growth conditions. Three weeks after being sown, the test plants were treated at the three-leaf stage.

The compounds according to the invention, formulated as wettable powders or as emulsifiable concentrates, were sprayed in different, metered amounts at an equivalent water application rate of 600 to 800 l/ha onto the green parts of the plants: after a 3- to 4-week standing time of the test plants in a greenhouse under optimum growth conditions, the activity of the formulations was assessed visually in comparison to untreated controls. Applied post-emergence, too, the agents according to the invention display a good herbicidal activity against a broad spectrum of economically significant graminaceous and other weeds. For example, the compounds of Examples 12, 13, 15, 16, 18, 44, 89, 90, 91, 92, 93, 94, 96, 122, 167, 170, 173, 175, 246, 322, 324,325, 327, 477, 555, 945, 1.023, 1.178, 1.256, 1.334, 1.802, 2.192, 2.270, 2.715, 2.951, 3.347, 3.349, 3.367, 3.368, 3.369, 3.370 and 3.371 from Table 1 have a very good herbicidal action against harmful plants such as Sinapis alba, Stellaria media, Echinochloa crus-galli, Lolium multiflorum, Chrysanthemum sagetum and Avena sativa in the post-emergence method at an application rate of 0.3 kg or less of active substance per hectare.

We claim:
1. A compound of the formula (I) or a salt thereof

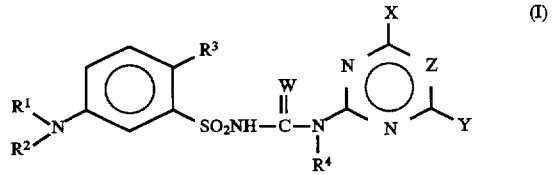

in which $R^1$ is $C_1$–$C_6$-alkyl, $C_2$–$C_6$-alkenyl, $C_2$–$C_6$-alkynyl, the 3 latter radicals independently of one another being unsubstituted or substituted by one or more radicals from the group consisting of halogen, $C_1$–$C_4$-alkoxy, $CONH_2$, $C_1$–$C_4$-alkylthio, CN, CHO, ($C_1$–$C_6$-alkyl)carbonyl, ($C_3$–$C_6$-cycloalkyl)carbonyl, $C_1$–$C_4$-alkylsulfonyl, carboxyl, ($C_1$–$C_4$-alkoxy)carbonyl, ($C_2$–$C_4$-alkenyloxy)carbonyl, ($C_2$–$C_4$-alkynyloxy)carbonyl, $NO_2$, $NH_2$, mono- and di-($C_1$–$C_6$)-alkylamino, $R^2$ is CO—$R^5$, COO—$R^5$, CO—$SR^7$, CO—$NR^8R^9$, CS—$NR^{10}R^{11}$, CS—$OR^{12}$, CS—$SR^{13}$, $SO_2R^{14}$, $SO_2NR^{15}R^{16}$, $R^3$ is $COR^{17}$, CO—$OR^{18}$, CO—$NR^{19}R^{20}$, CO—$SR^{21}$, COO—N=$CR^{22}R^{23}$, $CSR^{24}$, $CSSR^{25}$, CS—$OR^{26}$, CS—$NR^{27}R^{28}$, C(=$NR^{29}$)$R^{30}$, $R^4$ is H, $C_1$–$C_6$-alkyl, $C_2$–$C_6$-alkenyl, $C_2$–$C_6$-alkynyl, the 3 latter radicals independently of one another being unsubstituted or substituted by one or more halogen radicals, $R^5$ is H, $C_1$–$C_6$-alkyl, $C_2$–$C_6$-alkenyl, $C_2$–$C_6$-alkynyl, the three latter radicals independently of one another being unsubstituted or substituted by one or more radicals from the group, consisting of halogen, $C_1$–$C_4$-alkoxy, $C_1$–$C_4$-alkylthio and $NR^{31}R^{32}$, or unsubstituted or substituted $C_3$–$C_8$-cycloalkyl, unsubstituted or substituted phenyl, pyridyl, pyrimidinyl, pyridazinyl, pyrazinyl, thienyl, thiazolyl, oxazolyl, furyl, pyrrolyl, pyrazolyl or imidazolyl, where each of the eleven last-mentioned radicals is unsubstituted or substituted by one or more radicals from the group consisting of $C_1$–$C_4$-alkyl, $C_1$–$C_4$-alkoxy and halogen or phenyl-$C_1$–$C_4$-alkyl which is unsubstituted or substituted on the phenyl ring, $R^6$ is $C_1$–$C_6$-alkyl, $C_2$–$C_6$-alkenyl, $C_2$–$C_6$-alkynyl, the three latter radicals independently of one another being unsubstituted or substituted by one or more radicals from the group consisting of halogen, $C_1$–$C_4$-alkoxy, $C_1$–$C_4$-alkylthio and $NR^{31}R^{32}$, or $C_3$–$C_6$-cycloalkyl which is unsubstituted or substituted by one or more radicals from the group consisting of halogen, $C_1$–$C_4$-alkyl and $C_1$–$C_4$-alkoxy, or $C_3$–$C_6$-cycloalkyl-$C_1$–$C_3$-alkyl, $R^7$ is selected from the group of radicals as defined in $R^6$, $R^8$ is H, $C_1$–$C_6$-alkyl, $C_2$–$C_6$-alkenyl, $C_2$–$C_6$-alkynyl, the 3 latter radicals independently of one another being unsubstituted or substituted by one or more radicals from the group consisting of halogen, or ($C_1$–$C_6$)-alkoxy)carbonyl or $C_1$–$C_4$-alkoxy, $R^9$ is H, $C_1$–$C_6$-alkyl, $C_2$–$C_6$-alkenyl, $C_2$–$C_6$-alkynyl, the 3 latter radicals independently of one another being unsubstituted or substituted by one or more radicals from the group consisting of halogen, $C_1$–$C_4$-alkoxy, $C_1$–$C_4$-alkylthio and $NR^{31}R^{32}$, or $CO$—$R^{33}$, $CO$—$OR^{34}$, $CO$—$NR^{35}R^{36}$, $CS$—$NR^{35}R^{36}$, $CS$—$R^{33}$ or $CS$—$OR^{34}$, or $R^8$, $R^9$ taken together are a divalent radical of the formula —($CH_2$)$_4$—, —($CH_2$)$_5$—, —$CH_2CH_2$—O—$CH_2CH_2$—, —$CH_2CH_2NHCH_2CH_2$—, the 4 latter radicals being unsubstituted or substituted by $C_1$–$C_4$-alkyl, $R^{10}$ is selected from the group of radicals as defined in $R^8$, $R^{11}$ is selected from the group of radicals as defined in $R^9$, $R^{12}$ is selected from the group of radicals as defined in $R^6$, $R^{13}$ is selected from the group of radicals as defined in $R^6$, $R^{14}$ is $C_1$–$C_6$-alkyl, $C_2$–$C_6$-alkenyl, $C_2$–$C_6$-alkynyl, the three latter radicals independently of one another being unsubstituted or substituted by one or more radicals from the group consisting of halogen, $C_1$–$C_4$-alkoxy, $C_1$–$C_4$-alkylthio and $NR^{31}R^{32}$, $R^{15}$ is selected from the group of radicals as defined in $R^8$, $R^{16}$ is H, $C_1$–$C_6$-alkyl, $C_2$–$C_6$-alkenyl, $C_2$–$C_6$-alkynyl, the 3 latter radicals independently of one another being unsubstituted or substituted by one or more halogen radicals, $R^{17}$ is selected from the group of radicals as defined in $R^5$, $R^{18}$ is $C_1$–$C_6$-alkyl, $C_2$–$C_6$-alkenyl, $C_2$–$C_6$-alkynyl, the three latter radicals independently of one another being unsubstituted or substituted by one or more radicals from the group consisting of halogen, $C_1$–$C_4$-alkoxy, $C_1$–$C_4$-alkylthio and $NR^{31}R^{32}$, or $C_3$–$C_6$-cycloalkyl which is unsubstituted or substituted by one or more radicals from the group consisting of halogen, $C_1$–$C_4$-alkyl and $C_1$–$C_4$-alkoxy, or $C_3$–$C_6$-cycloalkyl-$C_1$–$C_3$-alkyl or H, $R^{19}$ is selected from the group of radicals as defined in $R^8$, $R^{20}$ is selected from the group of radicals as defined in $R^9$, $R^{21}$ is selected from the group of radicals as defined in $R^{18}$, $R^{22}$ is H, $C_1$–$C_4$-alkyl, $C_3$–$C_5$-alkenyl or $C_3$–$C_5$-alkynyl, $R^{23}$ is H, $C_1$–$C_4$-alkyl, $C_3$–$C_5$-alkenyl or $C_3$–$C_5$-alkynyl, $R^{24}$ is selected from the group of radicals as defined in $R^{17}$, $R^{25}$ is selected from the group of radicals as defined in $R^{18}$, $R^{26}$ is selected from the group of radicals as defined in $R^{18}$, $R^{27}$ is selected from the group of radicals as defined in $R^8$, $R^{28}$ is selected from the group of radicals as defined in $R^9$, $R^{29}$ is H, OH, $NH_2$, $NHR^{37}$, $N(R^{37})_2$, $C_1$–$C_4$-alkyl, $C_1$–$C_4$-alkoxy, $C_2$–$C_4$-alkenyl or $C_2$–$C_4$-alkynyl, the 4 latter radicals independently of one another being unsubstituted or substituted by one or more radicals from the group consisting of halogen, $C_1$–$C_3$-alkoxy and $C_1$–$C_3$-alkylthio, $R^{30}$ is H, $C_1$–$C_6$-alkyl, $C_1$–$C_6$-alkoxy, $C_2$–$C_6$-alkenyl, $C_2$–$C_6$-alkynyl, the four latter radicals independently of one another being unsubstituted or substituted by one or more radicals from the group consisting of halogen, $C_1$–$C_3$-alkoxy and $C_1$–$C_3$-alkylthio, each $R^{31}$ independently of the others is H, $C_1$–$C_4$-alkyl, ($C_1$–$C_4$-alkyl)carbonyl, ($C_1$–$C_4$-alkoxy)carbonyl or CHO, each $R^{32}$ independently of the others is H or $C_1$–$C_4$-alkyl, $R^{33}$ is selected from the group of radicals as defined in $R^5$, $R^{34}$ is selected from the group of radicals as defined in $R^6$, $R^{35}$, $R^{36}$ independently of one another are H, $C_1$–$C_6$-alkyl, $C_2$–$C_6$-alkenyl, $C_2$–$C_6$-alkynyl, the 3 latter radicals independently of one another being unsubstituted or substituted by one or more halogen radicals, $R^{37}$ is $C_1$–$C_4$-alkyl, $C_2$–$C_4$-alkenyl or $C_2$–$C_4$-alkynyl, the three radicals mentioned, independently of one another, being unsubstituted or substituted by one or more radicals from the group consisting of halogen, $C_1$–$C_4$-alkoxy and $C_1$–$C_4$-alkylthio, W is O or S, X and Y independently of one another are hydrogen, halogen, $C_1$–$C_6$-alkyl, $C_1$–$C_6$-alkoxy or $C_1$–$C_6$-alkylthio, the three latter radicals being unsubstituted or substituted by one or more radicals from the group consisting of halogen, $C_1$–$C_4$-alkoxy and $C_1$–$C_4$-alkylthio, or mono- or di-($C_1$–$C_4$-alkyl)amino, $C_3$–$C_6$-cycloalkyl, $C_3$–$C_5$-alkenyl, $C_3$–$C_5$-alkenyloxy or $C_3$–$C_5$-alkynyloxy, and Z is CH.

2. A compound or a salt thereof as claimed in claim 1, wherein $R^1$ is $C_1$–$C_4$-alkyl, $C_2$–$C_4$-alkenyl or $C_2$–$C_4$-alkynyl, or $R^2$ is CO—$R^5$, COOR$^6$, CO—$NR^8R^9$, CS—$NR^{10}R^{11}$, $SO_2R^{14}$ or $SO_2NR^{15}R^{16}$, or $R^3$ is COR$^{17}$, COOR$^{18}$, CONR$^{19}R^{20}$ or CO—ON=CR$^{22}R^{23}$, or $R^4$ is H, $C_1$–$C_4$-alkyl, or $R^5$ is H, $C_1$–$C_6$-alkyl which is unsubstituted or substituted by one or more halogen atoms, or by $C_1$–$C_4$-alkoxy, $C_1$–$C_4$-alkylthio, or $NR^{31}R^{32}$, or is $C_3$–$C_6$-cycloalkyl, phenyl, benzyl or pyridyl, pyrimidinyl, pyridazinyl, pyrazinyl, thienyl, thiazolyl, oxazolyl, furyl, pyrrolyl, pyrazolyl, imidazolyl, the thirteen latter radicals being unsubstituted or substituted by one or more radicals from the group consisting of $C_1$–$2C_4$-alkyl, $C_1$–$C_4$-alkoxy and halogen, or $R^6$ is $C_1$–$C_6$-alkyl, $C_2$–$C_6$-alkenyl, $C_2$–$C_6$-alkynyl, $C_1$–$C_6$-haloalkyl or $C_3$–$C_6$-cycloalkyl, or $R^7$ is $C_1$–$C_4$-alkyl, $R^8$ is hydrogen, $C_1$–$C_6$-alkyl, $C_1$–$C_4$-haloalkyl, $C_1$–$C_4$-alkoxy or ($C_1$–$C_4$-alkoxy)carbonyl, $R^9$ is hydrogen, $C_1$–$C_6$-alkyl which is unsubstituted or substituted by one or more radicals from the group consisting of halogen, $C_1$–$C_4$-alkoxy and $NR^{31}R^{32}$, or CO—$R^{33}$, CO—$OR^{34}$ or CO—$NR^{35}R^{36}$, or $R^8$ and $R^9$ taken together are a divalent radical of the formula —$(CH_2)_4$—, —$(CH_2)_5$— or —$CH_2CH_2$—O—$CH_2CH_2$—, or $R^{14}$ is $C_1$–$C_6$-alkyl or $C_2$–$C_6$-haloalkyl, or $R^{15}$, $R^{16}$ independently of one another are hydrogen or $C_1$–$C_4$-alkyl, or $R^{17}$ is hydrogen or $C_1$–$C_4$-alkyl, $C_1$–$C_4$-haloalkyl, $C_3$–$C_6$-cycloalkyl, phenyl, pyridyl, pyrimidinyl, pyridazinyl, pyrazinyl, thienyl, thiazolyl, oxazolyl, furyl, pyrrolyl, pyrazolyl, imidazolyl, the latter twelve radicals being unsubstituted or substituted, by one or more radicals from the group consisting of $C_1$–$C_4$-alkyl, $C_1$–$C_4$-alkoxy and halogen or $R^{18}$ is hydrogen, $C_1$–$C_4$-alkyl, $C_2$–$C_6$-alkenyl or $C_2$–$C_6$-alkynyl, the 3 latter radicals being unsubstituted or substituted by one or more radicals from the group consisting of halogen, $C_1$–$C_4$-alkoxy, $C_1$–$C_4$-alkylthio and $NR^{31}R^{32}$, or $C_3$–$C_6$-cycloalkyl or $C_3$–$C_6$-cycloalkyl-$C_1$–$C_3$-alkyl, or $R^{22}$ is hydrogen or $C_1$–$C_2$-alkyl, or $R^{23}$ is hydrogen or $C_1$–$C_2$-alkyl, or $R^{29}$ is hydrogen, hydroxyl, amino, $NHCH_3$, $N(CH_3)_2$, $C_1$–$C_4$-alkyl or $C_1$–$C_4$-alkoxy, $R^{30}$ is hydrogen or $C_1$–$C_4$-alkyl, or each $R^{31}$ independently of the others is H or $C_1$–$C_4$-alkyl, or each $R^{32}$ independently of the others is H or $C_1$–$C_4$-alkyl, or $R^{33}$ is hydrogen, $C_1$–$C_4$-alkyl, $C_1$–$C_4$-haloalkyl, $C_3$–$C_6$-cycloalkyl or phenyl which is unsubstituted or substituted by one or more radicals from the group consisting of halogen, $C_1$–$C_4$-alkyl and $C_1$–$C_4$-alkoxy, or $R^{34}$ is $C_1$–$C_4$-alkyl, allyl, propargyl or cycloalkyl, or $R^{35}$ is hydrogen or $C_1$–$C_4$-alkyl, or $R^{36}$ is hydrogen or $C_1$–$C_4$-alkyl, or X is $C_1$–$C_4$-alkyl, $C_1$–$C_4$-alkoxy, $C_1$–$C_4$-haloalkyl, $C_1$–$C_4$-alkylthio, halogen or mono- or di-($C_1$–$C_2$-alkyl)amino, or Y is $C_1$–$C_4$-alkyl, $C_1$–$C_4$-alkoxy, $C_1$–$C_4$-haloalkyl or $C_1$–$C_4$-alkylthio.

3. A compound or a salt thereof as claimed in claim 1, wherein $R^1$ is methyl, ethyl, n-propyl, i-propyl or allyl, $R^2$ is CO—$R^5$, COO$R^6$, CO—$NR^8R^9$, CS—$NR^{10}R^{11}$, $SO_2R^{14}$ or $SO_2NR^{15}R^{16}$, $R^5$ is H, $C_1$–$C_4$-alkyl, $C_1$–$C_2$-haloalkyl, cyclopropyl, phenyl, benzyl or pyridyl, thienyl or furyl, where each of the 5 latter radicals are unsubstituted or substituted by one or more halogen atoms, $R^6$ is $C_1$–$C_4$-alkyl, allyl, propargyl or cyclopropyl, $R^8$ is H, $C_1$–$C_4$-alkyl, $C_1$–$C_4$-haloalkyl or ($C_1$–$C_4$-alkoxy)carbonyl, $R^9$ is H or $C_1$–$C_4$-alkyl, $R^{10}$ is H or $C_1$–$C_4$-alkyl, $R^{11}$ is H or $C_1$–$C_4$-alkyl, $R^{14}$ is $C_1$–$C_4$-alkyl, $R^{15}$ is H or $C_1$–$C_4$-alkyl and $R^{16}$ is H or $C_1$–$C_4$-alkyl.

4. A herbicidal or plant growth-regulating composition, which comprises a compound of the formula (I) as claimed in claim 1 and conventional formulation auxiliaries.

5. A method of controlling harmful plants or of regulating the growth of plants, which comprises applying an effective amount of one or more compounds of the formula (I) or of salts thereof as claimed in claim 1, to the plants, parts of plants or the agricultural or industrial land.

6. A compound of formula (I) or a salt thereof as claimed in claim 1, wherein $R^1$ is methyl, ethyl, n-propyl, i-propyl or allyl, $R^2$ is formyl, acetyl, methoxycarbonyl, ethoxycarbonyl, 2-chloroethoxycarbonyl, ethoxycarbonylaminothiocarbonyl, methylaminosulfonyl or methylsulfonyl, $R^3$ is methoxycarbonyl or ethoxycarbonyl, $R^4$ is hydrogen or methyl, W is O, X is methyl, methoxy or chloro, Y is methyl or methoxy, and Z is CH.

7. A compound or a salt thereof as claimed in claim 6 wherein $R^1$ is methyl, ethyl, n-propyl, i-propyl or allyl, $R^2$ is formyl, acetyl, methoxycarbonyl or ethoxycarbonyl, and $R^3$ is methoxycarbonyl.

* * * * *